US009415067B2

(12) United States Patent
Jones et al.

(10) Patent No.: US 9,415,067 B2
(45) Date of Patent: Aug. 16, 2016

(54) GENETIC TEST FOR LIVER COPPER ACCUMULATION IN DOGS AND LOW COPPER PET DIET

(71) Applicant: Mars, Inc., McLean, VA (US)

(72) Inventors: Paul Glyn Jones, Leicestershire (GB); Alan James Martin, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 0 days.

(21) Appl. No.: 14/021,376

(22) Filed: Sep. 9, 2013

(65) Prior Publication Data

US 2014/0093584 A1 Apr. 3, 2014
US 2016/0184355 A9 Jun. 30, 2016

Related U.S. Application Data

(63) Continuation of application No. 13/263,282, filed as application No. PCT/GB2010/000703 on Apr. 7, 2010, now abandoned.

(30) Foreign Application Priority Data

| Apr. 8, 2009 | (GB) | 0906162.3 |
| Jul. 30, 2009 | (GB) | 0913309.1 |
| Oct. 5, 2009 | (WO) | PCT/GB2009/002355 |

(51) Int. Cl.

| C07H 21/04 | (2006.01) |
| C12Q 1/68 | (2006.01) |
| A61K 33/34 | (2006.01) |
| A23K 1/175 | (2006.01) |
| A23K 1/18 | (2006.01) |
| A61K 33/30 | (2006.01) |
| A61K 9/00 | (2006.01) |

(52) U.S. Cl.
CPC ............. *A61K 33/34* (2013.01); *A23K 1/175* (2013.01); *A23K 1/1758* (2013.01); *A23K 1/1853* (2013.01); *A61K 9/0056* (2013.01); *A61K 33/30* (2013.01); *C12Q 1/6883* (2013.01); *C12Q 1/6888* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 6,156,355 A | 12/2000 | Shields, Jr. et al. |
| 6,911,224 B1 | 6/2005 | May et al. |
| 2003/0092019 A1* | 5/2003 | Myers ............ C12Q 1/68 |
| 2005/0123585 A1 | 6/2005 | Cox et al. |
| 2007/0009899 A1* | 1/2007 | Mounts ............ C12Q 1/68 |
| 2010/0278938 A1* | 11/2010 | Jones ............ A61K 33/34 |
| 2012/0021928 A1 | 1/2012 | Lindblad-Toh et al. |

FOREIGN PATENT DOCUMENTS

| DE | 19703252 A1 | 5/1998 |
| EP | 1698232 A1 | 9/2006 |
| JP | 2007528205 A | 10/2007 |
| WO | 95/08641 A1 | 3/1995 |
| WO | 99/48384 A2 | 9/1999 |
| WO | 00/32206 A1 | 6/2000 |
| WO | 02/056703 A1 | 7/2002 |
| WO | 03/033734 A2 | 4/2003 |
| WO | 2004/113570 A2 | 12/2004 |
| WO | 2005/055739 A1 | 6/2005 |
| WO | 2009/044152 | 2/2009 |
| WO | 2010/038032 A1 | 4/2010 |

OTHER PUBLICATIONS

Flint River Ranch Super Premium DryWater Kibble Dog Food, product sheet, Downloaded 2014.*
Force Dog Food—Gluten Free, The Honest Kitchen, product sheet, downloaded 2014.*
Copper Content in Dog Foods (http:rottndobie.tripod.com/coppercontent.html, Nov. 2004).*
The Best foods for Dogs with Chronic Active Hepatitis (http://phoenixdogphotography.com/2010/06/the-best-foods-for-dogs-with-chronic-active-hepatitis).*
Hoffmann et al. (J. Vet. Intern Med, vol. 2006, vol. 20, pp. 856-861, 2006).*
Noaker et al (JAVMA, vol. 214, No. 10, pp. 1502-1506, 1999).*
Great Life Grain/Potato Free Dog Food as evidenced by Great Life Rubicon (www.healthyplanetrx.com/Great-Life-Rubicon-for-dogs-p, Jul. 5, 2006).*
Murphy et al. (Genbank Accession No. AY011436, Feb. 7, 2001).*
Poulsen et al., "X-Linked recessive Menkes disease: carrier detection in the case of a partial gene deletion", Clinical Genetics, 2002, vol. 62, pp. 440-448.
Coronado et al., "New haplotypes in the Bedlington terrier indicate complexity in copper toxicosis", Mammalian Genome, Dec. 4, 2002, pp. 483-491, Springer-Verlag, New York, Inc. 2003.
Hoffman et al., "Copper-Associated Chronic Hepatitis in Labrador Retrievers", J. Vet Intern. Med. 2006, vol. 20, pp. 856-861.

(Continued)

*Primary Examiner* — Jeanine A Goldberg

(74) *Attorney, Agent, or Firm* — Mars, Incorporated; Rebecca Barnett

(57) ABSTRACT

The present invention provides a method of testing a dog to determine the likelihood that the dog is protected from liver copper accumulation, comprising detecting in a sample the presence or absence in the genome of the dog of one or more polymorphisms selected from (a) SNP ATP7a_Reg3_F_6 (SEQ ID NO:142) and (b) one or more polymorphisms in linkage disequilibrium with (a).

11 Claims, 12 Drawing Sheets

(56) References Cited

OTHER PUBLICATIONS

Hyun et al., "Evaluation of haplotypes associated with copper toxicosis in Bedlington Terriers in Australia", AJVR, Nov. 2004, vol. 65, No. 11, pp. 1573-1579.

Spee et al., "Differential expression of copper-associated and oxidative stress related proteins in a new variant of copper toxicosis in Doberman pinschers", Comparative Hepatology, 2005, 4:3, p. 1-13.

"The Best Foods for Dogs With Chronic Active Hepatitis", A Dog's Life Photography & Art [online], Jun. 29, 2010, [retrieved on Aug. 21, 2013], Internet >URL :http://phoenixdogphotography.com/2010/06/the-best-foods-for-dogs-with-chronic-active-hepatitis/>.

English translation of Japnese Office Action dated Sep. 2, 2014, JP Appl. No. 2012-504068.

Van De Sluis, "Identification of a new copper metabolism gene by positional cloning in a purebred dog population," Human Molecular Genetics, 2002, vol. 11, No. 2, pp. 165-173.

Search Report issued in United Kingdom Application No. GBI120989.7, dated Mar. 30, 2012.

Burns, "Burns: Developed by a Veterinary Surgeon. The Holistic Approach to Health & Nutrition," Burns Pet Nutrition Ltd., product brochure, available online at http://www.burns-petnutrition.co.uk/colour_brochure2006_small.pdf, accessed Jan. 30, 2008.

"Premium Nutrition for Dogs, Nature's Recipe Large Breed Recipe, Product Description" Del Monte: Nature's Recipe®, 2007, available online at http://www.naturesrecipe.com/DogProductDisplay.aspx?p=Dogs/Breed_LargeBreed.

"Premium Nutrition for Dogs, Terrier Dogs Canine Recipe Product Description" Del Monte: Nature's Recipe®, available online at http://www.naturesrecipe.com/dogproductdisplay.aspx?p=Dogs/Breed_dryTerrier, 2006.

"Prescription Diet Canine lid (liver disease)," Hills Pet Nutrition, available online at http://www.hillspet.com/media/WEURG/product/prodkeyPDF /en/PD K9 D d Id_o_0_n o WEURG_prodkey_en.pdf, accessed Jan. 30, 2008.

"Trophy Pet Foods: Trophy Premium Hypo-Allergenic food," Trophy Pet Foods, available online at http://www.trophypetfoods.co.uk/products/premiumdog.htm, accessed Jan. 30, 2008.

Allen et al., "Tetramine cupruretic agens: A comparison in dogs," Am. J. Vet. Res., 1987, vol. 48, Issue 1, pp. 28-30.

Coronado et al., "Polymorphisms in canine A TP7B: candidate modifier of copper toxicosis in the Bedlington terrier", Veterinary Journal, 2008, vol. 177, Issue 2, pp. 293-296.

Friedman et al., "Isolation of a ubiquitin-like (UBL5) gene from a screen identifying highly expressed and conserved iris genes", Genomics, 2001, vol. 71, Issue 2, pp. 252-255.

Haywood et al., "Copper toxicosts in the bedlington terrier: a diagnostic dilemma," Journal of Small Animal Practice, 2001, vol. 42, Issue 4, pp. 181-185.

Hoffmann et al., "Copper-associated chronic hepatitis in Labrador retrievers", Journal of Veterinary Internal Medicine, 2006, vol. 20, Issue 4, pp. 856-861.

Madsen et al., "Zebrafish mutants calamity and catastrophe define critical pathways of genenutrient interactions in developmental copper metabolism", PLOS Genetics, 2008, vol. 4, Issue 11, pp. 1-11.

PCT International Preliminary Report on Patentability issued in International application No. PCT/GB2009/002355, dated Apr. 14, 2011.

PCT International Search Report and Written Opinion issued in International Application No. PCT/GB2008/003351, mailed May 27, 2009.

PCT International Search Report and Written Opinion issued in International Application No. PCT/GB2010/000703, mailed Jun. 16,2010.

PCT International Search Report issued in International Application No. PCT/GB2009/002355, mailed Nov. 26, 2009.

Shih et al., "Chronic hepatitis in Labrador retrievers: clinical presentation and prognostic factors", Journal of Veterinary Internal Medicine, 2007, vol. 21, Issue 1, pp. 33-39.

Shimizu et al., "Treatment and management of Wilson's disease", Pediatrics International, 1999, vol. 41, pp. 419-422.

Spee et al., "Copper metabolism and oxidative stress in chronic inflammatory and cholestatic liver disease in dogs", Journal of Veterinary Internal Medicine, 2006, vol. 20, Issue 5, pp. 1085-1092.

PCT International Preliminary Report on Patentability, issued in International application No. PCT/US2008/003351, dated Apr. 7, 2010.

Dietary Survey Study Jun. 5, 2010; Utrecht University.

Bergstrom et al., "The Pharmacokinetics of Penicillamine in a Female Mongrel Dog", Journal of Pharmacokinetics and Biopharmaceutics, Feb. 6, 1981, vol. 9, No. 5, pp. 603-621, Plenum Publishing Corporation.

Xiaoqing et al., English Abstract "Application of D13S301 Label in Diagnosis of Wilson Disease", Journal of Clinical Pediatrics, Oct. 20, 2002, vol. 20, No. 10, pp. 614-616.

Yuxin et al., "Preliminary Study on Mutations of Copper Transporting P-Type ATPase Gene in the Chinese", Journal of Fudan University (Natural Science), Oct. 1997, vol. 36, No. 5., pp. 517-523.

"Whole Dog Journal's Food List", Little Dog & Girl on the Prairie, Jun. 27, 2007, Internet <URL: http://blog.livedoor.jp/urea/archives/51627947.html>.

"University study shows dogs have a lot to gain when they lose weight", GoodNewsforPets.com, recorded on May 12, 2007, Internet Archive Wayback Machine, searched http://goodnewsforpets.com/news/archive/Research/041300_weight_study.htm, Internet <URL:http://web.archive.org/web/20070512095423/http://www.goodnewsforpets.com/news/archive/research/041300_weight_study.htm>.

Fuentealba et al., "Animal models of copper-associates liver disease", Comparative Hepatology, Apr. 3, 2003, vol. 2, No. 1, p. 5.

"Health and Related Issues", Internet <URL: http://homepages.rootsweb.ancestry.com/oldmill/chelseaBB/HealthPage.htm>.

Chinese Search Report dated Mar. 8, 2013 issued during prosecution of China Patent Application No. 2010800254455.

Murphy et al. (Genbank Accession No. AY011436, Feb. 7, 2001 ).

Hirschhorn et al. (Genetics in Medicine. vol. 4, No. 2, pp. 45-61, Mar. 2002).

Ioannidis (Nature Genetics, vol. 29, pp. 306-309, Nov. 2001).

PCT International Report on Patentability issued in International Application No. PCT/GB2009/002355, dated Apr. 14, 2011.

PCT International Report on Patentability issued in International Application No. PCT/GB2010/000703, dated Jun. 16, 2010.

"dbSNP Short Genetic Variations", Database Medline US National Library of Medicine (NLM), Bethesda, MD, US, Feb. 2, 2005, XP002696928, Database accession No. rs22088177.

"Hill's Pet Nutrition Hills Prescription L/D", Hill's Pet Nutrition, Aug. 26, 2015.

"Nutrient Analysis", Hill's Pet Nutrition, Inc., Jan. 19, 1999.

"Regenerative and Fibrotic Pathways in Canine Liver Disease", Faculty of Veterinary Medicine, 2006.

"Small Animal Clinical Nutrition", Mark Morris Institute, 2000, Ed. 4th.

"The Hill's Key to Clinical Nutrition", Hill's Pet Nutrition, Inc., 1999.

Stuehler, et al., "Analysis of the Human Homologue of the Canine Copper Toxicosis Gene MURR1 in Wilson Disease Patients", Journal of Molecular Medicine, vol. 82, No. 9, Sep. 2004, pp. 629-634.

Thornburg, "A Perspective on Copper and Liver Disease in the Dog", J. Vet. Diagn. Invest, Dec. 31, 2000, vol. 12, pp. 101-110.

* cited by examiner

A

B

C

GENETIC TEST FOR LIVER COPPER ACCUMULATION IN DOGS AND LOW COPPER PET DIET

This application is a continuation of co-pending U.S. patent application Ser. No. 13/263,282 filed Apr. 7, 2010, which claims priority to PCT International Application Serial No. PCT/GB2010/000703, filed Apr. 7, 2010, and to PCT/GB09/02355, filed Oct. 5, 2009 and to GB Patent Application Serial No. 0913309.1, filed Jul. 30, 2009 and to GB Patent Application Serial No. 0906162.3 filed Apr. 8, 2009, all of which applications are incorporated by reference herein in their entirety.

FIELD OF THE INVENTION

The invention relates to a method of determining the likelihood that a dog is protected from liver copper accumulation and from copper-associated liver disease. The invention also relates to a foodstuff for dogs for use in preventing liver copper accumulation and copper-associated liver disease in a dog and a method of making the foodstuff.

BACKGROUND OF THE INVENTION

Although liver diseases are uncommon in dogs, one of its most common forms is chronic hepatitis (CH). CH is a histologic diagnosis, characterised by the presence of fibrosis, inflammation, and hepatocellular apoptosis and necrosis. Cirrhosis can result as the end stage of the disease. One of the causes of CH is hepatic copper accumulation. Hepatic copper accumulation can result from increased uptake of copper, a primary metabolic defect in hepatic copper metabolism, or from altered biliary excretion of copper. In the latter case, copper toxicity is secondary to hepatic inflammation, fibrosis, and cholestasis, although it is unclear to what extent this occurs in the dog. In secondary copper storage disease, copper accumulation is mainly restricted to periportal parenchyma and hepatic copper concentrations are lower than accumulation in familial storage diseases. Whilst, the nature of the initiating factor(s) and of the sensitizing antigen is unknown, immunological abnormalities and morphologic features observed in primary biliary cirrhosis are concurrent with an immune mediated mechanism.

The small intestine is recognized as the main site of dietary copper absorption in mammals. Transport from the intestinal lumen into intestinal mucosa is a carrier-mediated process involving a saturable transport component. Once in mucosal cells, approximately 80% of the newly absorbed copper is in the cytosol, mainly bound to metallothioneins (MT). These are low molecular weight inducible proteins with many functions including homeostasis, storage, transport and detoxification of metals. After passage through the enterocytes, copper enters the portal circulation where it is bound to carrier proteins peptides and amino acids and is transported to the liver with lesser amounts entering the kidney. In most mammals, copper is excreted easily, and the main route of excretion of copper is the bile.

The genetic basis for hepatic copper accumulation is unknown. This is made difficult by the fact that copper is involved in numerous different biological pathways, each of which is highly complex and involves a large number of genes. Dogs with excessive hepatic copper accumulation are typically treated with D-penicillamine, a potent copper chelator. Ultimately however, the most successful treatment available for dogs with CH is liver transplantation.

WO 2009/044152 A2 discloses a method of determining the susceptibility of a dog to liver copper accumulation comprising detecting the presence or absence of (a) a polymorphism in the GOLGA5, ATP7a or UBL5 gene of the dog that is indicative of susceptibility to copper accumulation and/or (b) a polymorphism in linkage disequilibrium with a said polymorphism (a), and thereby determining the susceptibility of the dog to liver copper accumulation. International application no. PCT/GB09/02355 (not yet published) discloses further polymorphisms for use in a method of determining the susceptibility of a dog to liver copper accumulation.

SUMMARY OF THE INVENTION

The inventors have discovered a coding mutation in the canine ATP7A gene that is associated with low levels of liver copper in dogs and therefore indicative of protection from liver copper accumulation. The mutation is a single nucleotide polymorphism (SNP) that causes an amino acid change in the protein. In a study described herein, the polymorphism has been shown to have a functional impact on copper transport in cells. The discovery of this polymorphism in the ATP7A gene provides the basis for a test to predict whether a dog is protected from liver copper accumulation by screening for this polymorphism and/or one or more polymorphisms in linkage disequilibrium with this polymorphism.

The inventors also recently discovered that polymorphisms in or in the region of the canine GOLGA5, ATP7A and UBL5 genes that are associated with high levels of liver copper in dogs and therefore indicative of susceptibility to liver copper accumulation (WO 2009/044152 A2 and unpublished International application no. PCT/GB09/02355). Therefore, a genetic test which combines the results of detecting one or more polymorphisms indicative of protection from liver copper accumulation with the results of detecting one or more polymorphisms indicative of susceptibility to liver copper accumulation in dogs would be particularly informative with regards to the likelihood that a dog is at risk of liver copper accumulation.

The accumulation of copper in the liver of a dog may lead to one or more diseases or conditions of the liver that are attributable to high liver copper. For example, high liver copper can lead to chronic hepatitis, liver cirrhosis and ultimately liver failure. The invention thus enables dogs to be identified which are not protected from, or are at risk of developing, such liver diseases or conditions that are associated with high copper. Once a dog has been identified has not having a mutation indicative of protection from liver copper accumulation, it is possible to identify suitable preventative measures for that dog, with the aim of maintaining the liver copper level at a low or normal level, such as by administering the foodstuff of the invention. Furthermore, dogs that are identified as having mutations associated with protection from liver copper accumulation are ideal for use in breeding programs with the aim of producing dogs that are less likely to suffer from liver disease or other conditions associated with high copper.

Thus, the invention provides a method of testing a dog to determine the likelihood that the dog is protected from liver copper accumulation, comprising detecting in a sample the presence or absence in the genome of the dog of one or more polymorphisms selected from (a) SNP ATP7a_Reg3_F_6 (SEQ ID NO:142) and (b) one or more polymorphisms in linkage disequilibrium with (a).

The invention also provides:

a database comprising information relating to SNP ATP7a_Reg3_F_6 (SEQ ID NO:142) and/or one or more polymorphisms in linkage disequilibrium thereof and their association with the protection of a dog from liver copper accumulation;

a method of determining the likelihood that a dog is protected from liver copper accumulation, the method comprising:
(a) inputting to a computer system data concerning the presence or absence in the genome of the dog of a polymorphism as defined herein;
(b) comparing the data to a computer database, which database comprises information relating to said polymorphisms and their association with the protection of a dog from, or susceptibility of a dog to, liver copper accumulation; and
(c) determining on the basis of the comparison the likelihood that the dog is protected from liver copper accumulation;

a computer program comprising program code means that, when executed on a computer system, instruct the computer system to perform a method of the invention;

a computer storage medium comprising the computer program of the invention and the database of the invention;

a computer system arranged to perform a method of the invention comprising:
(a) means for receiving data concerning the presence or absence in the genome of the dog of a polymorphism as defined herein;
(b) a database comprising information relating to said polymorphisms and/or one or more polymorphisms in linkage disequilibrium thereof and their association with the protection of a dog from, or susceptibility of a dog to, liver copper accumulation;
(c) a module for comparing the data with the database; and means for determining on the basis of said comparison the likelihood that the dog is protected from liver copper accumulation;

a method of determining the likelihood that a dog is protected from liver copper accumulation, comprising detecting the presence or absence in the genome of the dog of one or more polymorphisms selected from (a) SNP ATP7a_Reg3_F_6 (SEQ ID NO:142) and (b) one or more polymorphisms in linkage disequilibrium with (a);

use of a polymorphism as defined herein for determining the protection of a dog from liver copper accumulation; and a method of selecting a dog for producing offspring likely to be protected from liver copper accumulation comprising:
determining whether the genome of a candidate first dog comprises one or more polymorphisms indicative of protection from liver copper accumulation according to the invention; and thereby determining whether the candidate first dog is suitable for producing offspring likely to be protected from liver copper accumulation;
optionally, determining whether the genome of a second dog of the opposite sex to the first dog comprises one or more polymorphisms indicative of protection from liver copper accumulation according to the invention; and
optionally, mating the first dog with the second dog in order to produce offspring likely to be protected from liver copper accumulation.

Further, and surprisingly, the inventors found a foodstuff which is more effective in reducing hepatic copper concentration in Labrador Retrievers than the use of the drug penicillamine. This foodstuff is therefore useful in preventing liver copper accumulation in dogs of the Labrador Retriever breed and can be used for preventing a disease or condition associated with high liver copper such as chronic hepatitis, cirrhosis and liver failure.

Accordingly, the present invention also provides a foodstuff comprising copper at a concentration of from 4.5 to 12 mg/kg dry matter for use in a method of preventing a disease attributable to liver copper accumulation in a dog having genetic inheritance of the Labrador Retriever breed, preferably wherein the likelihood that the dog is protected from liver copper accumulation has been determined by a method of the invention.

The present invention further provides:
a method of preventing a disease attributable to liver copper accumulation in a dog having genetic inheritance of the Labrador Retriever breed, preferably wherein the likelihood that the dog is protected from liver copper accumulation has been determined by a method of the invention, the method comprising feeding the dog a foodstuff of the invention;

use of copper in the manufacture of a foodstuff for a dog having genetic inheritance of the Labrador Retriever breed, preferably wherein the likelihood that the dog is protected from liver copper accumulation has been determined by a method of the invention, wherein the foodstuff comprises copper at a concentration of from 4.5 to 12 mg/kg dry matter and is for use in preventing a disease attributable to liver copper accumulation in said dog;

a pack comprising a foodstuff having copper at a concentration of from 4.5 to 12 mg/kg dry matter and a zinc supplement for providing a concentration of at least 120 mg/kg dry matter for simultaneous, separate or sequential use in preventing a disease attributable to liver copper accumulation in a dog having genetic inheritance of the Labrador Retriever breed, preferably wherein the likelihood that the dog is protected from liver copper accumulation has been determined by a method of the invention; and a labelled foodstuff of the invention or labelled pack of the invention.

The progression along the x-axis from 1 to 2 demonstrates the penicillamine effect, whilst the progression from 2 to 3 demonstrates the food effect. The dotted line represents the normal level of hepatic copper for adult dogs.

Figure 4:
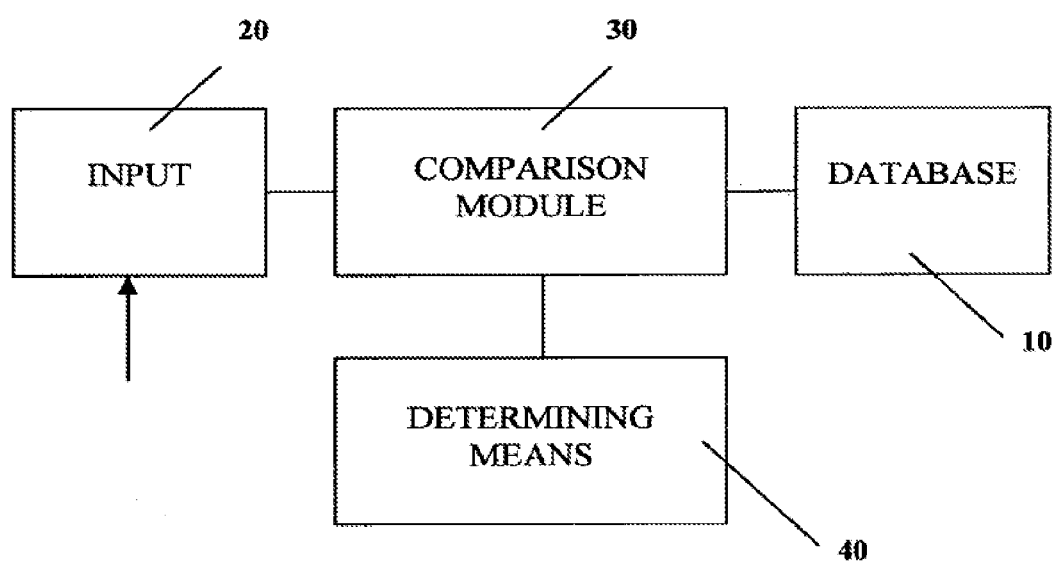

FIG. 4 illustrates schematically embodiments of functional components arranged to carry out the present invention.

Figure 5:
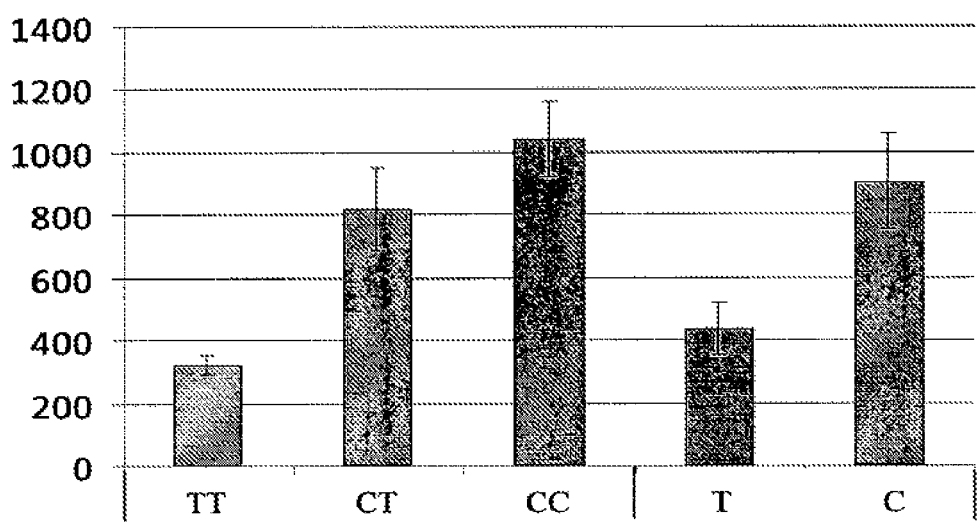

FIG. 5 depicts the average copper levels by gender and ATP7A genotype in Labrador Retrievers (data of Table VII). The y-axis is dry liver weight copper (mg/kg). The x-axis is ATP7A genotype: from left to right, the first three are for the female dogs in the study and the last two are for the male dogs in the study. Error bars are standard error.

Figure 6:
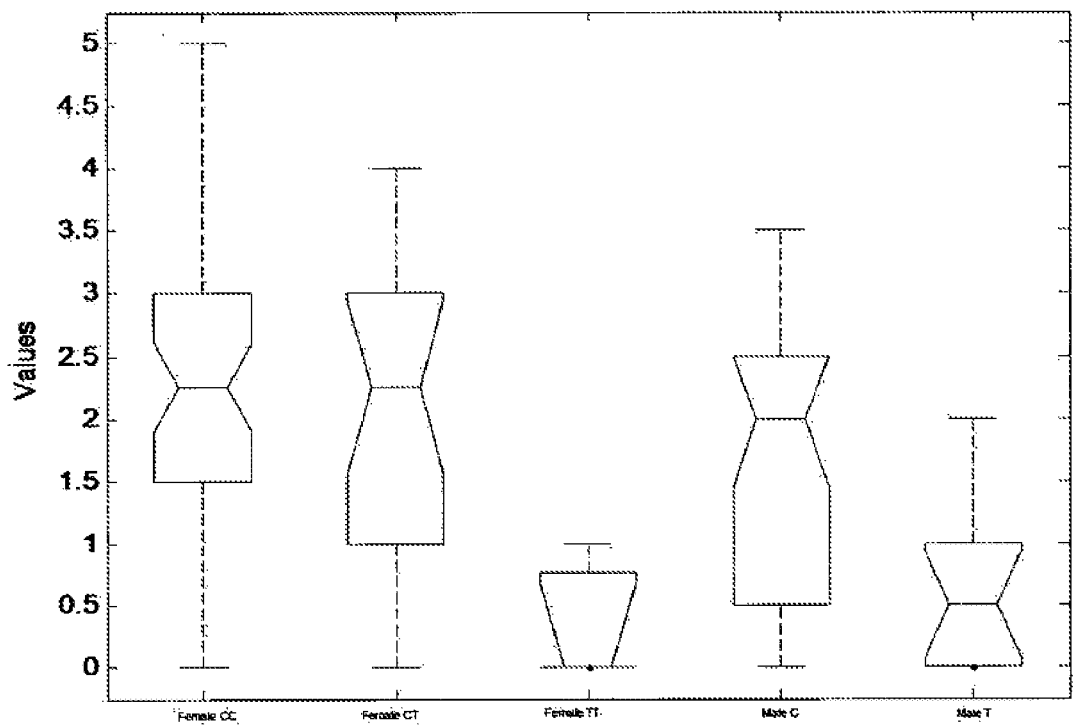

FIG. 6 is a box-plot of copper-histological scores by gender and ATP7A genotype in Labrador Retrievers (data of Table VII). The y-axis is the copper histological score values. The x-axis is ATP7A genotype: from left to right, the first three are for the female dogs in the study and the last two are for the male dogs in the study. The kruskal-walis p-value is 0.000396.

Figures 7A, 7B:
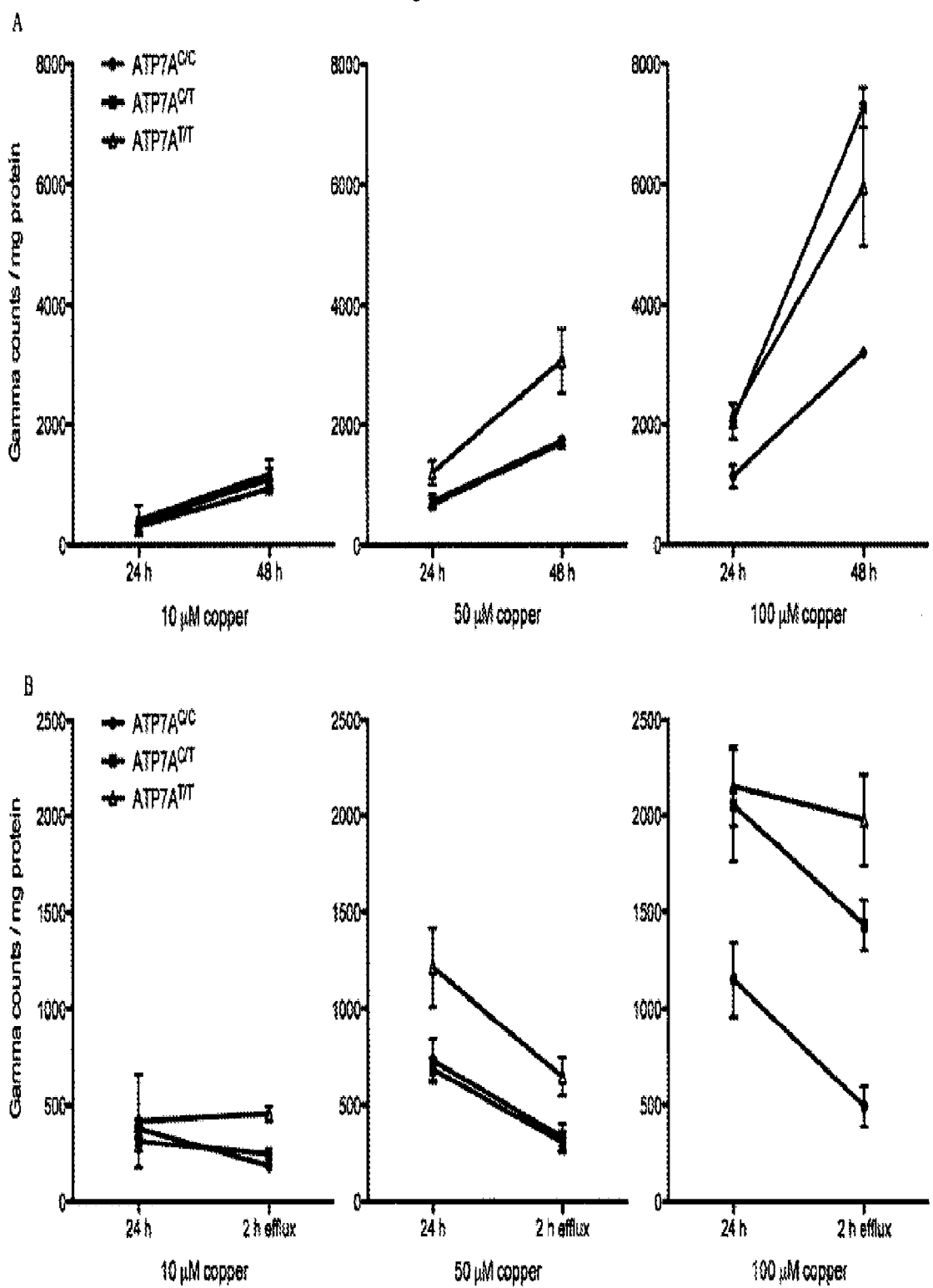

FIGS. 7A and 7B show copper isotope measurements in canine primary fibroblast cells. Copper isotope (64Cu) measurements in $ATP7A^{C/C}$, $ATP7A^{C/T}$ and $ATP7A^{T/T}$ cells after (A) 24 h or 48 h incubation with 10 μM, 50 μM and 100 μM 64Cu, or (B) 24 hrs incubation, followed by extensive washing and incubation in non copper isotope media for 2 h. Gamma-counts were corrected for cell culture conditions by means of a protein and MTS assay. Data points for 24 hr incubation represent the mean+/−SEM from two independent experiments performed in duplicate and expressed as counts per minute (cpm) of total cell protein. Other data points represent mean+/−SEM from one experiment in duplicate.

Figures 7C, 7D:
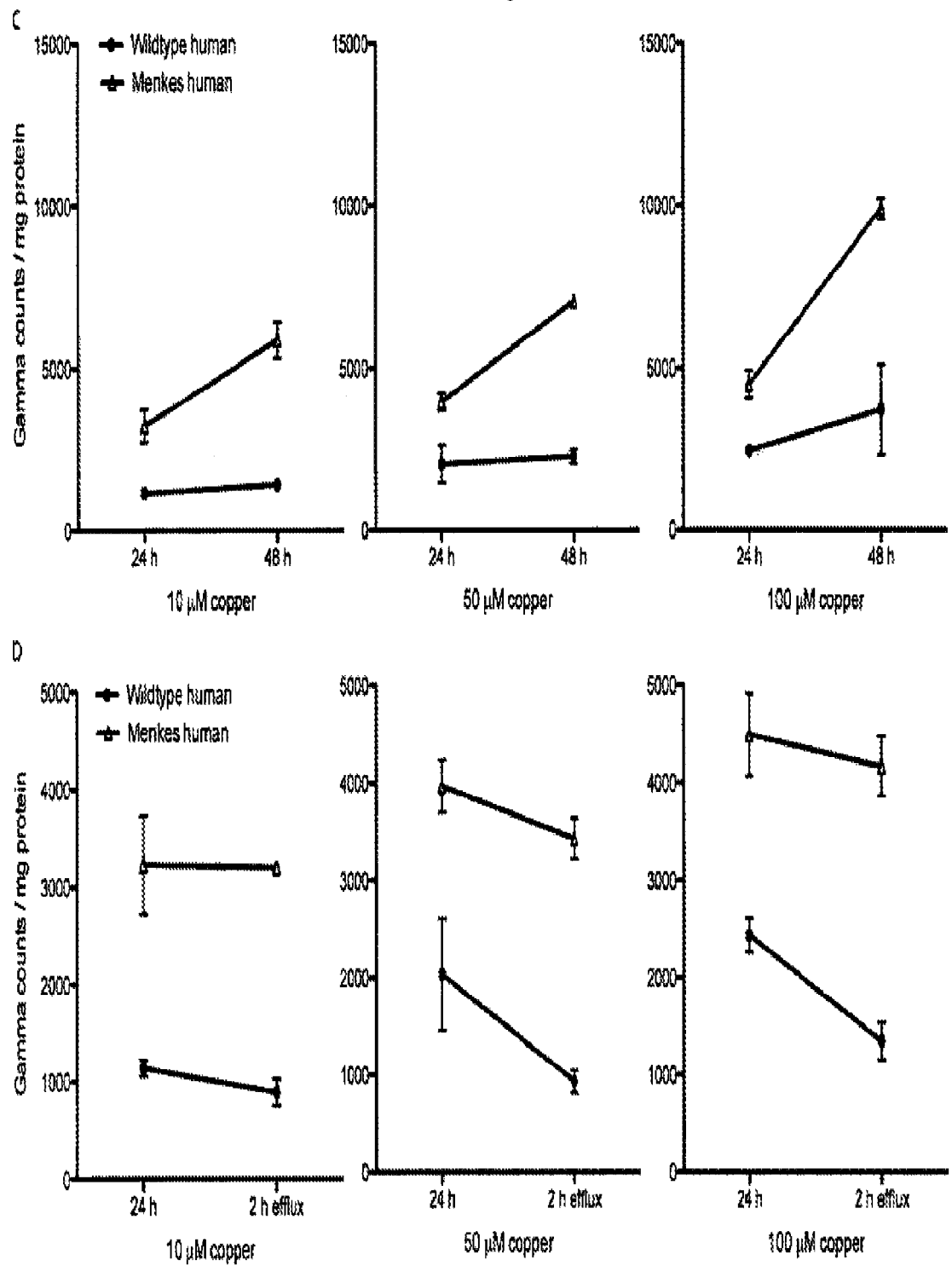

FIGS. 7C and 7D show copper isotope measurements in human primary fibroblast cells. Copper isotope (64Cu) measurements in primary fibroblast cells derived from a Menkes patient or a non Menkes patient (control), after (C) 24 h or 48 h incubation with 10 μM, 50 μM and 100 μM 64Cu, or (D) 24 hrs incubation, followed by extensive washing and incubation in non copper isotope media for 2 h. Gamma-counts were corrected for cell culture conditions by means of a protein assay. Data points are expressed as (A) and (B).

Figure 8:
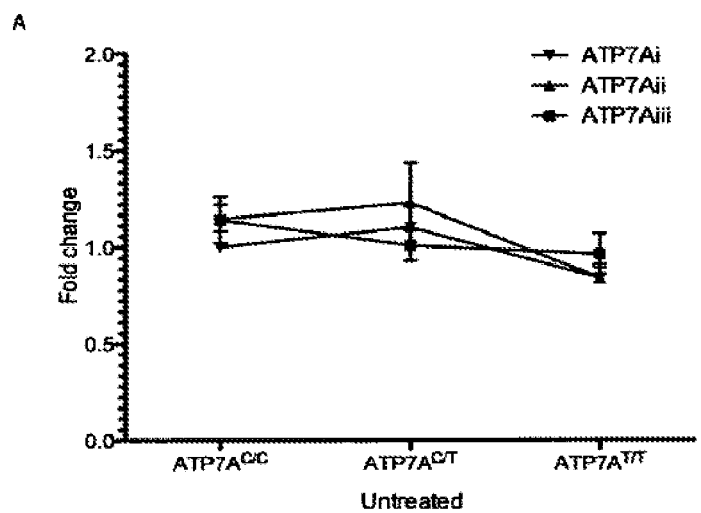
Figure 8:
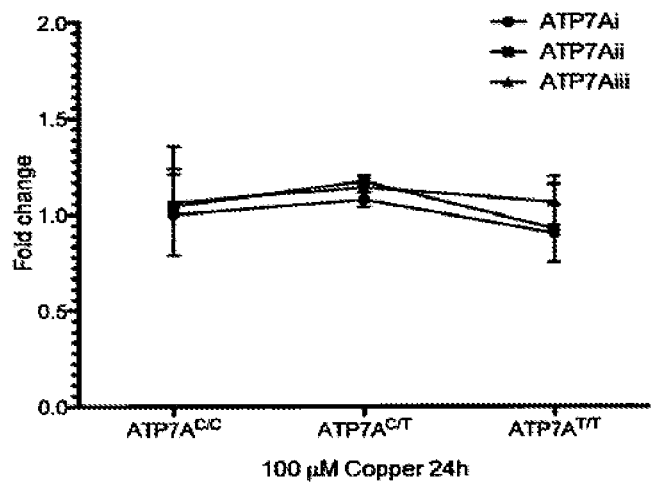
Figure 8:
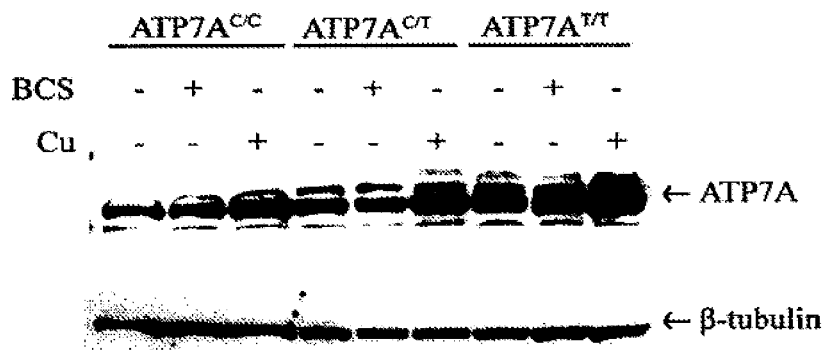

FIG. 8 shows gene expression levels of ATP7A in canine primary fibroblast cells. (A) $ATP7A^{C/C}$, $ATP7A^{C/T}$ and $ATP7A^{T/T}$ cells were untreated (top graph) or incubated in the presence of 100 μM copper for 24 h (bottom graph) prior to qPCR analysis of the 3' (ATP7Aiii) region, 5' (ATP7Aii) region or region overlapping the mutation (ATP7Ai). Data depicts mean+/−SD from two independent experiments performed in triplicate wells. (B) Western blot analysis of ATP7A expression. Cells were left untreated (−), incubated with 100 μM BCS, or 100 μM copper for 24 hrs. Samples were lysed and protein was subsequently resolved on a 12% SDS-PAGE gel and immunoblotted with chicken anti-ATP7A (1:2000 dilution) for 1 h. The membrane was then incubated with goat anti-chicken Ig HRP-conjugated antibody (1:10,000 dilution) for a further 1 h and then developed using ECL™ western blotting detection reagents. The membrane was stripped and re-probed with β-tubulin (1:20,000 dilution) to ensure equal loading. Arrows indicate expected full-length protein.

Figure 9:
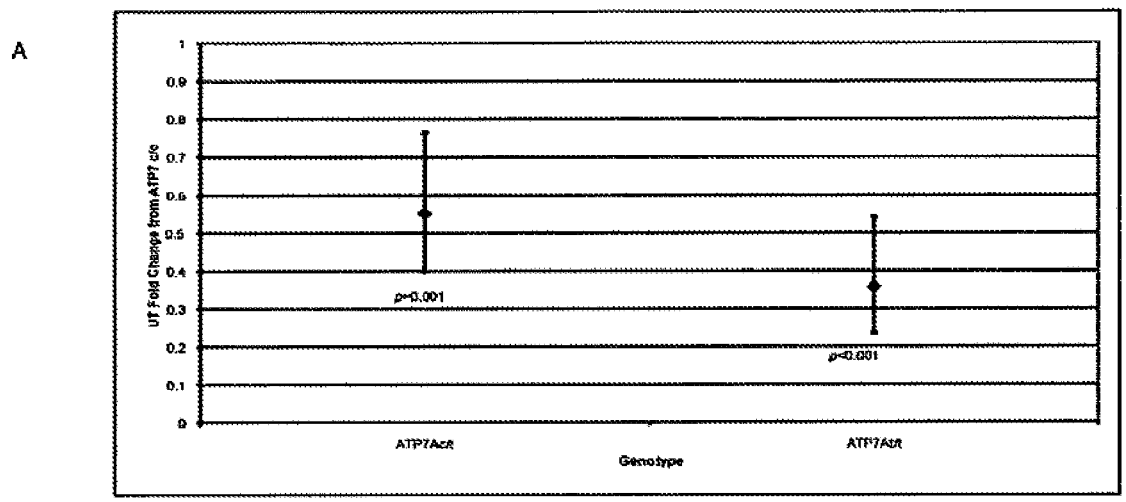
Figure 9:
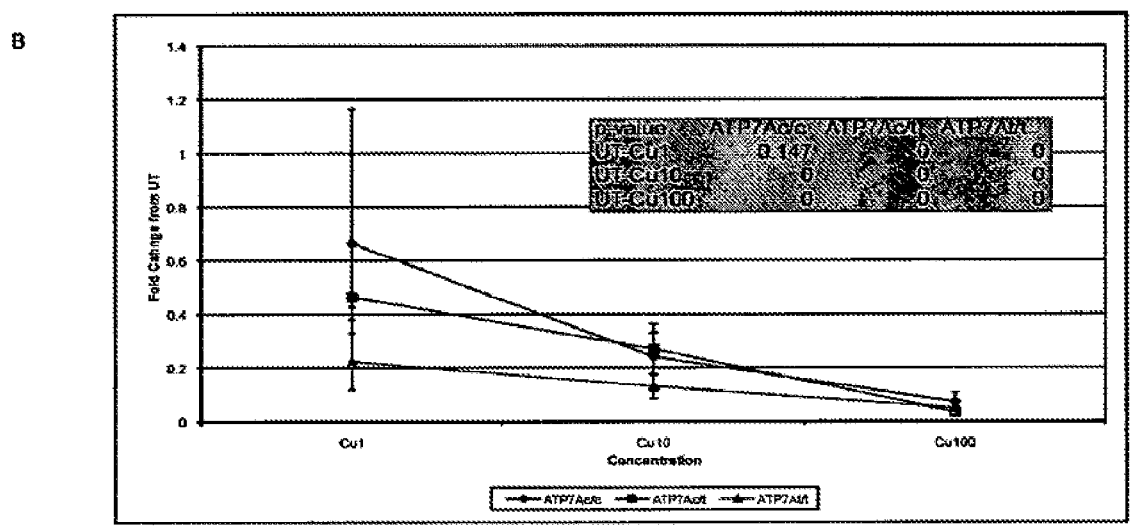
Figure 9:
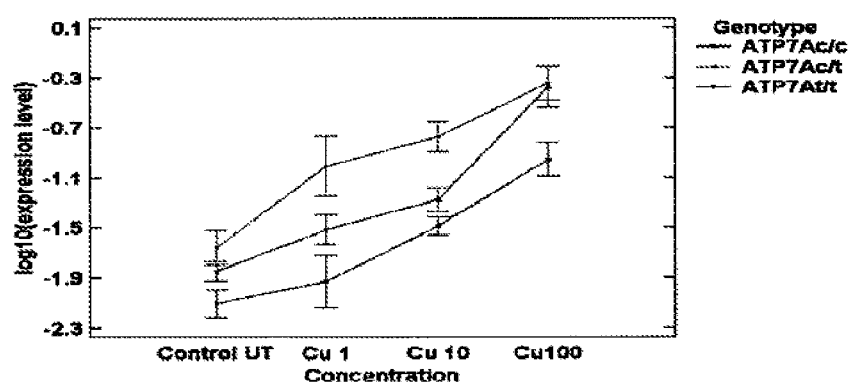

FIG. 9 provides the gene expression levels of metallothionein in canine primary fibroblast cells. $ATP7A^{C/C}$, $ATP7A^{C/T}$ and $ATP7A^{T/T}$ cells were incubated in the presence of 1, 10 or 100 μM copper or left untreated (UT) for 24 h and subjected to qPCR analysis of the metallothionein gene. FIG. 9(A) depicts fold change compared to UT $ATP7A^{C/C}$ with 95% confidence interval (CI), (B) depicts fold change compared to UT $ATP7A^{genotype}$ expression with 95% CI, and (C) depicts log 10 expression level with 95% confidence interval (CI). In (C), the top line in the graph is for genotype $ATP7A^{T/T}$, the middle line is for $ATP7A^{C/T}$, and the lower line is for $ATP7A^{C/C}$.

Figure 10:
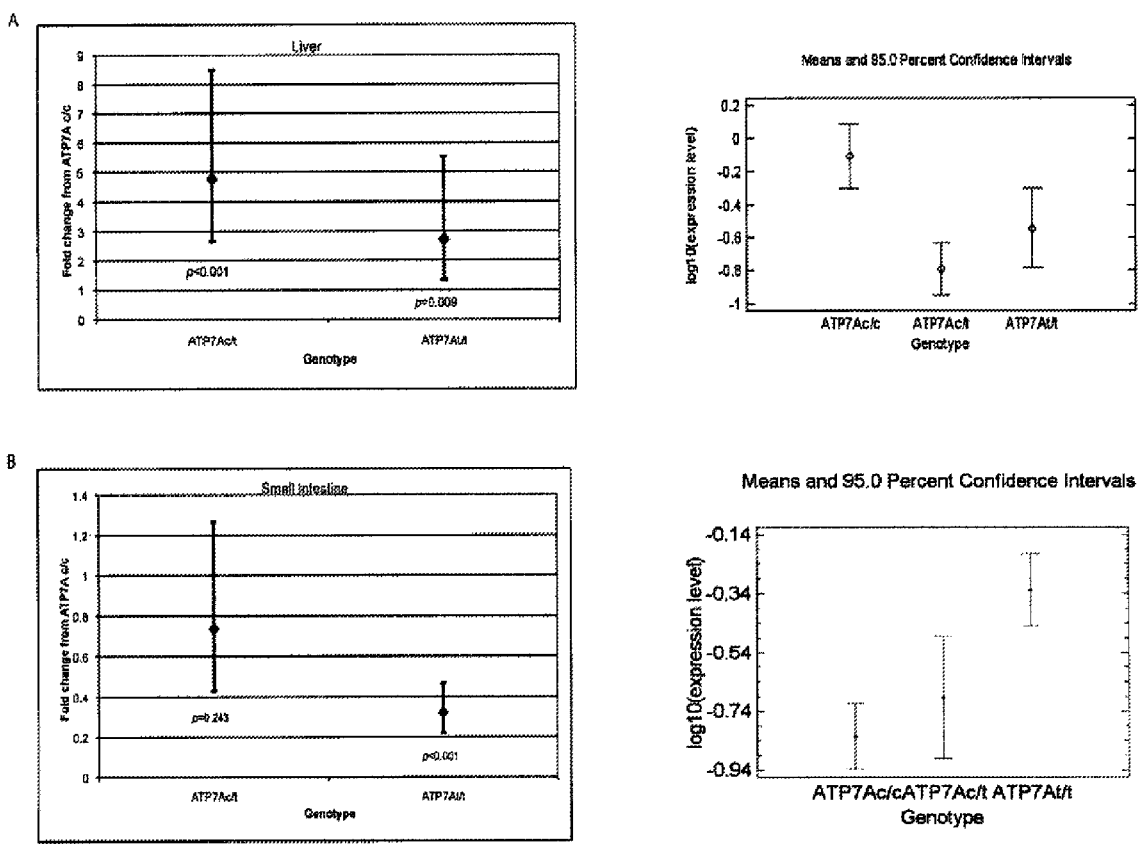

FIG. 10 illustrates gene expression levels of metallothionein in canine intestine and liver tissue. (A) Liver and (B) small intestine tissue was extracted from dogs expressing $ATP7A^{C/C}$, $ATP7A^{C/T}$ or $ATP7A^{T/T}$ ATP7A and subjected to qPCR analysis of the metallothionein gene. Data depicts mean of the log 10 expression level and 95% CI from 5 independent experiments (right panels) and fold change with 95% CI compared to $ATP7A^{C/C}$.

Figure 11:
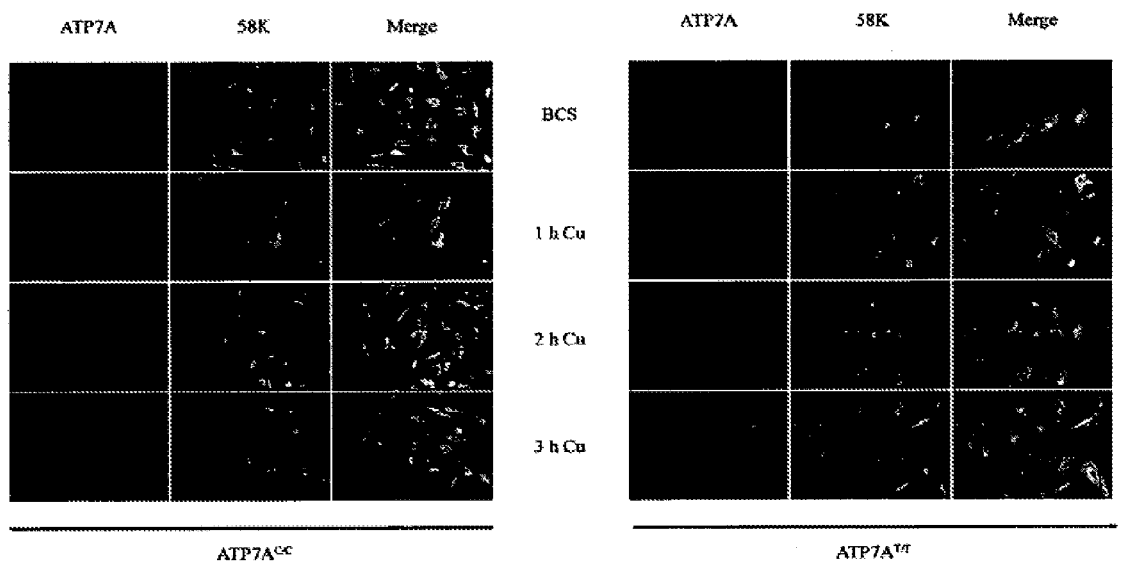

FIG. 11 is characterization of copper-mediated trafficking of ATP7A protein. $ATP7A^{C/C}$ (left panel) and $ATP7A^{T/T}$ (right panel) cells were grown on glass slides in the presence of 100 μM BCS for 18 h, prior to washing and incubation with 100 μM copper for 1, 2 or 3 h in the culture media. Cells were fixed, and stained with anti-ATP7A (first column in each panel) and anti-58K (second column in each panel) antibodies, and processed for triple label indirect microscopy prior to visualisation using epifluorescence microscopy. Images of ATP7A and 58K are merged to depict overlapping regions (third column in each panel).

BRIEF DESCRIPTION OF THE SEQUENCES

SEQ ID NOs: 1 to 143 show the polynucleotide sequences encompassing the SNPs of the invention.
SEQ ID NOs: 144 to 159 are primer sequences.

DETAILED DESCRIPTION OF THE INVENTION

Identifying Protection from or Susceptibility to Liver Copper Accumulation

Accumulation of copper in the liver leads to liver disease in a number of dog breeds, including the Labrador Retriever, Doberman Pinscher, German Shepherd, Keeshond, Cocker Spaniel, West Highland White Terrier, Bedlington Terrier, and Skye Terrier. The mean copper concentration in the liver of normal dogs of any breed is 200 to 400 mg/kg on a dry weight basis, although newborns generally have higher liver copper concentrations. The amount of copper in the liver of a dog may be measured by biopsy.

A dog that is protected from liver copper accumulation has a low risk or likelihood of accumulating liver copper such that its liver copper concentration is less likely to reach a level above 400 mg/kg on a dry weight basis. The liver copper concentration of a dog that is protected from liver copper accumulation will be below 600 mg/kg, for example below 500 mg/kg, below 400 mg/kg, or below 300 mg/kg. Determining the likelihood that a dog is protected from liver copper accumulation according to the invention involves determining the likelihood that the dog will accumulate liver copper to a level below 600 mg/kg, for example below 500 mg/kg, below 400 mg/kg, or below 300 mg/kg.

A dog that is susceptible to liver copper accumulation has a tendency to accumulate copper such that its liver copper concentration reaches a level above 400 mg/kg on a dry weight basis. Determining the risk or likelihood that a dog is susceptible to liver copper accumulation involves determining the risk or likelihood that the dog will accumulate liver copper to a level above 400 mg/kg, for example above above 600 mg/kg, above 800 mg/kg, above 1000 mg/kg, above 1500 mg/kg, above 2000 mg/kg, above 5000 mg/kg, or above 10000 mg/kg.

The accumulation of liver copper may be assessed by histochemistry. For example, liver copper concentration may be semiquantitatively assessed by histochemistry using the rubeanic acid staining technique for evaluation of copper distribution as previously described (Van den Ingh et al., (1988) Vet Q 10: 84-89). The concentration may be graded in a scale of 0 to 5 as follows: 0=no copper present; 1=solitary liver cells and/or reticulohistiocytic (RHS) cells containing some copper positive granules; 2=small groups of liver cells and/or RHS cells containing small to moderate numbers of copper positive granules; 3=larger groups or areas of liver cells and/or RHS cells containing moderate numbers of copper positive granules; 4=large areas of liver cells and/or RHS cells with many copper positive granules; and 5=diffuse presence of liver cells and/or RHS cells with many copper positive granules. According to this grading system, copper scores above 2 are abnormal.

Therefore determining the likelihood that a dog is protected from liver copper accumulation according to the invention can involve determining the likelihood that the dog would be given a score of less than or equal to 3, for example less than or equal to 2.5, 2, 1.5, or less than or equal to 1, using the grading system described in Van den Ingh et al. Determining the risk or likelihood that a dog is susceptible to liver copper accumulation can involve determining the risk or likelihood that the dog would be given a score of greater than or equal to 2, for example greater than or equal to 2.5, 3, 3.5, or greater than or equal to 4, using the grading system described in Van den Ingh et al.

The likelihood of protection or risk of susceptibility may for example be expressed as a risk factor, percentage or probability. It may be possible to determine whether or not a dog will accumulate copper to the levels described above. For example, the method of determining the likelihood of protection from liver copper accumulation may comprise determining whether or not a dog will accumulate copper to a level above 400 mg/kg.

Accumulation of liver copper to a level above 400 mg/kg is associated with liver disease and may ultimately lead to liver failure. Therefore, determining whether the genome of a dog comprises one or more polymorphisms indicative of protection from liver copper accumulation indicates that the dog is less likely to develop a disease or condition attributable to liver copper accumulation such as chronic hepatitis, cirrhosis and liver failure. Conversely, determining whether the genome of a dog comprises one or more polymorphisms indicative of susceptibility to liver copper accumulation indicates the susceptibility of the dog to such a disease or condition. Therefore, the invention provides a method of testing for the susceptibility of a dog to, or the likelihood of protection of a dog from, a disease associated with liver copper accumulation, such as chronic hepatitis, cirrhosis and liver failure.

Polymorphisms and Indication of Susceptibility to, or Protection from, Copper Accumulation The inventors have surprisingly discovered a polymorphism affecting the protein sequence of ATP7A that is indicative of protection from liver copper accumulation, as opposed to being indicative of susceptibility to liver copper accumulation (Examples 2 to 5). The polymorphism changes the protein sequence at amino acid 328 of the ATP7A gene from a Threonine to an Isoleucine. In vitro experiments have determined that the mutation has a large functional effect on the protein (Example 5). The experiments have revealed that the rate of accumulation of copper is greater in cells expressing the mutated form of the protein; accumulation is greater during copper exposure and release is slower after copper exposure. In addition, intracellular ATP7A movement in response to copper exposure is altered in cells carrying the mutation. There is also increased expression of a copper transport protein in cells carrying the mutation. Expression levels of ATP7A are not altered between cells carrying the two forms. The ATP7A coding mutation therefore has a significant effect on the function of the protein.

The present invention therefore relates to a method of determining whether the genome of a dog comprises one or more polymorphisms indicative of protection from liver copper accumulation. In particular, the present invention provides a method of determining the likelihood that a dog is protected from liver copper accumulation comprising detecting the presence or absence in the genome of the dog of one or more polymorphisms selected from (a) SNP ATP7a_Reg3_F_6 (position 102 of SEQ ID NO:142) and (b) one or more polymorphisms in linkage disequilibrium with (a).

The phrase "detecting the presence or absence of a polymorphism" typically means determining whether a polymorphism is present in the genome of the dog. Polymorphisms include Single Nucleotide Polymorphisms (SNP), microsatellite polymorphisms, insertion polymorphisms and deletion polymorphisms. Preferably the polymorphism is a SNP. Detecting the presence or absence of a SNP means genotyping the SNP or typing the nucleotide(s) present in the genome of the dog for the SNP. Typically, the nucleotide present at the same position on both homologous chromosomes will be determined. A dog may therefore be determined to be homozygous for a first allele, heterozygous or homozygous for a second allele of the SNP.

Determining a phenotype of an individual, such as the susceptibility of the individual to, or the protection of the individual from, a disease or condition, is not limited to the detection of a polymorphism that is causal for the disease or condition. In genetic mapping studies, genetic variation at a set of marker loci in a sample of individuals is tested for association with a given phenotype. If such an association is found between a particular marker locus and the phenotype, it suggests that either the variation at that marker locus affects the phenotype of interest, or that the variation at that marker locus is in linkage disequilibrium with the true phenotype-related locus, which was not genotyped. In the case of a group of polymorphisms that are in linkage disequilibrium with each other, knowledge of the existence of all such polymorphisms in a particular individual generally provides redundant information. Thus, when determining whether the genome of a dog comprises one or more polymorphisms indicative of susceptibility to, or protection from, liver copper accumulation or to copper-associated liver disease, it is necessary to detect only one polymorphism of such a group of polymorphisms.

As a result of linkage disequilibrium, a polymorphism that is not a functional susceptibility/protective polymorphism, but is in linkage disequilibrium with a functional polymorphism, may act as a marker indicating the presence of the functional polymorphism. A polymorphism that is in linkage disequilibrium with a polymorphism of the invention is indicative of susceptibility to, or protection from, liver copper accumulation.

Accordingly, any one of the polymorphic positions as defined herein may be typed directly, in other words by determining the nucleotide present at that position, or indirectly, for example by determining the nucleotide present at another polymorphic position that is in linkage disequilibrium with said polymorphic position.

Linkage disequilibrium is the non-random gametic association of alleles at different loci in a population. Polymorphisms that have a tendency to be inherited together instead of being inherited independently by random assortment are in linkage disequilibrium. Polymorphisms are randomly assorted or inherited independently of each other if the frequency of the two polymorphisms together is the product of the frequencies of the two polymorphisms individually. For example, if two polymorphisms at different polymorphic sites are present in 50% of the chromosomes in a population, then they would be said to assort randomly if the two alleles are present together on 25% of the chromosomes in the population. A higher percentage would mean that the two alleles are linked. It follows that a first polymorphism is in linkage disequilibrium with a second polymorphism if the frequency of the two polymorphisms together is greater than the product of the frequencies of the two polymorphisms individually in a population. Preferably, a first polymorphism is in linkage disequilibrium with a second polymorphism if the frequency of the two polymorphisms together is more that 10% greater, for example more than 30%, more than 50% or more than 70% greater, than the product of the frequencies of the two polymorphisms individually.

Research has shown that linkage disequilibrium is extensive in dogs (Extensive and breed-specific linkage disequilibrium in *Canis familiaris*, Sutter et al., Genome Research 14: 2388-2396). Polymorphisms which are in linkage disequilibrium are often in close physical proximity, which is why they are co-inherited. Polymorphisms which are in linkage disequilibrium with the polymorphisms mentioned herein are located on the same chromosome. Polymorphisms which are in linkage disequilibrium in dogs are typically within 5 mb, preferably within 2 mb, within 1 mb, within 700 kb, within 600 kb, within 500 kb, within 400 kb, within 200 kb, within 100 kb, within 50 kb, within 10 kb, within 5 kb, within 1 kb, within 500 bp, within 100 bp, within 50 bp or within 10 bp of the polymorphism.

It would be within the capability of the skilled person to use routine techniques to identify polymorphisms that are in linkage disequilibrium with any one of the polymorphic positions as defined herein. Once a potential polymorphism has been selected, the skilled person can readily determine whether this polymorphism, and what version or allele of the polymorphism, is significantly correlated with any of the polymorphisms defined herein.

In more detail, to determine whether a polymorphism is in linkage disequilibrium with any one of the polymorphisms defined herein, the skilled person should genotype the candidate polymorphism and one or more of the polymorphisms defined herein in a panel of dogs. The size of the panel should be adequate enough to achieve a statistically significant result. Typically, samples from at least 100, preferably at least 150 or at least 200, different dogs should be genotyped. The dogs in the panel may be of any breed, but typically will have the same or similar genetic breed background. Once the polymorphisms have been genotyped in the panel of dogs, linkage disequilibrium between one or more pairs of polymorphisms can be measured using any one of a number of readily available statistical packages. An example of a free software package is Haploview (Haploview: analysis and visualisation of LD and haplotype maps, Barrett et al, 2005, Bioinformatics, 21(2): 263-265), downloadable at http://www.broadinstitute.org/haploview/haploview.

A measure of linkage disequilibrium is D'. A range of 0.5 to 1 for D' is indicative of a pair of polymorphisms being in linkage disequilibrium, with 1 indicating the most significant linkage disequilibrium. Therefore if D' is found to be from 0.5 to 1, preferably from 0.6 to 1, 0.7 to 1, from 0.8 to 1, from 0.85 to 1, from 0.9 to 1, from 0.95 to 1 or most preferably 1, for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, D', is greater than or equal to 0.9.

Another measure of linkage disequilibrium is R-squared, where R is the correlation coefficient. R-squared, which is also known as the 'Coefficient of determination', is the fraction of the variance in the genotypes of the first polymorphism which is accounted for in the genotypes of the second polymorphism. Therefore an R-squared of 0.5 for a candidate polymorphism and a specific polymorphism defined herein would mean that the candidate polymorphism accounts for 50% of the variance in the specific polymorphism. R-squared is producible from standard statistical packages such as Haploview. Typically, an R-squared of 0.25 or greater (R of >0.5 or <−0.5) is considered a large correlation. Therefore if R-squared is found to be 0.5 or more, preferably 0.75 or more, 0.8 or more, 0.85 or more, 0.9 or more, or 0.95 or more for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, R-squared, is greater than or equal to 0.85.

Once a polymorphism has been identified as being in linkage disequilibrium and therefore correlated with a polymorphism defined herein, the skilled person can readily determine which version of the polymorphism, i.e. which allele, is associated with susceptibility to or protection from liver copper accumulation. This could be achieved by phenotyping a panel of dogs for liver copper accumulation and classifying the dogs in terms of the level of liver copper accumulation. The panel of dogs are then genotyped for the polymorphism of interest. The genotypes are then correlated with the level of liver copper in order to determine the association of the genotypes with liver copper level and thereby determine which allele is associated with susceptibility to or protection from liver copper accumulation.

The polymorphisms of the invention that are indicative of protection from liver copper accumulation are the SNP identified in Table VI (ATP7a_Reg3_F_6 (position 102 of SEQ ID NO:142)) and one or more polymorphisms in linkage disequilibrium with this SNP. Therefore, the method of the invention comprises detecting the presence or absence of one or more polymorphisms selected from (a) SNP ATP7a_Reg3_F_6 (SEQ ID NO:142) and (b) one or more polymorphisms in linkage disequilibrium with (a). Preferably, the method comprises determining the presence or absence of the SNP identified in Table VI (ATP7a_Reg3_F_6 (SEQ ID NO: 142)), i.e. polymorphism (a).

Any number and any combination of polymorphisms may be detected to carry out the invention. Preferably at least 2 polymorphisms are detected. Preferably 2 to 5, 3 to 8 or 5 to 10 polymorphisms are detected.

The DNA of a dog may be typed at the respective positions of:
(i) a polymorphism (a);
(ii) one or more polymorphisms (b); or
(iii) a polymorphism (a) and one or more polymorphisms (b).

A preferred method comprises detecting the presence or absence of (a) SNP ATP7a_Reg3_F_6 (SEQ ID NO:142) and at least one polymorphism (b) in linkage disequilibrium with said polymorphism (a).

In a preferred method of the invention, the polymorphism in linkage disequilibrium with said polymorphism (a) is a SNP. Preferably the polymorphism is any polymorphism in or in the region of the ATP7A gene of the dog that is indicative of protection from liver copper accumulation. An example of a SNP in linkage disequilibrium with polymorphism (a) is SNP ATP7a_Reg16_F_42 (position 68 of SEQ ID NO:143). This SNP was found to be in linkage disequilibrium with SNP ATP7a_Reg3_F_6 (SEQ ID NO:142) and indicative of protection from liver copper accumulation (Example 4). Therefore this SNP can either be used on its own, or in combination with polymorphism (a), to determine the likelihood that a dog is protected from liver copper accumulation. Accordingly, the method of determining the likelihood that a dog is protected from liver copper accumulation may comprise detecting the presence or absence in the genome of the dog of one or more polymorphisms selected from (a) SNP ATP7a_Reg3_F_6 (SEQ ID NO:142), (b) SNP ATP7a_Reg16_F_42 (SEQ ID NO:143) and one or more polymorphisms in linkage disequilibrium with (a) and/or (b). A preferred method comprises detecting the presence or absence (a) SNP ATP7a_Reg3_F_6 (SEQ ID NO:142) and (b) SNP ATP7a_Reg16_F_42 (SEQ ID NO:143).

The T allele for the ATP7A SNP identified in Table VI (ATP7a_Reg3_F_6 (SEQ ID NO: 142) has been determined by the inventors to be indicative of protection from copper accumulation. This SNP is located on the X chromosome. Dogs that are homozygous (in the case of female dogs) or hemizygous (in the case of male dogs) for the T allele are protected from copper accumulation. Dogs that have the C allele appear to not be protected from copper accumulation. Therefore, a preferred method of the invention comprises determining the presence or absence of the T allele for the SNP identified in Table VI (ATP7a_Reg3_F_6 (SEQ ID NO: 142)). Accordingly, a preferred method of the invention comprises detecting the presence or absence of a TT or TC genotype at ATP7a_Reg3_F_6 (SNP 142) and thereby determining whether the genome of the dog comprises a polymorphism indicative of protection from liver copper accumulation.

In view of the fact that the ATP7A SNP identified in Table VI is located on the X chromosome and the protective effect is recessive, male dogs are more likely to have the protective phenotype. The method of the invention may therefore comprise determining the sex of the dog. Given that male dogs in general are less susceptible to copper accumulation compared with female dogs, the ATP7A SNP ((ATP7a_Reg3_F_6 (SEQ ID NO: 142)) is particularly useful for dogs of all breeds including dogs of unknown breed or mixed breed (mongrel). Example 3 also provides evidence that the method of the invention is applicable for dogs of all breeds and in all geographical locations. The method of the invention may therefore comprise determining whether the genome of a mixed or crossbred dog, or a mongrel or out-bred dog comprises one or more polymorphisms in the ATP7A gene that are indicative of protection from liver copper accumulation or one or more polymorphisms in linkage disequilibrium therewith.

For SNP ATP7a_Reg16_F_42 (SEQ ID NO: 143), which has been found to be in linkage disequilibrium with SNP ATP7a_Reg3_F_6 (SEQ ID NO: 142), the T allele has been determined by the inventors to be indicative of protection from copper accumulation. As explained above, the ATP7A gene and therefore this SNP is located on the X chromosome.

Dogs that are homozygous (in the case of female dogs) or hemizygous (in the case of male dogs) for the T allele are protected from copper accumulation. Dogs that have the C allele appear to not be protected from copper accumulation. Therefore, a preferred method of the invention comprises determining the presence or absence of the T allele for the SNP identified in Table X (ATP7a_Reg16_F_42 (SEQ ID NO: 143). Accordingly, a preferred method of the invention comprises detecting the presence or absence of a TT or TC genotype at (ATP7a_Reg16_F_42 (SEQ ID NO: 143) and thereby determining whether the genome of the dog comprises a polymorphism indicative of protection from liver copper accumulation.

The inventors have previously discovered that polymorphisms in or in the region of the canine GOLGA5, ATP7A and UBL5 genes are indicative of susceptibility to liver copper accumulation in dogs (Examples 1 to 2). Therefore these polymorphisms could be used in combination with the polymorphisms of the invention to provide an enhanced genetic test for determining the risk or likelihood that a dog is susceptible to or protected from liver copper accumulation. The method of the invention may therefore comprise determining the presence or absence of a combination of SNPs that are indicative of susceptibility to, and protection from, liver copper accumulation. DNA from the dog may be typed at one or more SNPs indicative of susceptibility to liver copper accumulation and typed at one or more SNPs indicative of protection from liver copper accumulation. The presence of one or more "susceptibility" SNPs in combination with the absence of one or more "protective" SNPs indicates that the dog is susceptible to liver copper accumulation. The presence of one or more "protective" SNPs in combination with the absence of one or more "susceptibility" SNPs indicates that the dog is protected from liver copper accumulation.

A polymorphism of the invention that is indicative of susceptibility to liver copper accumulation may be present in any one of the GOLGA5, ATP7A or UBL5 genes or may not be present within any one of those genes but is in linkage disequilibrium with a polymorphism in any one of those genes. The invention may therefore further comprise detecting the presence or absence of (c) a polymorphism in the GOLGA5, ATP7A or UBL5 gene of the dog that is indicative of susceptibility to liver copper accumulation and/or (d) a polymorphism in linkage disequilibrium with a said polymorphism (c). Any number and any combination of polymorphisms may be detected to carry out the invention. Preferably at least 2 polymorphisms are detected. Preferably 2 to 5, 3 to 8 or 5 to 10 polymorphisms are detected.

Therefore, the DNA of a dog may be typed at the respective positions of (i) polymorphism (a) and/or (ii) one or more polymorphisms (b). Additionally, the DNA of the dog may be typed at the respective positions of:

(iii) two or more polymorphisms (c);
(iv) two or more polymorphisms (d); or
(v) one or more polymorphisms (c) and one or more polymorphisms (d).

When there are two polymorphisms (c), each polymorphism may be in a separate one of the GOLGA5, ATP7A and UBL5 genes or in just one of those genes. When there are three or more polymorphisms (c), for example 3 to 10 such polymorphisms, the polymorphisms may be in the same gene, in two of the genes or in all three genes.

Similarly when there are two polymorphisms (d), each polymorphism may be in linkage disequilibrium with a polymorphism in a separate one of the GOLGA5, ATP7A and UBL5 genes or in just one of those genes. When there are three or more polymorphisms (d), for example 3 to 10 such polymorphisms, the polymorphisms may be in linkage disequilibrium with a polymorphism in the same gene, in two of the genes or in all three genes.

A preferred method comprises detecting the presence or absence of at least one polymorphism (c) in the GOLGA5, ATP7A or UBL5 gene of the dog that is indicative of susceptibility to liver copper accumulation and at least one polymorphism (d) in linkage disequilibrium with a said polymorphism (c).

In a preferred method of the invention, the polymorphism indicative of susceptibility is a SNP. The SNP may be any SNP in or in the region of the GOLGA5, ATP7A or UBL5 gene of the dog that is indicative of susceptibility to liver copper accumulation and/or a SNP that is in linkage disequilibrium thereof.

When the method comprises determining whether the genome of a dog comprises one or more polymorphisms indicative of susceptibility to liver copper accumulation, preferably the SNP is selected from a SNP identified in Table III, Table IV and Table V. In Tables III and IV each SNP is located at position 61 in the sequence. The first and second alleles are provided for each SNP at that location ([first/second]). In Table V, the first and second alleles for each SNP are also indicated. Any number of the SNPs may be used from Tables III, IV and V and in any combination. The SNPs may be combined with a different type of polymorphism.

Preferably, when the method comprises determining whether the genome of a dog comprises one or more polymorphisms indicative of susceptibility to liver copper accumulation, the method comprises detecting the presence or absence of one or more SNPs selected from the SNPs in Table III and Table V and/or one or more SNPs in linkage disequilibrium thereof. Therefore preferably the one or more SNPs are selected from BICF2P506595 (position 61 of SEQ ID NO:1), BICF2P772765 (position 61 of SEQ ID NO:2), BICF2S2333187 (position 61 of SEQ ID NO:3), BICF2P1324008 (position 61 of SEQ ID NO:4), BICF2P591872 (position 61 of SEQ ID NO:5), ATP7a_Reg4_F_9 (position 164 of SEQ ID NO: 131), UBL5_Reg1F_16 (position 97 of SEQ ID NO: 132), golga5_Reg1_24 (position 70 of SEQ ID NO: 133), golga5_26 (position 88 of SEQ ID NO: 134), golga5_27 (position 104 of SEQ ID NO: 135), golga5_28 (position 139 of SEQ ID NO: 136), golga5_29 (position 128 of SEQ ID NO: 137), golga5_30 (position 95 of SEQ ID NO: 138), golga5_31 (position 106 of SEQ ID NO: 139), atp7areg17_32 (position 95 of SEQ ID NO: 140), atp7areg17_33 (position 90 of SEQ ID NO: 141) and one or more SNPs in linkage disequilibrium thereof. Accordingly, any of these 16 SNPs or any SNPs that are in linkage disequilibrium with any if these 16 SNPs may be typed. Preferably at least 2 of these 16 SNPs or SNPs in linkage disequilibrium are typed.

More preferably, when the method comprises determining whether the genome of a dog comprises one or more polymorphisms indicative of susceptibility to liver copper accumulation, the method comprises detecting the presence or absence of one or more SNPs selected from the SNPs in Table III. Accordingly, any of these 5 SNPs or any SNPs that are in linkage disequilibrium with any of these 5 SNPs may be typed. Preferably at least 2 of these 5 SNPs or SNPs in linkage disequilibrium are typed. More preferably all 5 positions are typed. Preferably therefore, the nucleotide(s) that are typed are selected from positions equivalent to:

position 61 of SEQ ID NO: 1 (BICF2P506595, SNP1);
position 61 of SEQ ID NO: 2 (BICF2P772765, SNP 2);
position 61 of SEQ ID NO: 3 (BICF2S2333187, SNP 3);
position 61 of SEQ ID NO: 4 (BICF2P1324008, SNP 4);
position 61 of SEQ ID NO: 5 (BICF2P591872, SNP 5); or any positions which are in linkage disequilibrium with any one of these positions. Preferably, the method comprises detecting the presence or absence of the SNPs BICF2P506595 (SEQ ID NO:1), BICF2P772765 (SEQ ID NO:2), BICF2S2333187 (SEQ ID NO:3), BICF2P1324008 (SEQ ID NO:4), and BICF2P591872 (SEQ ID NO:5).

SNP 1 is located within an intron of the GOLGA5 gene. SNPs 2, 3 and 4 are located in the region of the UBL5 gene. SNP 5 is located in the region of the ATP7A gene. The detection method of the invention therefore relates to any SNP that lies within or in the region of one or more of these genes (in coding regions or otherwise), or any other SNP that is in linkage disequilibrium.

Example 1 demonstrates the use of these SNPs to establish a Boolean model of susceptibility to copper accumulation. Table I represents the binary conditions of alleles at three genomic locations. The binary values are indicative of a dog having alleles that are indicative of susceptibility to copper accumulation ("bad" alleles). For instance 000 represents not having any of the three bad alleles. 111 represents having all three bad alleles. The Xs are unused alleles at that gene. The lines 1xx and 0xx show the power that a one gene test only using the SNP in the GOLGA5 gene would have.

The A allele for SNP BICF2P506595 (SNP 1) has been determined by the inventors to be indicative of susceptibility to liver copper accumulation. Dogs that are homozygous for the A allele are susceptible to liver copper accumulation. Therefore, a preferred method of the invention comprises determining the presence or absence of the A allele for SNP BICF2P506595 and thereby determining whether the genome of the dog comprises a polymorphism indicative of susceptibility to liver copper accumulation. A more preferred method comprises detecting the presence or absence of the AA genotype for SNP BICF2P506595.

The G allele for SNP BICF2P772765 (SNP 2) has been determined by the inventors to be indicative of susceptibility to liver copper accumulation. Dogs that are homozygous for the G allele are susceptible to liver copper accumulation. Therefore, a preferred method of the invention comprises determining the presence or absence of the G allele for SNP BICF2P772765 and thereby determining whether the genome of the dog comprises a polymorphism indicative of susceptibility to liver copper accumulation. A more preferred method comprises detecting the presence or absence of the GG genotype for SNP BICF2P772765.

The C allele for SNP BICF2S2333187 (SNP 3) has been determined by the inventors to be indicative of susceptibility to liver copper accumulation. Dogs that are homozygous for the C allele are susceptible to liver copper accumulation. Therefore, a preferred method of the invention comprises determining the presence or absence of the C allele for SNP BICF2S2333187 and thereby determining whether the genome of the dog comprises a polymorphism indicative of susceptibility to liver copper accumulation. A more preferred method comprises detecting the presence or absence of the CC genotype for SNP BICF2S2333187.

The G allele for SNP BICF2P1324008 (SNP 4) has been determined by the inventors to be indicative of susceptibility to liver copper accumulation. Dogs that are homozygous for the G allele are susceptible to liver copper accumulation. Therefore, a preferred method of the invention comprises determining the presence or absence of the G allele for SNP BICF2P1324008 and thereby determining whether the genome of the dog comprises a polymorphism indicative of susceptibility to liver copper accumulation. A more preferred method comprises detecting the presence or absence of the GG genotype for SNP BICF2P1324008.

The A allele for SNP BICF2P591872 (SNP 5) has been determined by the inventors to be indicative of susceptibility to liver copper accumulation. Dogs that are homozygous or heterozygous for the A allele are susceptible to liver copper accumulation. Therefore, a preferred method of the invention comprises determining the presence or absence of the A allele for SNP BICF2P591872 and thereby determining whether the genome of the dog comprises a polymorphism indicative of susceptibility to liver copper accumulation. A more preferred method comprises detecting the presence or absence of the AA or AG genotype for SNP BICF2P591872.

Therefore, a more preferred method of the invention comprises detecting the presence or absence of (i) a TT or TC genotype at ATP7a_Reg3_F_6 (SNP 142); and/or (ii) a TT or TC genotype at ATP7a_Reg16_F_42 (SNP 143); and may further comprise detecting the presence or absence of:
  (iii) an AA genotype for SNP BICF2P506595 (SNP 1);
  (iv) a GG genotype for SNP BICF2P772765 (SNP 2);
  (v) a CC genotype for SNP BICF2S2333187 (SNP 3);
  (vi) a GG genotype for SNP BICF2P1324008 (SNP 4); and/or
  (vii) an AA or AG genotype for SNP BICF2P591872 (SNP 5);
and thereby determining whether the genome of the dog comprises one or more polymorphisms indicative of protection from and/or susceptibility to liver copper accumulation. A more preferred method comprises detecting the presence or absence of a genotype (iiii); a genotype (iv), (v) and (vi); or a genotype (vii). An even more preferable method comprises detecting the presence or absence of all 5 genotypes (iii) to (vii).

DNA from the dog may be typed at:
  (i) one or more SNPs selected from (a) the SNP identified in Table VI (ATP7a_Reg3_F_6 (SNP 142)) and (b) one or more SNPs in linkage disequilibrium with said SNP (a), such as the SNP identified in Table X (ATP7a_Reg16_F_42 (SNP 143)); and
  (ii) one or more SNPs selected from (a) the SNPs identified in Table III, IV and V and (b) one or more SNPs in linkage disequilibrium with a said SNP (a).

Typing the nucleotide(s) present in the genome of the dog at a position identified in any of Tables III, IV, V, VI or X may mean that the nucleotide present at this position in a sequence corresponding exactly with the sequence identified in Table III, IV, V, VI or X is typed. However, it will be understood that the exact sequences presented in SEQ ID NOs: 1 to 5 identified in Table III, SEQ ID NO: 6 to 130 in Table IV, SEQ ID NO: 131 to 141 in Table V, SEQ ID NO: 142 in Table VI and SEQ ID NO: 143 in Table X will not necessarily be present in the dog to be tested. Typing the nucleotide present may therefore be at a position identified in Table III, IV, V, VI or X or at an equivalent or corresponding position in the sequence. The term equivalent as used herein therefore means at or at a position corresponding to that identified in Table III, IV, V, VI or X. The sequence and thus the position of the SNP could for example vary because of deletions or additions of nucleotides in the genome of the dog. Those skilled in the art will be able to determine a position that corresponds to or is equivalent to the relevant position in each of SEQ ID NOs: 1 to 143, using for example a computer program such as GAP, BESTFIT, COMPARE, ALIGN, PILEUP or BLAST. The UWGCG Package provides programs including GAP, BESTFIT, COMPARE, ALIGN and PILEUP that can be used to calculate homology or line up sequences (for example used on their default settings). The BLAST algorithm can also be used to compare or line up two sequences, typically on its default settings. Software for performing a BLAST comparison of two sequences is publicly available through the National Center for Biotechnology Information (http://www.ncbi.nlm.nih.gov/). This algorithm is further described below. Similar publicly available tools for the alignment and comparison of sequences may be found on the European Bioinformatics Institute website (http://www.ebi.ac.uk), for example the ALIGN and CLUSTALW programs.

There are a variety of different methods that can be used to determine whether a polymorphism is indicative of either susceptibility to or protection from liver copper accumulation. Typically, the candidate polymorphism is compared to a database of polymorphisms and their association with susceptibility to or protection from liver copper accumulation. Such a database is generated by phenotyping a panel of dogs for liver copper accumulation, for example by liver biopsy, and classifying the dogs in terms of the level of copper accumulation. The dogs in the panel are also genotyped for a panel of polymorphisms. It is then possible to determine the association of each genotype with the level of liver copper. Determining whether a polymorphism is indicative of either susceptibility to or protection from liver copper is therefore achieved by locating the polymorphism in the database.

If a polymorphism of interest is not located in a database as described above, it is still possible to determine whether the polymorphism is indicative of either susceptibility to or protection from liver copper accumulation. This could be achieved by phenotyping a panel of dogs for liver copper accumulation and classifying the dogs in terms of the level of liver copper accumulation. The panel of dogs are then genotyped for the polymorphism of interest. The genotypes are then correlated with the level of liver copper in order to determine the association of the genotypes with liver copper level.

Once the presence or absence of the one or more polymorphisms of the invention have been detected in the genome of the dog, whether the dog is protected from, or susceptible to, liver copper accumulation is thereby determined. The genotype of each polymorphism alone or in combination with other polymorphisms is indicative of the protection from, or susceptibility of the dog to, liver copper accumulation.

To determine whether a dog is protected from liver copper accumulation one may genotype the SNP identified in Table VI in the genome of the dog using a DNA sample from the dog. This functional mutation is located in ATP7A (on the X chromosome) and appears to be protective when homozygous (TT). This may explain the female bias of chronic hepatitis as males only have one copy of the X chromosome and so are hemizygous at the ATP7A locus. An X-linked recessive gene-effect is more likely to be seen in males than females because of the hemizygous state of the male X chromosome. The protective effect here is recessive so we see more cases in the female population (See Example 2, Table VII and FIG. 5). Once the genotype of the SNP has been determined it is possible to determine whether the dog is protected from liver copper accumulation. The presence of the alternative allele (T) is indicative of protection from liver copper accumulation. A dog that is homozygous for the alternative allele (TT) is most likely to be protected from liver copper accumulation. A preferred method of the invention therefore comprises determining the presence or absence of a T allele of the ATP7A SNP in the genome of the dog. The method may comprise determining whether the dog is homozygous (in the case of female dogs) or hemizygous (in the case of male dogs) for the T allele of the ATP7A SNP.

If the method further comprises testing for the presence or absence of SNPs indicative of susceptibility to liver copper accumulation, a model may be used that combines the results to provide an overall assessment of the risk or likelihood that the dog will be susceptible to, or protected from, liver copper accumulation. As an example, Table I sets out the different possible genotypes of the combination of 5 SNPs in the region of the GOLGA5, UBL5 and ATP7A genes and the percentage of dogs with those genotypes that have high copper (liver levels of above 600 mg/kg). In this example, to determine the susceptibility of a dog to liver copper accumulation one may genotype the 5 SNPs in the genome of the dog using a DNA sample from the dog. Once the genotypes of the SNPs have been determined, these can be converted into binary values based on the key provided in Example 1, i.e. based on the degree of association of the genotype with high copper. Then, Table I is used to convert the binary values into a risk factor based on the percentage of dogs that have that genotype pattern and high copper. These results could therefore be combined with the results for the protective polymorphism(s).

A dog may be tested by a method of the invention at any age, for example from 0 to 12, 0 to 6, 0 to 5, 0 to 4, 0 to 3, 0 to 2 or 0 to 1 years old. Preferably the dog is tested at as young an age as possible, for example within the first year, first 6 months or 1.0 first 3 months of its life. The dog is preferably tested before copper accumulation occurs. The history of the dog may or may not be known. For example, the dog may be a pup of known parents and the history of the parents with respect to copper accumulation may be known. Alternatively, the dog may be a stray or a rescued dog with unknown parentage and history.

The dog to be tested by any method of the present invention may be of any breed. The invention provides a method of determining whether the genome of a mixed or crossbred dog, or a mongrel or out-bred dog comprises one or more polymorphisms indicative of protection from, or susceptibility to, liver copper accumulation.

In the method of determining whether the genome of the dog comprises one or more polymorphisms indicative of protection from liver copper accumulation of the invention, the dog may be one that is suspected of being protected from liver copper accumulation. Alternatively, the dog may be suspected of being susceptible to liver copper accumulation. In a preferred method of the invention, the dog has genetic breed inheritance of Labrador Retriever, Golden Retriever or Miniature Poodle. The dog may be a mixed or crossbred dog, or a mongrel or out-bred dog. The dog may have at least 25%, at least 50%, or at least 100% of its genome inherited from any pure breed or more preferably from any breed selected from Labrador Retriever, Golden Retriever or Miniature Poodle. The dog may be a pure-bred. In one embodiment of the invention, one or both parents of the dog to be tested are or were pure-bred dogs. In another embodiment, one or more grandparents are or were pure-bred dogs. One, two, three or all four of the grandparents of the dog that is tested may be or may have been pure-bred dogs.

Preferably, the dog has genetic breed inheritance of Labrador Retriever. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The genetic breed background of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for the genetic inheritance of a particular breed because it is suspected of having a particular breed inheritance for example by the dog owner or veterinarian. This could be for example because of knowledge of the dog's ancestry or because of its appearance.

The predictive test of the invention may be carried out in conjunction with one or more other predictive or diagnostic tests such as determining the genetic breed background/inheritance of the dog or susceptibility to one or more other diseases.

Detection of Polymorphisms

The detection of polymorphisms according to the invention may comprise contacting a polynucleotide or protein in a sample from the dog with a specific binding agent for a polymorphism and determining whether the agent binds to the polynucleotide or protein, wherein binding of the agent indicates the presence of the polymorphism, and lack of binding of the agent indicates the absence of the polymorphism.

The method is generally carried out in vitro on a sample from the dog, where the sample contains DNA from the dog. The sample typically comprises a body fluid and/or cells of the dog and may, for example, be obtained using a swab, such as a mouth swab. The sample may be a blood, urine, saliva, skin, cheek cell or hair root sample. The sample is typically processed before the method is carried out, for example DNA extraction may be carried out. The polynucleotide or protein in the sample may be cleaved either physically or chemically, for example using a suitable enzyme. In one embodiment the part of polynucleotide in the sample is copied or amplified, for example by cloning or using a PCR based method prior to detecting the polymorphism.

In the present invention, any one or more methods may comprise determining the presence or absence of one or more polymorphisms in the dog. The polymorphism is typically detected by directly determining the presence of the polymorphic sequence in a polynucleotide or protein of the dog. Such a polynucleotide is typically genomic DNA, mRNA or cDNA. The polymorphism may be detected by any suitable method such as those mentioned below.

A specific binding agent is an agent that binds with preferential or high affinity to the protein or polynucleotide having the polymorphism but does not bind or binds with only low affinity to other polynucleotides or proteins. The specific binding agent may be a probe or primer. The probe may be a protein (such as an antibody) or an oligonucleotide. The probe may be labelled or may be capable of being labelled indirectly. The binding of the probe to the polynucleotide or protein may be used to immobilise either the probe or the polynucleotide or protein.

Generally in the method, a polymorphism can be detected by determining the binding of the agent to the polymorphic polynucleotide or protein of the dog. However in one embodiment the agent is also able to bind the corresponding wild-type sequence, for example by binding the nucleotides or amino acids which flank the variant position, although the manner of binding to the wild-type sequence will be detectably different to the binding of a polynucleotide or protein containing the polymorphism.

The method may be based on an oligonucleotide ligation assay in which two oligonucleotide probes are used. These probes bind to adjacent areas on the polynucleotide that contains the polymorphism, allowing after binding the two probes to be ligated together by an appropriate ligase enzyme. However the presence of a single mismatch within one of the probes may disrupt binding and ligation. Thus ligated probes will only occur with a polynucleotide that contains the polymorphism, and therefore the detection of the ligated product may be used to determine the presence of the polymorphism.

In one embodiment the probe is used in a heteroduplex analysis based system. In such a system when the probe is bound to a polynucleotide sequence containing the polymorphism it forms a heteroduplex at the site where the polymorphism occurs and hence does not form a double strand structure. Such a heteroduplex structure can be detected by the use of a single or double strand specific enzyme. Typically the probe is an RNA probe, the heteroduplex region is cleaved using RNAase H and the polymorphism is detected by detecting the cleavage products.

The method may be based on fluorescent chemical cleavage mismatch analysis which is described for example in PCR Methods and Applications 3, 268-71 (1994) and Proc. Natl. Acad. Sci. 85, 4397-4401 (1998).

In one embodiment a PCR primer is used that primes a PCR reaction only if it binds a polynucleotide containing the polymorphism, for example a sequence-specific PCR system, and the presence of the polymorphism may be determined by detecting the PCR product. Preferably the region of the primer that is complementary to the polymorphism is at or near the 3' end of the primer. The presence of the polymorphism may be determined using a fluorescent dye and quenching agent-based PCR assay such as the Taqman PCR detection system.

The specific binding agent may be capable of specifically binding the amino acid sequence encoded by a polymorphic sequence. For example, the agent may be an antibody or antibody fragment. The detection method may be based on an ELISA system. The method may be an RFLP based system. This can be used if the presence of the polymorphism in the polynucleotide creates or destroys a restriction site that is recognised by a restriction enzyme.

The presence of the polymorphism may be determined based on the change that the presence of the polymorphism makes to the mobility of the polynucleotide or protein during gel electrophoresis. In the case of a polynucleotide, single-stranded conformation polymorphism (SSCP) or denaturing gradient gel electrophoresis (DDGE) analysis may be used. In another method of detecting the polymorphism, a polynucleotide comprising the polymorphic region is sequenced across the region that contains the polymorphism to determine the presence of the polymorphism.

The presence of the polymorphism may be detected by means of fluorescence resonance energy transfer (FRET). In particular, the polymorphism may be detected by means of a dual hybridisation probe system. This method involves the use of two oligonucleotide probes that are located close to each other and that are complementary to an internal segment of a target polynucleotide of interest, where each of the two probes is labelled with a fluorophore. Any suitable fluorescent label or dye may be used as the fluorophore, such that the emission wavelength of the fluorophore on one probe (the donor) overlaps the excitation wavelength of the fluorophore on the second probe (the acceptor). A typical donor fluorophore is fluorescein (FAM), and typical acceptor fluorophores include Texas red, rhodamine, LC-640, LC-705 and cyanine 5 (Cy5).

In order for fluorescence resonance energy transfer to take place, the two fluorophores need to come into close proximity on hybridisation of both probes to the target. When the donor fluorophore is excited with an appropriate wavelength of light, the emission spectrum energy is transferred to the fluorophore on the acceptor probe resulting in its fluorescence. Therefore, detection of this wavelength of light, during excitation at the wavelength appropriate for the donor fluorophore, indicates hybridisation and close association of the fluorophores on the two probes. Each probe may be labelled with a fluorophore at one end such that the probe located upstream (5') is labelled at its 3' end, and the probe located downstream (3') is labelled at its 5' end. The gap between the two probes when bound to the target sequence may be from 1 to 20 nucleotides, preferably from 1 to 17 nucleotides, more preferably from 1 to 10 nucleotides, such as a gap of 1, 2, 4, 6, 8 or 10 nucleotides.

The first of the two probes may be designed to bind to a conserved sequence of the gene adjacent to a polymorphism and the second probe may be designed to bind to a region including one or more polymorphisms. Polymorphisms within the sequence of the gene targeted by the second probe can be detected by measuring the change in melting temperature caused by the resulting base mismatches. The extent of the change in the melting temperature will be dependent on the number and base types involved in the nucleotide polymorphisms.

Polymorphism typing may also be performed using a primer extension technique. In this technique, the target region surrounding the polymorphic site is copied or amplified for example using PCR. A single base sequencing reaction is then performed using a primer that anneals one base away from the polymorphic site (allele-specific nucleotide incorporation). The primer extension product is then detected to determine the nucleotide present at the polymorphic site. There are several ways in which the extension product can be detected. In one detection method for example, fluorescently labelled dideoxynucleotide terminators are used to stop the extension reaction at the polymorphic site. Alternatively, mass-modified dideoxynucleotide terminators are used and the primer extension products are detected using mass spectrometry. By specifically labelling one or more of the terminators, the sequence of the extended primer, and hence the nucleotide present at the polymorphic site can be deduced. More than one reaction product can be analysed per reaction and consequently the nucleotide present on both homologous chromosomes can be determined if more than one terminator is specifically labelled.

The invention further provides primers or probes that may be used in the detection of any of the SNPs defined herein for use in the prediction of susceptibility to copper accumulation. Polynucleotides of the invention may also be used as primers for primer extension reactions to detect the SNPs defined herein.

Such primers, probes and other polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500, 600, 700 nucleotides in length, or even up to a few nucleotides, such as five or ten nucleotides, short of a full length polynucleotide sequence of the invention.

Primers and probes for genotyping the SNPs of the invention may be designed using any suitable design software known in the art using the SNP sequences in Tables III, IV, V, VI or X. Homologues of these polynucleotide sequences would also be suitable for designing primers and probes. Such homologues typically have at least 70% homology, preferably at least 80, 90%, 95%, 97% or 99% homology, for example over a region of at least 15, 20, 30, 100 more contiguous nucleotides. The homology may be calculated on the basis of nucleotide identity (sometimes referred to as "hard homology").

For example the UWGCG Package provides the BESTFIT program that can be used to calculate homology (for example used on its default settings) (Devereux et al (1984) *Nucleic Acids Research* 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as fax as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as default a word length (W) of 11, the BLOSUM62 scoring matrix (see Henikoff and Henikoff (1992) *Proc. Natl. Acad.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by at least 1, 2, 5, 10, 20 or more mutations, which may be substitutions, deletions or insertions of nucleotides The polynucleotides of the invention such as primers or probes may be present in an isolated or substantially purified form. They may be mixed with carriers or diluents that will not interfere with their intended use and still be regarded as substantially isolated. They may also be in a substantially purified form, in which case they will generally comprise at least 90%, e.g. at least 95%, 98% or 99%, of polynucleotides of the preparation.

Detector Antibodies

A detector antibody is an antibody that is specific for one polymorphism but does not bind to any other polymorphism as described herein. Detector antibodies are for example useful in purification, isolation or screening methods involving immunoprecipitation techniques.

Antibodies may be raised against specific epitopes of the polypeptides of the invention. An antibody, or other compound, "specifically binds" to a polypeptide when it binds with preferential or high affinity to the protein for which it is specific but does substantially bind not bind or binds with only low affinity to other polypeptides. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments that bind a polypeptide of the invention. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies may be used in a method for detecting polypeptides of the invention in a biological sample (such as any such sample mentioned herein), which method comprises:
I providing an antibody of the invention;
II incubating a biological sample with said antibody under conditions which allow for the formation of an antibody-antigen complex; and
III determining whether antibody-antigen complex comprising said antibody is formed.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising an antibody in a host animal against the whole polypeptide or a fragment thereof, for example an antigenic epitope thereof, hereinafter the "immunogen". The fragment may be any of the fragments mentioned herein (typically at least 10 or at least 15 amino acids long).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Detection Kit

The invention also provides a kit that comprises means for typing one or more of the polymorphisms defined herein. In particular, such means may include a specific binding agent, probe, primer, pair or combination of primers, or antibody, including an antibody fragment, as defined herein which is capable of detecting or aiding detection of the polymorphisms defined herein. The primer or pair or combination of primers may be sequence specific primers that only cause PCR amplification of a polynucleotide sequence comprising the polymorphism to be detected, as discussed herein. The primer or pair of primers may alternatively not be specific for the polymorphic nucleotide, but may be specific for the region upstream (5') and/or downstream (3'). These primers allow the region encompassing the polymorphic nucleotide to be copied. A kit suitable for use in the primer-extension technique may specifically include labelled dideoxynucleotide triphosphates (ddNTPs). These may for example be fluorescently labelled or mass modified to enable detection of the extension product and consequently determination of the nucleotide present at the polymorphic position.

The kit may also comprise a specific binding agent, probe, primer, pair or combination of primers, or antibody that is capable of detecting the absence of the polymorphism. The kit may further comprise buffers or aqueous solutions.

The kit may additionally comprise one or more other reagents or instruments that enable any of the embodiments of the method mentioned above to be carried out. Such reagents or instruments may include one or more of the following: a means to detect the binding of the agent to the polymorphism, a detectable label such as a fluorescent label, an enzyme able to act on a polynucleotide, typically a polymerase, restriction enzyme, ligase, RNAse H or an enzyme which can attach a label to a polynucleotide, suitable buffer(s) or aqueous solutions for enzyme reagents, PCR primers which bind to regions flanking the polymorphism as discussed herein, a positive and/or negative control, a gel electrophoresis apparatus, a means to isolate DNA from sample, a means to obtain a sample from the individual, such as swab or an instrument comprising a needle, or a support comprising wells on which detection reactions can be carried out. The kit may be, or include, an array such as a polynucleotide array comprising the specific binding agent, preferably a probe, of the invention. The kit typically includes a set of instructions for using the kit.

Bioinformatics

The sequences of the polymorphisms may be stored in an electronic format, for example in a computer database. Accordingly, the invention provides a database comprising information relating to SNP ATP7a_Reg3_F_6 (SEQ ID NO:142) and/or one or more polymorphisms in linkage disequilibrium thereof and their association with the protection of a dog from liver copper accumulation. The database may also comprise information relating to one or more polymorphisms in the GOLGA5, ATP7A or UBL5 genes and/or one or more polymorphisms in linkage disequilibrium thereof and their association with the susceptibility of a dog to liver copper accumulation. The database may include further information about the polymorphism, for example the degree of association of the polymorphism with the protection from, or susceptibility to, liver copper accumulation.

A database as described herein may be used to determine whether the genome of a dog comprises one or more polymorphisms indicative of protection from, or susceptibility to, liver copper accumulation. Such a determination may be carried out by electronic means, for example by using a computer system (such as a PC).

Typically, the determination of whether the genome of a dog comprises one or more polymorphisms indicative of protection from liver copper accumulation will be carried out by inputting to a computer system genetic data from the dog to a computer system; comparing the genetic data to a database comprising information relating to SNP ATP7a_Reg3_F_6 (SEQ ID NO:142) and/or one or more polymorphisms in linkage disequilibrium thereof and their association with the protection of a dog from liver copper accumulation, and optionally comprising information relating to one or more polymorphisms in the GOLGA5, ATP7a or UBL5 genes and/or one or more polymorphisms in linkage disequilibrium thereof and their association with the susceptibility of a dog to liver copper accumulation; and on the basis of this comparison, determining whether the genome of a dog comprises one or more polymorphisms indicative of protection from liver copper accumulation. This information can then be used to guide the management of the liver copper levels of the dog.

The invention also provides a computer program comprising program code means for performing all the steps of a method of the invention when said program is run on a computer. Also provided is a computer program product comprising program code means stored on a computer readable medium for performing a method of the invention when said program is run on a computer. A computer program product comprising program code means on a carrier wave that, when executed on a computer system, instruct the computer system to perform a method of the invention is additionally provided.

As illustrated in FIG. 4, the invention also provides an apparatus arranged to perform a method according to the invention. The apparatus typically comprises a computer system, such as a PC. In one embodiment, the computer system comprises: means 20 for receiving genetic data from the dog; a module 30 for comparing the data with a database 10 comprising information relating to polymorphisms; and means 40 for determining on the basis of said comparison whether the genome of a dog comprises one or more polymorphisms indicative of protection of a dog from, or susceptibility of a dog to, liver copper accumulation.

Breeding Tool

Breeding value is defined as the value of an individual as a parent and is commonly used for improving desirable traits of life-stock in the farming industry. In order to improve the overall copper handling ability of dogs and to reduce the incidence of copper associated diseases, such as chronic hepatitis, it would be advantageous to select dogs for breeding that are protected from liver copper accumulation. This problem is solved by the use of polymorphisms that can be used to determine whether a dog is protected from liver copper accumulation in order to inform breeding.

For example, the copper handling ability of the offspring of two dogs may be influenced by the genotype of the parents at the ATP7A locus. The transfer of a particular variant at this locus could be beneficial to the offspring. By determining the genotype at this locus it will be possible to assess the breeding value of a prospective parent and thereby make decisions as to whether a given breeding pair are appropriate.

Accordingly, the invention provides a method of selecting a dog for producing offspring protected from liver copper accumulation comprising determining whether the genome of a dog comprises one or more polymorphisms indicative of protection from liver copper accumulation by a method of the invention in a candidate first dog; and thereby determining whether the candidate first dog is suitable for producing offspring protected from liver copper accumulation. The method may further comprise determining whether the genome of a dog comprises one or more polymorphisms indicative of protection from liver copper accumulation by a method of the invention in a second dog of the opposite sex to the first dog. If the results are that the first and/or second dog has a genotype indicative of protection from liver copper accumulation, the first dog may then be mated with the second dog in order to produce offspring protected from liver copper accumulation.

For example, the method may comprise determining the presence or absence of one or more polymorphisms selected from SNP ATP7a_Reg3_F_6 (SEQ ID NO:142) and one or more polymorphisms in linkage disequilibrium thereof in the genome of the candidate first dog. More preferably the method comprises determining the presence or absence of the ATP7a_Reg3_F_6 SNP (SEQ ID NO:142) and/or the ATP7a_Reg16_F_42 SNP (SEQ ID NO:143). The method of the invention may comprise determining the presence or absence of the T allele of ATP7a_Reg3_F_6 (SEQ ID NO:142) and/or the T allele of ATP7a_Reg16_F_42 SNP (SEQ ID NO:143). More preferably still, the method may comprise determining whether the dog is homozygous (in the case of female dogs) or hemizygous (in the case of male dogs) for the T allele of SNP ATP7a_Reg3_F_6 and/or SNP ATP7a_Reg16_F_42 (SEQ ID NO:143). The presence of the SNP indicates that the first dog is protected from liver copper accumulation and is therefore a good candidate to be mated with a second dog. Preferably the first and second dog is homozygous or hemizygous for the T allele of the SNP. Homozygosity in either the first and/or second dog is most preferable as this increases the likelihood that the offspring will be homozygous and thereby protected from liver copper accumulation.

The invention also provides a method of selecting a dog for producing offspring protected from liver copper accumulation by making use of the polymorphisms of the invention that are indicative of susceptibility to copper accumulation. The absence of such polymorphisms in the genome of the dog indicates that the dog is a good candidate for mating. The method of the invention may therefore further comprise determining whether the genome of the candidate first dog comprises one or more polymorphisms indicative of susceptibility to liver copper accumulation; and thereby determining whether the candidate first dog is suitable for producing offspring protected from liver copper accumulation.

The method may comprise detecting the presence or absence in the genome of the candidate first dog of (c) a polymorphism in the GOLGA5, ATP7a or UBL5 gene that is indicative of susceptibility to liver copper accumulation and/or (d) a polymorphism in linkage disequilibrium with a said polymorphism (c). The method may further comprise determining whether the genome of a second dog of the opposite sex to the first dog comprises one or more polymorphisms indicative of susceptibility to liver copper accumulation. The method may therefore comprise detecting the presence or absence in the genome of a second dog of (c) a polymorphism in the GOLGA5, ATP7a or UBL5 gene that is indicative of susceptibility to liver copper accumulation and/or (d) a polymorphism in linkage disequilibrium with a said polymorphism (c). If the results are that the genome of the first and/or second dog does not have a genotype indicative of susceptibility to liver copper accumulation, the first dog may then be mated with the second dog in order to produce offspring that is not susceptible to liver copper accumulation.

The method may comprise determining the presence or absence of one or more polymorphisms selected from the SNPs identified in Table III, IV and V and one or more polymorphisms in linkage disequilibrium thereof in the genome of the candidate first dog. The presence of one or more of these polymorphisms indicates that the first dog is susceptible to liver copper accumulation and is therefore not a good candidate to be mated with a second dog to produce offspring protected from liver copper accumulation.

The candidate first dog and/or second dog may be of any breed. Preferably the candidate first dog and/or second dog has genetic breed inheritance of a breed selected from Labrador Retriever, Golden Retriever or Miniature Poodle. More preferably, the candidate first dog and/or second dog has genetic inheritance of the Labrador Retriever breed. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The genetic breed inheritance of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for a particular breed inheritance because it is suspected of having a particular breed inheritance for example by the dog owner or veterinarian. This could be for example because of knowledge of the dog's ancestry or because of its appearance.

Most purebred dogs of breeds recognized by all-breed club registries are controlled by "closed studbooks". A studbook is typically the official registry of approved dogs of a given breed kept by, for example, a breed association or kennel club. It is generally termed a "closed" studbook if dogs can only be added if their parents were both registered. Most breeds have closed studbooks, resulting in inbreeding, as genetic diversity cannot be introduced from outside the existing population. In a number of breeds recognized by kennel clubs this has resulted in high incidences of genetic diseases or disorders and other problems such as reduced litter sizes, reduced lifespan and inability to conceive naturally.

In order to avoid the problems associated with inbreeding, it would be advantageous to select dogs for breeding within a particular breed that are more distantly related to each other compared to dogs that are more closely related. Therefore in one aspect of the invention, the genetic breed inheritance of the candidate first dog and of the candidate second dog is determined in order to determine the degree of relatedness of the two dogs. In this aspect of the invention, the term "genetic breed inheritance" relates to the dog's genetic ancestry within a particular breed. The dog's genetic breed inheritance may be determined as described herein. By determining the dogs' genetic inheritance, it is possible to distinguish between dogs within a single breed in order to determine how closely related they are.

Therefore, in one aspect of the invention the degree of relatedness of the candidate first dog and the candidate second dog is determined, which comprises comparing the genetic breed inheritance of the candidate first dog with the candidate second dog of the same breed. Preferably the dogs are purebred dogs. The genetic breed inheritance of each dog may for example be determined by identifying the presence or absence of one or more breed-specific polymorphisms in said dog.

The degree of relatedness may be determined from the number of breed-specific polymorphisms that the dogs have in common. For example, two dogs of the same breed may have from 0 to 100% of the breed-specific polymorphisms tested in common, for example from 10 to 90%, from 20 to 80%, from 30 to 70% or from 40 to 60%. Therefore two dogs may have at least 10%, 20%, 30%, 40%, 50%, 60%, 70%, 80% or 90% of the breed-specific polymorphisms tested in common. The percentage of tested breed-specific polymorphisms in common between two dogs may be used as a measure of their degree of relatedness. In this aspect of the invention, the two dogs would only be mated together if they are sufficiently genetically unrelated. For example, they may only be mated together if they have less than 60%, 50%, 40%, 30% or less than 20% of the breed-specific polymorphisms tested in common.

The invention also provides a method of selecting one or more dogs for breeding with a subject dog, the method comprising:
 (a) determining for a subject dog and for each dog in a test group of two or more dogs of the opposite sex to the subject dog whether the genome comprises one or more polymorphisms indicative of protection from, and optionally one or more polymorphisms indicative of susceptibility to, liver copper accumulation; and
 (b) selecting one or more dogs from the test group for breeding with the subject dog.

The test group may consist of at least 2, 3, 4, 5, 10, 15, 20, 25, 30, 50, 75, 100 or 200 different dogs, for example from 2 to 100, from 5 to 70 or from 10 to 50 dogs. The dogs are typically selected from the test group on the basis of being protected from liver copper accumulation. The dog or dogs selected from the test group may have the same or similar genetic breed inheritance as the subject dog.

The subject dog and each dog in the test group may be of any breed. Preferably the subject dog and/or each dog in the test group has genetic breed inheritance of a breed selected from Labrador Retriever, Golden Retriever or Miniature Poodle. More preferably the dog has genetic breed inheritance of the Labrador Retriever breed. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed. In one embodiment of the invention, the dog within the test group that is most likely to be protected from liver copper accumulation, based on the presence or absence of polymorphisms associated with protection from or susceptibility to liver copper accumulation, is selected for breeding with the subject dog. In another embodiment, a number of the dogs within the test group that are likely to be protected from liver copper accumulation are selected for breeding with the subject dog. For example, at least 2, 3, 4, 5, 10, 15 or 20 dogs in the test group may be selected. A further selection may then be made from the group of selected dogs based on other factors, for example geographical location, age, breeding status, medical history, disease susceptibility or physical characteristics.

As explained above, it is desirable to mate dogs within the same breed that are most genetically unrelated. This is in order to increase or maintain genetic diversity within the breed, and to reduce the likelihood of problems relating to inbreeding arising within the offspring. A further selection of the dogs from the test group may therefore be based on the genetic relatedness of the dogs with the subject dog. Accordingly, in one aspect of the invention, the method may further comprise:
 (a) comparing the genetic breed inheritance of the subject dog with the genetic breed inheritance of each dog in a test group of two or more dogs of the same breed and of the opposite sex to the subject dog;
 (b) determining from the comparison the degree of relatedness between the subject dog and each dog in the test group; and
 (c) selecting one or more dogs from the test group for breeding with the subject dog.

The dogs may be selected from the test group on the basis of their relatedness to the subject dog (i.e. the dog to be bred from). Preferably the dog or dogs selected from the test group are the most distantly related (i.e. have the lowest degree of relatedness) within the test group of dogs. The genetic breed inheritance of the subject dog and the dogs in the test group may be already known or may be determined e.g. by a commercially available breed test.

The invention thus provides a method of recommending one or more suitable dogs for breeding with a subject dog. The recommendation may be made to the subject dog's owner or carer, a veterinarian, dog breeder, kennel club or breed registry.

The invention also relates to a method of breeding dogs, wherein the protection from, or susceptibility to, liver copper accumulation of at least two dogs of the opposite sex is determined, optionally within the same breed, before breeding them together.

The protection from, or susceptibility to, liver copper accumulation of a dog may be stored in an electronic format, for example in a computer database. Accordingly, the invention provides a database comprising information relating to the susceptibility to, or protection from, liver copper accumulation and sex of one or more dogs. The database may include further information about the dog, for example the dog's genetic breed inheritance, breeding status, age, geographical location, medical history, disease susceptibility or physical characteristics. The database will typically further comprise a unique identifier for each dog, for example the dog's registered name. The database may be accessed remotely, for example using the internet.

Foodstuff of the Invention

The present invention is concerned with a foodstuff for dogs having the genetic inheritance of the Labrador Retriever breed. The inventors found that the level of copper found in commercial diets is associated with liver copper accumulation in Labrador Retrievers and that reducing the level of copper in the diet surprisingly allows the liver copper level to be brought to a normal level more efficiently than the drug penicillamine. The foodstuff of the invention has a low copper concentration, specifically a copper concentration of less than 21 mg/kg dry matter. The foodstuff is used to prevent the accumulation of copper in the livers of Labrador Retrievers. It is therefore useful for preventing a disease or condition attributable to liver copper accumulation. Thus, the foodstuff of the invention can be given to a dog wherein the genome of the dog has been determined to comprise one or more polymorphisms indicative of susceptibility to liver copper accumulation by a method of the invention. The term "foodstuff" as used herein covers foodstuff, diet, comestible or supplement. Any of these forms may be solid, semi-solid or liquid.

In more detail, the foodstuff of the invention comprises copper at a concentration of less than 21 mg/kg dry matter. Preferably, the copper concentration is less than 20, less than 17, less than 15, less than 12, less than 10 or less than 8 mg/kg dry matter. Preferably, the copper concentration is at least 3, at least 3.5, at least 4, at least 4.5, at least 4.75, at least 5 or at least 8 mg/kg dry matter. Typically, the copper concentration is in the range of 3 to 21 mg/kg, preferably 4 to 12 mg/kg, 4.5 to 12 mg/kg, 4 to 11 mg/kg, 4.5 to 11 mg/kg, 4 to 10 mg/kg, 4.5 to 10 mg/kg, 4 to 9 mg/kg, 4.5 to 9 mg/kg, 4 to 8 mg/kg, or 4.5 to 8 mg/kg dry matter. The copper may be present in the foodstuff in any physiologically acceptable form. Thus the copper may be provided in any physiologically acceptable salt such as copper sulphate.

The foodstuff may further comprise zinc at a concentration of at least 120 mg/kg dry matter. Preferably the zinc concentration is at least 150, at least 180 or at least 200 mg/kg dry matter. Preferably the zinc concentration does not exceed the maximum allowed by food regulatory authorities. Typically, the zinc concentration is less than 250, less than 240, less than 230 or less than 220 mg/kg dry matter. Typically, the zinc concentration will be in the range of 120 to 250, 150 to 250 or 200 to 250 mg/kg dry matter.

Preferably the amount of zinc in the foodstuff exceeds the amount of copper. It will be appreciated that the effective concentration of zinc and/or copper in the foodstuff that is ingested by the dog is affected by the presence or absence of non-digestible matter. Preferably the ratio of zinc to copper in the foodstuff is 5 or more, for example 6, 7, 8, 9, 10 or more, by mass of the foodstuff.

The zinc may be provided in the same foodstuff providing the level of copper of the invention. Alternatively, zinc may be provided in the form of a supplement, which can be added to a foodstuff of the invention. A supplement can be in the form of a tablet, powder or liquid formulation. The Zinc may be present in the foodstuff or provided as a supplement in any physiologically acceptable form. Thus the zinc may be in any physiologically acceptable salt such as zinc acetate, zinc sulphate, zinc gluconate, zinc carbonate, zinc chloride or zinc oxide.

The concentration of copper or zinc in the foodstuff is described herein on a dry matter basis, i.e. on the basis of the foodstuff without water, to enable direct comparison between different foodstuffs that may have different moisture content. To measure the concentration of copper or zinc in a wet or semi-wet foodstuff, a sample of the foodstuff is first dried, for example using an oven, to remove water. Thereafter, any suitable technique may be used to measure the concentration of copper or zinc in the sample of the dried foodstuff. An example of such a technique that is well known in the art is flame atomic absorption spectrophotometry.

The foodstuff of the invention may be in the form of, for example, a wet pet food, a semi-moist pet food or a dry pet food. Wet pet food generally has a moisture content above 65% by weight. Semi-moist pet food typically has a moisture content between 20-65% by weight and can include humectants and other ingredients to prevent microbial growth. Dry pet food, also called kibble, generally has a moisture content below 20% by weight and its processing typically includes extruding, drying and/or baking in heat.

The foodstuff may be provided as a mixture of wet and dry food. Such a combination may be provided premixed or may by provided as two or more separate foodstuffs, which are provided to the dog separately, simultaneously or sequentially.

The foodstuff encompasses any product that the dog consumes in its diet. The invention covers standard food products as well as pet food snacks. The foodstuff is preferably a cooked product. It may incorporate meat or animal-derived material (such as beef, chicken, turkey, lamb, fish etc). The product may alternatively be meat-free (preferably including a meat substitute such as soya, maize gluten or a soya product in order to provide a protein source). The product may also contain a starch source such as one or more grains (e.g. corn, rice, oats, barley etc), or may be starch free.

The ingredients of a dry pet food may be selected from cereal, grain, meat, poultry, fat, vitamin and mineral. The ingredients are typically mixed and put through an extruder/cooker. The product is then typically shaped and dried, and after drying, flavours and fats may be coated or sprayed onto the dry product.

All pet food is required to provide a certain level of nutrients. For example, the Association of American Feed Control Officials (AAFCO) and the Pet Food Institute have established nutrient profiles for dog foods, based on commonly used ingredients. These established profiles are called the "AAFCO dog food nutrient profiles". Under these regulations, dog foods must be formulated to contain concentrations of nutrients that meet all minimum levels and not to exceed the maximum levels as determined by AAFCO.

The dog food formulation may be customised according to the caloric, protein, fat, carbohydrate, fibre, vitamin or mineral requirements of the dog. For example, the dog food formulation may be customised to provide the correct amounts or ratio of essential fatty acids such as omega-6 and omega-3 fatty acids. The main sources of omega-6 fatty acids are plants such as sunflower, soyabean oil, safflower and evening primrose oil, whereas omega-3 fatty acids are mainly found in linseed and marine sources. Food ingredients that are high in copper and may be avoided in the production of the foodstuff include shellfish, liver, kidney, heart, meat, nuts, mushrooms, cereals, cocoa, legumes and soft water (copper pipes). Food ingredients that are rich in zinc and may be included in the formulation include milk, gelatin, egg yolks, rice and potatoes.

The foodstuff is preferably packaged. The packaging may be metal (usually in the form of a tin or flexifoil), plastic (usually in the form of a pouch or bottle), paper or card. The amount of moisture in any product may influence the type of packaging, which can be used or is required.

The foodstuff of the invention may be packaged together with a source of zinc. Zinc may be provided in any form. Zinc may be provided within one or more foodstuffs or in the form of a separate supplement that is packaged with the foodstuff comprising the maximum level of copper of the invention. When the zinc is provided in a foodstuff, it may be provided within the same foodstuff containing the particular level of copper of the invention or it may be provided in one or more separate foodstuffs or both. The invention therefore provides a pack comprising a foodstuff having copper at a concentration of less than 21 mg/kg dry matter and a zinc supplement. The zinc supplement provides a concentration of at least 120 mg/kg dry matter when added to the foodstuff. The foodstuff and zinc supplement are for simultaneous, separate or sequential use in preventing a disease attributable to liver copper accumulation in a dog having genetic inheritance of the Labrador Retriever breed.

The invention also provides a labelled foodstuff as discussed herein. The label may for example indicate that the foodstuff is suitable for a dog of the Labrador Retriever breed. Other indications or instructions could be provided. For example, the amount of copper and/or zinc that the diet or foodstuff contains, in addition to other ingredients, may be stated. Furthermore, feeding instructions could be provided.

Labrador Retriever

The foodstuff of the invention is suitable for preventing liver copper accumulation in a dog having genetic inheritance of the Labrador Retriever breed. The dog is typically a companion dog or pet. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The genetic breed background of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for Labrador Retriever breed inheritance because it is suspected of having a Labrador Retriever breed inheritance for example by the dog owner or veterinarian. This could be for example because of knowledge of the dog's ancestry or because of its appearance.

The food is suitable for a dog of any age. The food may be suitable for a dog that has an age of from 0 to 12 years old, for example from 1 to 5 years old, from 2 to 7 years old or from 3 to 9 years old.

Generally, the foodstuff is suitable for a healthy dog. It is suitable for a dog that does not have a detectable accumulation of hepatic copper. The foodstuff is intended for prophylactic use, i.e. to prevent the accumulation of copper in the liver of a dog. The foodstuff is intended for minimising the risk of copper accumulation and thereby reducing the probability of the dog from developing a disease or condition attributable to liver copper accumulation such as chronic hepatitis, cirrhosis or liver failure. Typically, the foodstuff is for use in preventing copper accumulation in a dog that does not have an abnormal hepatic copper concentration and is therefore not likely to be at risk of suffering from copper-associated hepatitis. The dog may also have no history of accumulating copper. The dog therefore preferably has a normal level of hepatic copper in the range of less than about 400 mg/kg of dry liver weight. However, in newborn dogs the normal level of hepatic copper may be considered to be less than about 600 mg/kg dry liver weight. The aim of providing the foodstuff to the dog is to prevent the hepatic copper concentration from reaching levels significantly higher than the normal level. Methods that can be used to determine the concentration of copper in the liver of 30 a dog are well known in the art. A suitable method is described in Example 6.

The foodstuff can be used for preventing copper-associated chronic hepatitis. The foodstuff is preferably for use in preventing copper accumulation in a dog that does not have detectable liver disease, with the aim of preventing such liver disease. The foodstuff could also be used to treat a disease or condition attributable to liver copper accumulation, such as chronic hepatitis, cirrhosis or liver failure. Evidence or symptoms of liver disease include clinical indications such as lethargy, diarrhoea and icterus. Biochemical indications of liver disease include abnormally increased serum bilirubin and serum liver enzyme activities such as alkaline phosphatase (ALP), alanine aminotransferase (ALT), aspartate aminotransferase (AST) and gamma-glutamyl transpeptidase. The biochemical measurement of such liver disease indicators is well known in the art.

Preferably the dog that the food is intended for does not have any clinical problems.

Food Manufacturing

The foodstuff of the invention can be made by mixing together suitable ingredients. The manufacture is controlled so that the foodstuff has the required copper concentration. The concentration of copper may be monitored during the foodstuff production process. The invention therefore provides a method of making the foodstuff of the invention comprising mixing together the ingredients for the foodstuff so that the foodstuff has a copper concentration of less than 21 mg/kg dry matter. One or more of the components to be incorporated into the foodstuff may provide a source of copper. However it is important to avoid the use of components that are likely to be rich in copper. Food ingredients that are high in copper and may be avoided in the production of the foodstuff include shellfish, liver, kidney, heart, meat, nuts, mushrooms, cereals, cocoa, legumes and soft water (copper pipes). Optionally, one or more of the components will provide a source of zinc for the foodstuff of invention. Food ingredients that are rich in zinc and may be included in the formulation include milk, gelatin, egg yolks, rice and potatoes. The components/ingredients may be added at any time during the manufacture/processing of the foodstuff.

It is important to measure the concentration of copper that is present in the foodstuff to determine that the concentration is below the limit according to the invention. The concentration of zinc could also be measured to check that it is above the minimum level that is preferred according to the invention. One of the steps in the method of manufacture of the foodstuff may comprise measuring the copper concentration in a sample of the foodstuff. At least one measurement of the copper concentration may be made from a sample of the foodstuff after the foodstuff has been prepared. Measurements could also be made during the preparation of the foodstuff in order to monitor the levels of copper and/or zinc that are accumulating by the addition of further ingredients. For example, a measurement could be made on a sample after the addition of one or more ingredients. Measurements of copper, zinc and other elements can be made on a sample using any suitable method known in the art such as flame atomic absorption spectrophotometry.

Typically, the method of making the foodstuff of the invention comprises the steps of mixing together the ingredients with optional cooking of any raw ingredients; measuring the concentration of copper, and optionally zinc, in a sample of the foodstuff; and packaging the foodstuff. The method of making the foodstuff may further comprise providing the dog's owner, the person responsible for feeding the dog or a vet with the foodstuff and/or providing the foodstuff to the dog.

Whilst it would be unusual for a foodstuff not to contain any copper, copper could be added as a supplement to the foodstuff in order to achieve the minimum daily requirement of copper in the dog's diet (for example as recommended by the American Feed Control Official (AAFCO)) whilst still maintaining the copper concentration at a level below that required by the invention. The invention therefore also provides the use of copper in the manufacture of a foodstuff for a dog having genetic inheritance of the Labrador Retriever breed, wherein the foodstuff comprises copper at a concentration of less than 21 mg/kg and is for use in preventing copper accumulation in said dog. The copper may be added to the foodstuff in any suitable form. Examples of copper supplements include cupric chloride and cupric sulphate pentahydrate. The food product manufacturing apparatus used in the present invention typically comprises one or more of the following components: container for dry pet food ingredients; container for liquids; mixer; former and/or extruder; cut-off device; cooking means (e.g. oven); cooler; packaging means; and labelling means. A dry ingredient container typically has an opening at the bottom. This opening may be covered by a volume-regulating element, such as a rotary lock. The volume-regulating element may be opened and closed according to the electronic manufacturing instructions to regulate the addition of dry ingredients to the pet food. Dry ingredients typically used in the manufacture of pet food include corn, wheat, meat and/or poultry meal. Liquid ingredients typically used in the manufacture of pet food include fat, tallow and water. A liquid container may contain a pump that can be controlled, for example by the electronic manufacturing instructions, to add a measured amount of liquid to the pet food.

In one embodiment, the dry ingredient container(s) and the liquid container(s) are coupled to a mixer and deliver the specified amounts of dry ingredients and liquids to the mixer. The mixer may be controlled by the electronic manufacturing instructions. For example, the duration or speed of mixing may be controlled. The mixed ingredients are typically then delivered to a former or extruder. The former/extruder may be any former or extruder known in the art that can be used to shape the mixed ingredients into the required shape. Typically, the mixed ingredients are forced through a restricted opening under pressure to form a continuous strand. As the strand is extruded, it may be cut into pieces (kibbles) by a cut-off device, such as a knife. The kibbles are typically cooked, for example in an oven. The cooking time and temperature may be controlled by the electronic manufacturing instructions. The cooking time may be altered in order to produce the desired moisture content for the food. The cooked kibbles may then be transferred to a cooler, for example a chamber containing one or more fans.

The pet food manufacturing apparatus may comprise a packaging apparatus. The packaging apparatus typically packages the pet food into a container such as a plastic or paper bag or box. The apparatus may also comprise means for labelling the pet food, typically after the food has been packaged. The label may indicate the type of dog that the foodstuff is suitable for (i.e. Labrador Retriever), and/or the ingredients of the food.

Use of the Foodstuff

The foodstuff of the invention may be used in a method of preventing liver copper accumulation in a dog. Therefore, it may be used for preventing a disease or condition associated with high liver copper such as copper-associated chronic hepatitis, cirrhosis or liver failure. Accordingly, the invention provides a method of preventing liver copper accumulation and a disease attributable to liver copper accumulation in a dog having genetic inheritance of the Labrador Retriever breed, comprising feeding the dog the foodstuff as described herein. The invention also provides a method of preventing copper-associated chronic hepatitis in a dog having genetic inheritance of the Labrador Retriever breed comprising providing the foodstuff of the invention to the dog. The foodstuff of the invention is typically for prophylactic use in preventing the accumulation or copper in Labrador Retrievers. It is also typically for preventing copper-associated chronic hepatitis in Labrador Retrievers.

The foodstuff of the invention is preferably for use in a method of preventing the accumulation of liver copper in a dog, the genome of which dog has been determined to not comprise one or more polymorphisms indicative of protection from liver copper accumulation, and optionally has been determined to comprise one or more polymorphisms indicative of susceptibility to liver copper accumulation, by the genetic test described herein.

Therefore the invention provides a method of preventing a disease attributable to liver copper accumulation in a dog having genetic inheritance of the Labrador Retriever breed, comprising (i) determining the likelihood that a dog is protected from liver copper accumulation comprising detecting the presence or absence in the genome of the dog of one or more polymorphisms selected from (a) SNP ATP7a_Reg3_F_6 (SEQ ID NO:142) and (b) one or more polymorphisms in linkage disequilibrium with (a); and (ii) prescribing, providing or feeding the dog with a foodstuff comprising copper at a concentration of at least 4.5 to less than 12 mg/kg dry matter. The foodstuff may be provided to the dog's owner, carer or vet. The invention also provides a foodstuff for use in said method.

The use of the foodstuff of the invention may comprise providing a source of zinc to the dog. As described herein, zinc may be provided in any suitable form to the dog. The foodstuff containing the low level of copper of the invention may further comprise zinc, for example at a concentration of at least 120 mg/kg dry matter. Alternatively, zinc may be provided in the form of one or more separate foodstuffs or supplements. The use of the foodstuff of the invention may comprise providing a zinc supplement to the dog. A zinc supplement could be provided at any time, i.e. separately, simultaneously or sequentially to the foodstuff of the invention. The zinc supplement could for example be mixed with the foodstuff of the invention before it is provided to the dog, or it could be put into the dog's drinking water.

The foodstuff of the invention may be provided to the dog one or more times per day. The foodstuff is preferably provided in place of the dog's conventional food. The method of preventing copper accumulation or preventing chronic hepatitis may be used for an indefinite period of time, i.e. throughout the dog's life.

The invention is illustrated by the following Examples:

Example 1

Elucidation of SNPs Associated with Susceptibility to Copper Accumulation

120 Labrador DNA samples were genotyped across more than 22000 SNPs. There were 72 dog samples from high copper dogs (liver levels of copper above 600 mg/kg) and 48 dog samples from normal copper liver levels (below 400 mg/kg). The data was analysed using pairwise comparison between every possible pair of dogs. Data was ordered according to support of a disease informative locus. Data from the best three genomic locations was used using Boolean operators to find the best fitting markers linked to high copper levels. Results of a simple Boolean model using the three locations are given below:

TABLE I

Results of simple Boolean model using the
genomic locations CFA8, CFA32 and CFAX

| CFA8 (GOLGA5 gene region) | CFA32 (UBL5 gene region) | CFAX (ATP7A gene region) | % of dogs with this pattern of alleles that have high copper | |
|---|---|---|---|---|
| 1 | x | x | 69.0% | |
| 1 | 1 | x | 72.3% | |
| 1 | 1 | 1 | 81.5% | Of the 27 dogs with all three alleles, 22 (81.5%) have high copper |
| 1 | 1 | 0 | 60.0% | |
| 1 | 0 | x | 64.9% | |
| 1 | 0 | 1 | 77.8% | |
| 1 | 0 | 0 | 60.7% | |
| 0 | x | x | 36.1% | |
| 0 | 1 | x | 55.6% | |
| 0 | 1 | 1 | 42.9% | |
| 0 | 1 | 0 | 63.6% | |
| 0 | 0 | x | 16.7% | |
| 0 | 0 | 1 | 50.0% | |
| 0 | 0 | 0 | 7.1% | Of the 14 dogs with none of the three alleles, 1 has high copper |

The key to the binary values in Table I is as follows:
Genomic location CFA8 (GOLGA5 gene)
1=if there is an AA genotype at SNP BICF2P506595
0=if there is any other genotype at SNP BICF2P506595
Genomic location CFA32 (UBL5 gene region)
1=if there is a GG at BICF2P772765, a CC at BICF2S2333187 and a GG at BICF2P1324008
0=if any of those SNPs show a different genotype
Genomic location CFAX (ATP7A gene region)
1=if there is an AA or an AG at BICF2P591872
0=if there is a GG at BICF2P591872
In all locations, X=unused alleles.

Table I represents the binary conditions of alleles at three genomic locations. At genomic location CFA8, one SNP was used (SNP 1). At genomic location CFA32 three SNPs were used (SNPs 2, 3 and 4). At genomic location CFAX one SNP was used (SNP 5). The binary values are indicative of a dog having alleles that are indicative of susceptibility to copper accumulation ("bad" alleles). For instance 000 represents not having any of the three bad alleles. 111 represents having all three bad alleles. The Xs are unused alleles at that gene. The lines 1xx and 0xx show the power that a one gene test only using the SNP in the GOLGA5 gene would have.

Table II shows that dogs with more of the indicative alleles have higher copper concentration on average. We can also see the number dogs with each pattern:

TABLE II

| Gene Combination | Average amount of $Cu_2$ (mg/kg) | % of dogs with this pattern of alleles that have high copper | Number of dogs with pattern |
|---|---|---|---|
| 111 | 1253.09 | 81.5% | 27 |
| 110 | 733.40 | 60.0% | 20 |
| 101 | 1138.90 | 77.8% | 9 |
| 100 | 737.84 | 60.7% | 28 |
| 011 | 502.27 | 42.9% | 7 |
| 010 | 670.83 | 63.6% | 11 |
| 001 | 450.00 | 50.0% | 4 |
| 000 | 332.47 | 7.1% | 14 |

Table III shows the position and sequence of the SNPs used for the results in Tables I and II.

The results implicated three genomic locations (in and around the GOLGA5, UBL5 and ATP7A genes) associated with susceptibility to copper accumulation. Further SNPs in these regions that are indicative of susceptibility to copper accumulation are provided in Table IV.

TABLE III

Position and sequence of SNPs used for results in Table I and II

| SNP name (SNP no.) | SEQ ID NO: | Chromosome in canfam 2 | Location in canfam 2 | Gene containing or close to mutation | SNP Sequence SNP = [first allele/second allele] |
|---|---|---|---|---|---|
| BICF2P506595 (SNP 1) | 1 | 8 | 4886813 | GOLGA5 | CTCAGAACTAGATAGGCTAATAAGTGATAGGCCTTGTGTTTTC CTAGAGTGTGCTTTAAA[A/G]GTTTCTTAAGCTAAAAAATTA CATTCGTGAGAAAATTGAAATAAAAGGAAAACAGTCATG |
| BICF2P772765 (SNP 2) | 2 | 32 | 39278300 | UBL5 | TCTCAGATACTTGATAGCCAGCATTTCCCCCCATTTTCTTCCA AGAGCACGAAAGCATAG[A/G]AATGATATTACATCTCGTATG GTGAATGTGACACAGCCGTCAGTTGCGTTAGCTCTGCTT |
| BICF2S2333187 (SNP 3) | 3 | 32 | 39390236 | UBL5 | TATTACCCTGCTCTCCAGCCACTCCTTTACCTTCCATTAGCCC ACACCTGCTCTACACAC[T/C]ATTGCTCATGGAAGCCTTGCC ACGTCCAGTCGCCACTCTGAAATGCCAGCATCCCTCCCA |
| BICF2P1324008 (SNP 4) | 4 | 32 | 40043909 | UBL5 | GACCTGACAGATTATGTAGACTTTGTTTTCAAAGGGAGCACCT GCTGGATATACAACATG[A/G]CACTAAATTGTGCTCCACATC CTTGGCAGAGGTGGGGGGCGGGGCACAAAGGAAGAAACC |
| BICF2P591872 (SNP 5) | 5 | X | 62989720 | ATP7A | GGGCCCAGCAAGTGGCAGAACTGGGAAGACCCCCTCTTCTTCC GCCTGGAGCAGTGGTGT[A/G]GCAGCACACCACAGGAGTCTG AAAGGGTGGGGAGTCCAAACGGGAACATATACCTGAGAT |

TABLE IV

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P1246154 (SNP 6) | 6 | X | 47335181 | 0.999507 | 0.000493 | GGCAACAGGGACAGGCTGCTGGGCCACACACTCACCCACACT AGGAGACAAGATCCTCCA[T/C]ATCCTGGGTCTCTATCAGT CAATCACCTAGACCAGTGGGCCAGAGGACAGGGTCCAGCTG |
| BICF2P463335 (SNP 7) | 7 | X | 44401786 | 0.000493 | 0.000493 | GTTGAGAGAGATCATACAGATTCATGTGGCAGGTGCACACTT TTTTACCTCTTACAACG[T/C]ATTCTCTCTGGCCATTCCT TCTCCTGGGTCCCAAAGTCGGAGAGCTTAGCGGGAGCCTAG |
| BICF2P1246989 (SNP 8) | 8 | 8 | 4149835 | 0.999506 | 0.000494 | ataagttcacattttgGTGTTTCAAGTGGACATGAATGGAGG GGAGGGCCCTGTTCAATC[T/C]ACTAAAGTGTTTTTTCATC TTGTTTTTGTGGAAATCAAATCAAGAAGCAGAGTTTTATGT |
| BICF2P723557 (SNP 9) | 9 | 8 | 3406227 | 0.999014 | 0.000986 | ACTCTCCCGATGTGGGCACCCATATGGTGGACCACTTTCTGTG TGAGATGCCTGCTCTTAT[T/C]GCCATGTCCTGTGAAGACA CCATGCTGGTGGAAGCATTTGCCTTTGCCCTGGGTGTTGCC |
| BICF2S23427298 (SNP 10) | 10 | 8 | 5393517 | 0.999014 | 0.000986 | AATCTAAGTAGACTGAGTGGTCACCTTCAGCGCTCAGACCTG AGCATACAAAGCATGGAA[A/G]GTTACTGTGATTCAGCTGA TGTAATGGAATGAAATAAATATAAGAGTTTGGTAACCTAAT |
| BICF2P312189 (SNP 11) | 11 | 8 | 5773958 | 0.999014 | 0.000986 | TGGAGAGTGCTGGCAGGCAGGGGCAGGCAAACAACAATAGCA AAGATCTCTTCCACGCTT[T/C]TACTTCCTCAAAAGTCCAA GCCCTCTTAAGATCGCATTTTCTTAGTGACCTTCACTCTAA |
| BICF2S24321583 (SNP 12) | 12 | X | 56410647 | 0.999014 | 0.000986 | TTCTTTGCTAGGCCAAGGGCAGAGAATGCATGCCCCCCCTTA CCTCCCAGGGCCCAAGAG[C/G]CATCCTGAGCTGAGTCTAT GGCTCCTGGTGGGGGGCGGCTGTGGGTTGGGGGGGCACAGA |
| BICF2P1273450 (SNP 13) | 13 | 8 | 3160594 | 0.999013 | 0.000987 | ggtgtcaccaatgccagcgagcaccagctggagggaacagga cacaggtcctccgtcCTG[T/C]GACACTCGGATCTGGGGCT TTGCCTCCAAAACGGAGACCATGCCTGTCCATGGTTCTACG |
| BICF2P1439540 (SNP 14) | 14 | 8 | 3771142 | 0.998521 | 0.001479 | CTCTAGAACCCTTCAGGTAGACTACATTCACTTTCTACTACA ACTTCATCACCACAACCA[A/T]CTCCCAGTAACCCCCtttt tttcttctcctttttttattttttccttcttttttgctcgtc |
| BICF2P506204 (SNP 15) | 15 | 8 | 4191144 | 0.998521 | 0.001479 | TCCCATGGGTTGAAGGATATCTGGCAGACGGCTCCAACTCCA GTAAAGCCTCAGGCCTCA[A/G]CCAGGAGTTCCCCGGGGCT TCATTCCCATCCCAGACTTTGCCCAGGGCTGATTTGAAAGT |
| BICF2P380732 (SNP 16) | 16 | 8 | 3299879 | 0.998519 | 0.001481 | TCTTCCTTGCAGATTGGATGGCTGTAGCCTCACCTCACACTG TTGCTGGGATCTGTCCAC[A/G]CTTCTGACCTCCAGCAAGA GCCTCCGGGAGCTAAGCCTGGGCAGCAATGACCTGGGAGAT |
| BICF2G63016020 (SNP 17) | 17 | X | 73980557 | 0.004955 | 0.004955 | TATTGCTAGTAAAGCCAAACTTTCTATTCCACAATTATAAAC TCATGGAGATGGTAATTA[T/C]AGTGCATTATTTGTCAAAT TTTATTATTTTTTCAAATCCCAAAGAAAATGTGATATTCTA |
| BICF2S23623569 (SNP 18) | 18 | 32 | 38362784 | 0.994576 | 0.005424 | AAGAACAAGGATACAATCTAAGTGATAATCATCCAGCATGTA CTTGTCCTGTTTTCAGAT[T/G]ATCAGCTTAAGTCAAGAGG AATTTTTAGTGCTTACAAATATTTCAAGTGATTTTTCCAGA |
| BICF2P216837 (SNP 19) | 19 | 8 | 7474389 | 0.012327 | 0.012327 | TGAAGGGGTGCTACTCAGGGCTCTTCATTTAACCTTCCAGGA TGTTTTCCTATGTACTCA[T/C]TCTTCCTTTTGGTTGCTCC TTCTTCTTGCATTTCTTTATCTCTTTACAGAATCATCCAGG |
| BICF2S22922146 (SNP 20) | 20 | X | 75388683 | 0.986193 | 0.013807 | acaaccctaaaatttcagtgattcagtacaacaaaggtttat tATAACCATTCAGGGATC[C/G]AAGTTGGTAGAAACTTCAC TACAATACCTGCTTCCAGTCAACAAGACAGAAAAGAAAAA |
| BICF2G63015714 (SNP 21) | 21 | X | 74415223 | 0.01382 | 0.01382 | GCAGGGTTGATATATAACTAGTATGCATTAGGTAGACACCTA TTTTGATTACTCACTATT[T/G]TAATATCAGCCTGGTAGTA AGAACCAAATCTATTATGTAAAGTGCATAGAGAATTGaaag |
| BICF2G63015674 (SNP 22) | 22 | X | 74439123 | 0.0143 | 0.0143 | CTAGCTAGCCACCCAACTCCCCACATGCCCAGAGTCATCGTT TATCTTTTCACATCAGCA[T/C]TACATTTTGGCTTGCATTC AAACATTAGCCCATTTTTTTCCTTTTGTTTTATTTATAGA |
| BICF2P426463 (SNP 23) | 23 | 8 | 5833993 | 0.015286 | 0.015286 | TTTTCTCTTTTTCCATAAATGCTCTGGGCTTATTTTCATTAT CTAGTATTTCTCTTCTGA[A/G]GCTAACTCCCAAAGAGTTT TGTGCATCCTTATTTCCATCACAAGGTCAATGTACGAGTTA |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2S22926688 (SNP 24) | 24 | 8 | 7502279 | 0.015779 | 0.015779 | GGGCCCAAGGGCTGAGGATCTCTGTACCTTCTGCTTCTTGGC AGCCCAGGCTGGGTAGCA[T/G]TTCTTGGAAGAGGATTTCC CATGAGTTGTTAACAGAAGGGCGGGCTTCCAGGCGCTGCTT |
| BICF2P1113947 (SNP 25) | 25 | 32 | 38074100 | 0.981169 | 0.018831 | CATCTTTGCTTGGGGCCTGGGGTTTTTATTGAGGATTGTGAT CTGGTGTATGTGTCTCCT[T/C]AGGCATCCAGAAACCATTC AGAACAAGAACAAGCGTCCAGGTATCCTCTGTAAGTCACTT |
| BICF2P342874 (SNP 26) | 26 | X | 44861101 | 0.020217 | 0.020217 | ACAAACCCTCAGACCCAGATACACAGTATCATGTGGACACAG ACATGTAACACCAAAATG[A/C]CCAACATCATGTGACTACA GGCCCTAAGCAACTAGGTGTAACATCACTTGGGTATGGGCC |
| BICF2P1171925 (SNP 27) | 27 | 32 | 36457625 | 0.022189 | 0.022189 | AATGCAGTAATACATGTAGCTAAACCTAACCATCAGAGTCTG TTCTATCCTTCTACAAAA[A/G]TAGGGTTGGAGCTGAGCAC ATAGGTAGCATACATCTAGCAAAAGTTTTTGCCTTCAgatt |
| BICF2G63017200 (SNP 28) | 28 | X | 71984532 | 0.025641 | 0.025641 | ttgtgggtcaggtgagttatggacccctccctactcttctg ctatcttgccccCTACAG[T/G]GGTTGCTATTTTGATGTAA TCACAAAACGACCTGGCAATAAAACCTTTTTCTAATTAggg |
| BICF2P1286548 (SNP 29) | 29 | X | 57448138 | 0.026423 | 0.026423 | GATGCAAGCTGGGACAGAATAAGGTACTGGGCTGTGTCAAGC CCCAGTAAGAGAGGAGCA[T/C]TGTAGGGTAGTTAGGATGG ACTTAATGGAGATGAGTCCTAGGGAGCCACACTCAGAGTTA |
| BICF2P790089 (SNP 30) | 30 | 32 | 38885957 | 0.0286 | 0.0286 | TAAACACCCCAATCACTACCATCCTCACACCTAAGGATACA CAATGTGTCTACTTTATG[A/G]TATGTCTTTACTATTCGTT GCTTATGAAATTTTATTCATTAWCTAAAACAGGGAAAAAAG |
| BICF2G63016713 (SNP 31) | 31 | X | 72619011 | 0.9714 | 0.0286 | TATAGYTGGSCAATTAAATCTCCTATTCTTTTGTCTCAAAGG ATATTTGAAATTACATAG[T/C]TCTTTTTCTCATATAAAACC TACCATACAATCATTAGATGATCCTTCTTAGTTAATTTTTT |
| BICF2P276536 (SNP 32) | 32 | 8 | 3149437 | 0.966436 | 0.033564 | GATGCTGTGGGCCAGTCCAGAACCCACCTGAGAGAAACAAAC AGGCCTCTTTGCCAGCAG[A/G]GCAGCGTCAGTGTCACCCC TGTGACATGTCAGAACCTCCCTGAAAGTTCATCTAACCTCT |
| BICF2G63015658 (SNP 33) | 33 | X | 74531965 | 0.963018 | 0.036982 | GGCTCAGAAGAAAAATCAGCCCAGTTCACATCCAATGTTTCC ACACATCTAATCGTCTTG[A/G]GTTCAGAGGTAGATGTGGT ATCACTTAYATGGACACATATAACAGCTGGCCCCCACCTCT |
| BICF2P308749 (SNP 34) | 34 | 8 | 7325380 | 0.962032 | 0.037968 | gtttcagttaattatagtccttactggatccgattgctgtgg cgctaaaatgaAAGAAGG[T/C]Agggtacctgggtggctca ggggttgagaatctgcttttgactcaggtcatgatcccagg |
| BICF2P872820 (SNP 35) | 35 | 8 | 6388554 | 0.956114 | 0.043886 | CAGAGTAGCATTATTTTCTGCTGTATGAGGACACTTTTGTTA TATCCACAGTGGACAGAA[A/G]ACTGGGTTTTAGAACATGC TCAATTGAAACAAGACTGAGGGCTCACAAATTCCTGCTCCA |
| BICF2G63016210 (SNP 36) | 36 | X | 73592920 | 0.955084 | 0.044916 | TTACTTATTCATCTGAGACCAAGGCCACTGTGGTGAACCTAC AAAGCCTTACAAAGCAGG[A/G]CCAGAAGGGCACATAAATC ACTTGACTAACATTTGGTCAAAATAGCTCTTGGGCTCTTTT |
| BICF2G63016209 (SNP 37) | 37 | X | 73593955 | 0.049456 | 0.049456 | ATAAAATAAAAGAGCTATTAATAAGAACTCATAAAATCTAC ATAAATATAGTAACAGGT[T/C]AATATTCCCAGCATATTTT TACAAATCATCTATAAAGAGCATGAGAGCATATAGGGATTA |
| BICF2P1149405 (SNP 38) | 38 | 32 | 41212550 | 0.941321 | 0.058679 | GCAACAACCTGGTTTGTGTGTGGGAAGCTAATGCCTCCCCAA ATGCAGCAAACTCTCCTC[T/C]TGATTTTAGAAAAGCAGTT TAGTTACAGGCAAATGCATACATGCATGATAAATACTACTC |
| BICF2G63016173 (SNP 39) | 39 | X | 73672050 | 0.940828 | 0.059172 | GATTTTATAAAACATGATGACCTTGGCATTTATATAGTAGAT ATTACTACTCTGAAATTC[C/G]AGGAAGTATGATCATAAAC TCACACTTAATCTGGTAGAAGTATGGACAATGTATCAAAGG |
| BICF2P401962 (SNP 40) | 40 | 8 | 4495597 | 0.935897 | 0.064103 | CTTGGTTGAGTTAAAACATTTGCCCATGCAATTTAATGCATG TCCCTGTGGGGTTGGAAC[T/C]GACGTACACCCGAGCCAAC AGCCTTTCATGGCAGACGCCATCAGGCAGGTGACCCCCACC |
| BICF2P991264 (SNP 41) | 41 | 8 | 3165755 | 0.071992 | 0.071992 | CCTTCCACACGCTCAGGTTGGCACGGAGGGGGTGTCCTTGCC TGAGGGGTCCTGGCACAG[T/C]CATCAGGGCACACAGCTGA TAACCCAAGGGAGCAGTAGGCAAGACCTCATGGGCGCCGGG |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2S23230847 (SNP 42) | 42 | X | 58531292 | 0.079389 | 0.079389 | ATTCTCTTTGCTGTCTCCTGTATACAGAGATAAAAGCAAGAG TTTTCCCCTTCAGGTTTC[T/C]GAAACCCAGCTTCCTTTAG ATTTTAAGGGGTATTCTGTGTACCCATTTCCCACCTTCTGC |
| BICF2P1252842 (SNP 43) | 43 | 8 | 4618608 | 0.919132 | 0.080868 | GCGGGTTGGGACCCCCCCTTCTGCTGCTCCCACTTCAGAGTT GTGGCGTCACTAAGATGA[C/G]ACCTCATGTCGGGAACCTG AGAGTCCCTCGGGAGTTGTGcagggactgtagccgacctat |
| BICF2G63017198 (SNP 44) | 44 | X | 71984983 | 0.913947 | 0.086053 | ACATATGCACAGTGAATCGTGGATTGTTGTGTTTGATTTCTT ACATGATACAATAAAAGG[A/G]AAGTAGTTGAAGCAAACT TTAGTTTAAAGGAAACAATTTCTCTATCATAATGTTCAGTG |
| BICF2P1364202 (SNP 45) | 45 | 8 | 3175135 | 0.910256 | 0.089744 | CCCACAGACCCCAGGTGCTGACCACAGCAGCCACTTGGGCCC CCAATGCAGGAGACACCT[T/C]GGGAATGAAGGGGACAAGG CCAGCTCAGGCACATCGTCAGTGCACCTGATGGGAAGGCCG |
| BICF2P963708 (SNP 46) | 46 | 8 | 5472668 | 0.095945 | 0.095945 | ATCTGATCCTAGCCAATGGAAAGCAATTTGAGATAGGAATCA TATCTTGTTTTGGTTTAT[A/G]TGCTTTCTTTGGAGTTTTG CACATCATAGATAACTGTAAATTTGTAGAATAAATGTTTGA |
| BICF2S22939481 (SNP 47) | 47 | 8 | 7696228 | 0.098619 | 0.098619 | GTCAATGCCATTAACCTGGCGAAGCTGCTCGAGCATCCACTG CGATCTCCGCACGAACGA[T/C]GTGGAGCCTTCAAACTGTT TGACCTTCGTGATGGATGCTTGTGTGGGTTTCTTGTTTGTC |
| BICF2P1028186 (SNP 48) | 48 | 32 | 40758922 | 0.107495 | 0.107495 | ACTGGTTAATAAGACTTCACAGATTTTATCCATCATGTTGAT TATCTGTATATGTATTTT[T/C]TACCACTTAGGATAAAGTT CTGTTATCTGTAATTGATTCCAACCAGCATGTTTGCTCCAA |
| BICF2P19238 (SNP 49) | 49 | 32 | 40849057 | 0.892012 | 0.107988 | CTTCTTCTTTCCCATTGGATTCTTTCATCAATCGTAGGTAGT TCTTAATGAAGATCTGTG[A/G]TAAAGCCATTCATCTATTC ATTCAACAAATGGCATCACAGAAAAGAAAAATAACCTTTAT |
| BICF2P247312 (SNP 50) | 50 | 8 | 7825200 | 0.112426 | 0.112426 | GGGACACATTTCTGGACAGACCTCTGATCACACTCACAGGAC AGCAAGAGGAAGCTCTGG[A/G]TACAAGTACAGGGAAAAAA GAAAGAAATGGTCACAGGGAAGCTGCCGCAGGAAAAAGGTA |
| BICF2S23017118 (SNP 51) | 51 | 8 | 7615543 | 0.881164 | 0.118836 | GGGCAGATCCTCAGTGAGTATTGGCTCATGTTCTCCGAGGGA AGTAGAGTCCCAGAAGAA[A/G]GATGCTAAGGTGCCAAGAT TCCTGAGCCTGTGTGTGGTACAGTCACAGCAGTACTCCTGA |
| BICF2P132419 (SNP 52) | 52 | 32 | 35699747 | 0.874506 | 0.125494 | TCATCTCCATTTGTAATAGAAACCACATATATAGAGAGATTG GATTATTAACCACTAAAA[T/C]GTAGCCACTCAAGGGGAGG GGGGGAATGCATTTGGTTTATTTCCCATGTCAAAACAGAAT |
| BICF2S23115911 (SNP 53) | 53 | 32 | 40712955 | 0.873393 | 0.126607 | AACACTGCTAATAAATATTTATAATGGTTTGAGGAAAATATC AGGTGTGAGATGTCTTCA[T/C]ATCATATAATATATCATAA TATCCTCTAAAAAAGCTCTAAGCATAGGTCTATGGAACTCA |
| BICF2G630531773 (SNP 54) | 54 | X | 43502595 | 0.127219 | 0.127219 | AAGCAATCCAGGAGTCTTTCTCCGGGTAGCAGGCTCGCTTTA CAGGTTAAGGCTGGATGA[A/G]AAGGAAGAACCTGAGCTTC AAATTATCATCTGAGTAGAGCTGATACCCATGGTTACATTA |
| BICF2G630587826 (SNP 55) | 55 | 32 | 38771348 | 0.127838 | 0.127838 | GATTTTATTCTTTACTTTGATTTTTTTTAAGTTTTACTATGA TATTCAATATGATTGTGG[T/C]TCATGAGATTCCTCTTTTT AGCTGTATCATTAACTACAGAGCGTTCTCAAATATTTTTCT |
| BICF2P1007047 (SNP 56) | 56 | 8 | 4812890 | 0.87092 | 0.12908 | GTGGCCGGAGGGGTGGGCCCTACTGTGGCCCAGCTTCACGT CCCACTGGCCAAACATCA[A/G]GATGCAGACACCCAGGTCC CTTGTGCTGCCTGCTGAGGCTAGGAGCAGCGACTGGAAATG |
| BICF2G630531804 (SNP 57) | 57 | X | 43317321 | 0.869329 | 0.130671 | GATGGGAGACCTCATACACATGCAAAGATCACTATTAAAGAC TCTCGAGCAAAGATCGAA[T/C]GGACTGTGGCAAGCTGCCG CGCATGCCAATCAACAAATGCCTCCGACCATGGATCTAACC |
| BICF2S23632876 (SNP 58) | 58 | 8 | 5656863 | 0.866371 | 0.133629 | CAACAAGGTTTTTAAGGTTCTTTTCACTACCTTCTTCTTTTT GTACTTGCTTAGGACACC[T/C]GTATGTCTTCACAATATCA CCTGAAAGTCCTTTAGGAGATATACTCAAAAAATAAATAAA |
| BICF2G63015587 (SNP 59) | 59 | X | 75321307 | 0.865385 | 0.134615 | caacctgagctgaaggcagacactcaactgttgagctaccca ggtgtaccAAACACATCT[A/G]CTCTTAACCAAGCTTATTC TTTGCTATATTTGGCAAATTGTGGCATGTCTACAGTACTCA |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P482693 (SNP 60) | 60 | X | 43587959 | 0.864892 | 0.135108 | ATTCCCCATGTTTGAGGAAATCACAGGAGCCACTAGGAAATC AACCATTTCCCAACCAAC[T/C]TGATGATTTCCTGATCCAA AGGTTCTCCCAGGACAAATATGAGGTAGCCTTTCACACTCT |
| BICF2P940430 (SNP 61) | 61 | 32 | 40921126 | 0.136364 | 0.136364 | CAGTCTTGTAGGAGAGTAGATTGACTCACAGAACTGGCAAGA TTGGGAATCTGAGCATTG[T/C]CACTTGAGTCTTAAAACGT TTACGATTTTATTTCTAGTATTTCAATAAGAAACACATTCT |
| BICF2P786384 (SNP 62) | 62 | 32 | 36389913 | 0.136723 | 0.136723 | GAATACATTGCCAGAATAATTTCAAGTTCTCAAATCTCAACT AATAAGATTTTCGTTAAA[T/G]AAGGCATTCAATCATCACT TACTGACAACCCACAAAATTAGGCACTGATGAAAAATTAGC |
| BICF2P1340243 (SNP 63) | 63 | 32 | 41050914 | 0.150394 | 0.150394 | AAGTTAAGATATTCAAGAAAGAGAAGAGAGTGACTGAGCTAA AAAGAAAATCAGATCTCT[T/C]CCAGGCTTTAAAATAATCT CCACAATACTGGGCAATCCATGTAGTCTCCCCAGTTCCATT |
| BICF2S23626445 (SNP 64) | 64 | 32 | 36617978 | 0.153846 | 0.153846 | CTCAAAAGGAAAAGCCTGTGGAAAGGCAAAGAGGTATGTGAA AGAGGTAAGTTCAAAATG[C/G]TGACATGACCAGTGTACAT AGATTACAGGGTACTTGGAGGAGCAGTGAGAAAGGAGTCCA |
| BICF2P161586 (SNP 65) | 65 | 32 | 37795702 | 0.156312 | 0.156312 | TTCTATGAAATAGCTACCATTCTGGTTGGTATCTTCTGTTGA TTTAGATGATGAAGGAAG[T/C]ATAAGAAGTAAGGCTTATG AGTTTATAAAGCTTTAGTTAAAGCTTTGATTGTGACAAAGC |
| BICF2P579617 (SNP 66) | 66 | 32 | 36631235 | 0.162389 | 0.162389 | AGAGGAGAAAACACAGCTAAAAACTTTTTTACAGACTGGACA AAGGTGCTTACACTTTTC[A/G]TATTgggcagaatgagggg atgaaaacaccagtggtcttttttgaagccacacaaattcag |
| BICF2G63016280 (SNP 67) | 67 | X | 73386098 | 0.835968 | 0.164032 | AGGATGAATATTTATTAACAGTAAATATACATTTTTATTGTT CTATATACTCTAAAGACA[A/G]TTGTAGACAGTAAGATATA TCAATTTTAGAAACAGAAATAATGTTAATTGTATAATATGG |
| BICF2P721687 (SNP 68) | 68 | 32 | 40771787 | 0.829389 | 0.170611 | CAGGGATTCCTAAAGGGTGACATGGTATGGTCTAACACTTCC TCACTGTCCTTTTCCCAG[A/C]TGATATAAGAGGAGGACCA GAGAGACACATAAACTGTCTGAGTCTTTAGCATTGTGATAA |
| BICF2P504739 (SNP 69) | 69 | 32 | 37328946 | 0.827909 | 0.172091 | ACACTAATGGGTAGAGAATACACGTCCATCAGTCATCAATGT AATCTACTAACAGCCTCA[C/G]AGTCTGGCAGTTTTCAGTG AAAAGAGGAGTCATCTCCATTTATTCGAtcaatcagttgac |
| BICF2S23331874 (SNP 70) | 70 | 32 | 39390236 | 0.825444 | 0.174556 | TATTACCCTGCTCTCCAGCCACTCCTTTACCTTCCATTAGCC CACACCTGCTCTACACAC[T/C]ATTGCTCATGGAAGCCTTG CCACGTCCAGTCGCCACTCTGAAATGCCAGCATCCCTCCCA |
| BICF2P772765 (SNP 71) | 71 | 32 | 39278300 | 0.816075 | 0.183925 | TCTCAGATACTTGATAGCCAGCATTTCCCCCCATTTTCTTCC AAGAGCACGAAAGCATAG[A/G]AATGATATTCACATCTCGTA TGGTGAATGTGACACAGCCGTCAGTTGCGTTAGCTCTGCTT |
| BICF2S2318354 (SNP 72) | 72 | 32 | 35849858 | 0.18787 | 0.18787 | ACAGGAAGGAGAACTGAGCATCAAGAGAGTTCAGAACATGAT CATTGGGTCAGTTTGTGG[C/G]TGCATTAACTTTTCCCCAA AACAGAAAGCAACAGAGACTTCTGTAGGTCAGTCAACAGTG |
| BICF2G630588054 (SNP 73) | 73 | 32 | 38521693 | 0.810052 | 0.189948 | TTACCATTACTATAACCCAAGTTATAGTATACTATAACCAAG TCCTTAATTGACTTGATG[T/C]TTGTGCAGCTGATTTTAAA TCTATTTAGAATAATAGTTTACTTGTGACAATTCATATTAA |
| BICF2S23313445 (SNP 74) | 74 | 8 | 6343006 | 0.809665 | 0.190335 | TTGGTCGACTGACTGATTGGTTTTACTGTGGAGGAAAGAAAA GGGAATTTTCCCAAAGAG[A/G]ACAGAGAGAAAACATGGAA TTGAGCAAAGGGAGAATAGAGAGACAGGGCAGCCACTGAAG |
| BICF2P675334 (SNP 75) | 75 | 8 | 4477476 | 0.19428 | 0.19428 | TGCCTTATCCTCCAGCTCCTCCCTCACCATCTTGGAAACTAG CTCAAATGTCACTGGTAC[T/G]TGTCTTTCTTTTGATCTTT CTGAAAGACAAACATGATCCCATCACCTCTGCCTTTAGAAC |
| BICF2G63017409 (SNP 76) | 76 | X | 71722644 | 0.804241 | 0.195759 | ACTCCTAAGTAAAAGTTAAATTAACAGATTTGCCATCAAGTA CCTTGCCCATTTTTCCTA[T/C]AGATCGACTTTTTACTGGA TGATCCCCTTGATAATAATCTTGATCTATGTTTTAATTCCA |
| BICF2P798346 (SNP 77) | 77 | 8 | 4651519 | 0.195759 | 0.195759 | ctggtgggcttgtcaggggcaggatgttgtgtggtgagcaca gaattaaaactaggaGCT[T/C]gaagcgcctgggggggctca gttggttgacggactgccttcatctcaggtcatgatccctg |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P1150684 (SNP 78) | 78 | 8 | 7652070 | 0.802761 | 0.197239 | CATACAGCGAAGAGATAAAAACACAGGATGCTGGGCTCACGA CCATGACCGGAAAAGGAC[A/G]GCGAGGAAAAGCAAGTATG AGCAGCCCAAAGTCCTTTTTCCAGCACTGGCCATAGGAGGA |
| BICF2P1348758 (SNP 79) | 79 | 32 | 36083895 | 0.801579 | 0.198421 | CAGAGATGAGGAATCAGACTCCTCGTCCTCTGCTTCTCTACA ATGGCTCATGTTCTCCTT[T/C]CCCCTCAGCTGTTGCATTA ACAGAGGTCAACCCATTCTTCTAAATTTAAATCTCCCAGAA |
| BICF2G63017599 (SNP 80) | 80 | X | 71555277 | 0.198617 | 0.198617 | AATCAAACAAGTGCTAGAACATAGAACAAGTGGCTCATCTTT TCCCCAAATGTCTGGATA[A/G]GAAAAAAAAATCTAAACA AATGCTAGATGTTAAGTATCTGAAATGATCAGCCCATGAAA |
| BICF2G63016090 (SNP 81) | 81 | X | 73800072 | 0.200197 | 0.200197 | TCCATACCAGTCCTTGTTGTCTACCCCGAACTTCACCTCTCT AGGCACAGACAGCTCTAA[A/C]TTTCACTCATAGGTATCT ATGCTGACCTGGCCTGCCTCCtgttttgttttgttttgttt |
| BICF2S23524027 (SNP 82) | 82 | X | 64785623 | 0.79931 | 0.20069 | CAAAAAATTCCCTGAGCCCAGCATCAAGGTACCTGGTTTGGA GTGGGTGGGTCCTCAGAA[A/C]GAATGGGTGTGGTGTACAT TTAGCAAGTTATGTAGCATGTGTCTGTGTAGTCTCACCTCT |
| BICF2P591872 (SNP 83) | 83 | X | 62989720 | 0.795252 | 0.204748 | GGGCCCAGCAAGTGGCAGAACTGGGAAGACCCCCTCTTCTTC CGCCTGGAGCAGTGGTGT[A/G]GCAGCACACCACAGGAGTC TGAAAGGGTGGGGAGTCCAAACGGGAACATATACCTGAGAT |
| BICF2G630587712 (SNP 84) | 84 | 32 | 38968302 | 0.794379 | 0.205621 | atataatataacttatttaaaatatttGAAGATATTTCTATA GTTATGCTCTACCATTTG[T/C]TATTATAAGATTTCCAACA GCTTACTTCTTGTATGAAATTAATTTACCAGCCCCTCACCT |
| BICF2G630587722 (SNP 85) | 85 | 32 | 38964413 | 0.792899 | 0.207101 | CCCTATTCTATAAACATTCCCTCTCTGGCCATCCTGTCAAGT GGGCCCTGACAGTGTGCC[C/G]CAGAAGCTCCCTAGCCTTT GCCCATTCCAGCTATGGCTAGCCTGCCACCAGCCATACACA |
| BICF2G63018557 (SNP 86) | 86 | X | 66396513 | 0.218164 | 0.218164 | CACTGTGAGGTCTGAATGGAGACATTCATGATAGACTCCAGG ATTTTCCCAGCTATTAAG[T/C]CATGGGCCATAAACTGGAA CACTTGGAAACAGTCCATAGGTTCATATTAAAGAATATGTT |
| BICF2P652606 (SNP 87) | 87 | 32 | 37855796 | 0.776134 | 0.223866 | GCAAAAGGAACATGAGTTCTGATCTTCTGTAAAGGAGGCTAA TTTACTAATGGTCATAAC[T/C]GTGGcctgagggtcaagtt tctaattaaacgtgcatcttggggYggactagaatactttc |
| BICF2S23312799 (SNP 88) | 88 | 32 | 36791310 | 0.224852 | 0.224852 | CAAGGSCCAGGTACCCTGAAGGAGTCCGCTTCACCCAGGCAT GATGTGTTTGACAGTCTT[T/C]GTAATTGATACAGCCATTG GCATCCTCTTGCGGCCAAYATCAGCTCCACTTCAACCTCGG |
| BICF2S2303948 (SNP 89) | 89 | 8 | 5896281 | 0.773669 | 0.226331 | TGCAATGGGTTTTGAAATTAGAGGACATCACAGCAGAGTAGA ATGGTTTGGAACAGGGGA[A/G]TATGATTAGGATTAATGAG ATGAAAGAAAATTCTGGCTAGAGGGCTAGAAGAGCCATGGA |
| BICF2P506595 (SNP 90) | 90 | 8 | 4886813 | 0.228304 | 0.228304 | CTCAGAACTAGATAGGCTAATAAGTGATAGGCCTTGTGTTTT CCTAGAGTGTGCTTTAAA[A/G]GTTTCTTAAGCTAAAAAAT TACATTCGTGAGAAAATTGAAATAAAAGGAAAACAGTCATG |
| BICF2S23130600 (SNP 91) | 91 | 8 | 5180802 | 0.228304 | 0.228304 | GATACTTTGGGCTCTGGGTGGGAGCCAGCAGTGGTGGGGCAG GGCAGGAGTCCAGCAAGG[T/C]GTCTGGGCATACATGTCTG AGAGTAGGAAAACCACACCATTGCACCTTGCCTTTGACTTC |
| BICF2P1270451 (SNP 92) | 92 | 8 | 5580117 | 0.229783 | 0.229783 | TCAAGGATCAGAAAAATAAAAGCAAAGAAAGAGGCAAAGAAA GAAGAAATGAAATACCTA[A/G]TGGCAGAAGTAGGCAGAGA AATAAAGGCTAAAGAAAATGGCAGAGGATTGTTTGAAAGG |
| BICF2G630588267 (SNP 93) | 93 | 32 | 37876000 | 0.23001 | 0.23001 | TATGTTATACTATTTTAGTATCTTAATAAATATGATTAGCCA AAATAGTTTTATCATCCT[C/G]AAAAGTGCAGCATATATTA TTTTCTATTAAATTCAGAATAGGTATAAACTAGAAAGCATT |
| BICF2S23122074 (SNP 94) | 94 | 8 | 4965974 | 0.76999 | 0.23001 | ACAGCAGTTCTGAGGATGGACTCGCAGAGGCTCCTGACAAGC AGAATGACCAGGCCGAGC[A/G]GAAAGGTCAGTGCTGCCAG TCTAGCCAGAAGTGGGGGAGAGAGGATGTAGGAGCAGTACT |
| BICF2P555643 (SNP 95) | 95 | 32 | 40258722 | 0.230769 | 0.230769 | ACTGTACTCAAAAAGTTCTGTTTGCCTAAATGGGATCAGCC TCTAATGATGCCAGTGA[T/C]GGGAGGCTGTTCATCATCC CTTCGGGATAATTCAGAGCCTAGGCAGAGGCCCAGCGTTCA |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2S23259999 (SNP 96) | 96 | 8 | 4990277 | 0.231732 | 0.231732 | TACAGGCCCCAGGAAGGAGCCACCAGATGCCCAGGACTGGGC CCAGGAATGATGGAGGCT[A/G]TACAGCTGGCTGCCTGCAC TGGCTGCCGCCCCTGTCATCCAGTGTCACAGAGCAGCACCT |
| BICF2G63016525 (SNP 97) | 97 | X | 72989415 | 0.251482 | 0.251482 | AGACATTGCCAAGAAGTATCCACAATGAACAGTTTGAAGGGG ATCCAGAAAAGCACAGGG[T/C]CTACTTCCGCTGGATGAGC AGCAGTGAGAACCACAGTCAGGTAGGTCTTAAAGCAAAGTT |
| BICF2G63019552 (SNP 98) | 98 | X | 60108249 | 0.737179 | 0.262821 | GCTTTGAAAACCAACAGGAAATACATCCAGGAAAGCTATACA ACTGTGGTGAAAGGAAAG[A/G]AAAATCTGCTCTTAAAGG TTGTGTGCAGACTCACTTGCCCCAGAAACCAGTGCGAAAAC |
| BICF2G63017884 (SNP 99) | 99 | X | 70145192 | 0.271019 | 0.271019 | GAGATGTGTAAAATTTAATAGAAATGAAACTTGCCAAAACAG ACCTCTGTACTCGTCAGC[A/G]TTCTAAGTCCATCTTTCTG TAGCATGTAAGTAGAATAATGTTCTATTAATTTCCTCTATG |
| BICF2G630587598 (SNP 100) | 100 | 32 | 39023585 | 0.706931 | 0.293069 | GTTCTTTCTATTCTATCACACATACCACCCCCCTGCCCACAG TACCCCTTTCTGCCATGT[T/C]TCAGACTCCTACACAAGAG GTTCTCTCTCCTGGCTTCCAGTTAGACAGGCAGGTAAAGCT |
| BICF2P285901 (SNP 101) | 101 | 8 | 6743491 | 0.70069 | 0.29931 | TAAAAAAATACAACAGTAGCATTAGAAGACATGCTAAGCGGC TGTATTAGAGAAGGTTAG[T/C]GCTGGCCTGAAGTTTAGAA ACCTTCCCTTCTCTTTTTTTTTCCTTCCCTTCTCTTTAA |
| BICF2P811511 (SNP 102) | 102 | 32 | 36167454 | 0.30583 | 0.30583 | TCAAGAGTACTAGAGCATCTATAATCAATGGTAAATTGGGA ACTAGTGAAACAAGTTTA[T/C]AGGACAAATAACATAAATA AGGATTTTTTTTAAATTTGGAAAATTGTGGAATAATGATA |
| BICF2P1146265 (SNP 103) | 103 | X | 63433179 | 0.693725 | 0.306275 | AGAATTCAATTTTGGGGAGCCAGGAAAACAGATTAGTTTTCC AAAGGGAAGTGCCATTTG[T/C]ATCTATCCCGGTGGGGCTG CCAAGAATTCCCTGGGGTGGGAGACGGCGCTTCTGTGGATT |
| BICF2P243607 (SNP 104) | 104 | X | 57821508 | 0.690523 | 0.309477 | CACCAGAGAGCCCCGCAAGATCATACTGCACAAGGGCTCCAC TGGCCTGGGCTTCAACAT[T/C]GTAGGAGGAGAGGATGGAG AAGGCATTTTGTTTCCTTCATCCTGGCAGGAGGCCCAGCT |
| BICF2P382932 (SNP 105) | 105 | X | 64010327 | 0.690335 | 0.309665 | TGGTGATGATTTATCCCCATGTTCAAGATTTATCCTCCCTG TCTCAAGAAATCATGTCA[T/C]TACAGGCATCCTTAAAGTC ACAAGACTGGGAAGTAAATACTGATGAGGTCCAAGACCTGG |
| BICF2P1061734 (SNP 106) | 106 | X | 57654632 | 0.69003 | 0.30997 | AGCATAGTGTACCCACATATAAGGTCACATCTGAGGCCAGGG AGTCGGGGTCTTGAAGAT[T/G]ATGACTGATCATGTGCTTG AGGATGATGATGATCATGTGCTTTTCCTGGCTGTGCAGTTG |
| BICF2S22937235 (SNP 107) | 107 | X | 57492668 | 0.310158 | 0.310158 | gtgtgtgtgtgtgtgtgtgtgtTTAATTCTTTGTGAGAAG CCCCTCATTTTGACCTAA[A/G]TTTGGTAGAGGCCCCAGGG GATCGAGAGGAGAACAAAAGGATAAACCATTTGCTGTTCA |
| BICF2S22937489 (SNP 108) | 108 | X | 73723672 | 0.687068 | 0.312932 | CCAACTTTCACTAGCATCACAGCCCCTATCAATCTCTGTTCT TTTTTCTGTCAGTACCAT[A/G]TTTGCTCCTACTACATCYA ATCTGTGAGCTCACAGGATGAGGACCAACAGCTGCCCTGAG |
| BICF2P903726 (SNP 109) | 109 | 32 | 40883681 | 0.329389 | 0.329389 | TGTCTTACCTCTCTCTATTCCCTTGTCCATAGTAGTATTAAA TATATCTTCCTGAACACA[A/G]ATCTGATCCAGTCTCTTTT TGTAATTAAAAGCCTTTGCTAGCTTTGGTGATCACCTCCAG |
| BICF2P1324008 (SNP 110) | 110 | 32 | 40043909 | 0.664179 | 0.335821 | GACCTGACAGATTATGTAGACTTTGTTTTCAAAGGGAGCACC TGCTGGATATACAACATG[A/G]CACTAAATTGTGCTCCACA TCCTTGGCAGAGGTGGGGGGCGGGGCACAAAGGAAGAAACC |
| BICF2P320425 (SNP 111) | 111 | 8 | 7105593 | 0.336283 | 0.336283 | CAGAGGAAAGGAGAAGGTCCCACTTAGGGGACTGGAGAGGA GTGGGGGAACATCACCAG[A/C]GCCTTCCTGAGCCAGGCCC CCTGTGGGGAGAAGCTCTCCCCAGGACTGGGTGCCTTTGAA |
| BICF2S23210713 (SNP 112) | 112 | 8 | 6397309 | 0.634615 | 0.365385 | tcctccctctccccatcccattctcatgcaagtgtgctctc tctctAAAACACCCCCCC[A/C]CACACACACACACAGACAC AACCAAAtttgggtctcaatgtcttgaccaaggaaaaggca |
| BICF2G63018424 (SNP 113) | 113 | X | 66756995 | 0.367793 | 0.367793 | gagaagaaggaggagaaagaggaaaagTATATTTGATGGAAT GAAAAACAAGAGTTCAAT[T/C]CACTCTGGTCTGGGGTGA CCACTATTAGTCCTTCAACATCTTCCTTGAAGGAATTTTAA |

TABLE IV-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2G63015897 (SNP 114) | 114 | X | 74179959 | 0.631164 | 0.368836 | CTGGAATTCTGTCAGATCAACATTCAGAGCTCCATCAAATCT GAGGGAAGCAGTGATAGA[A/G]GATACAATTTGACCTTTCA GTCTATTCAGGTTCATGTAGGTTAGGCATTCAATATCAAAG |
| BICF2P305287 (SNP 115) | 115 | 8 | 3258209 | 0.371175 | 0.371175 | CCACATGTGGTTACACCACTGTGTTATCCTTCCACCTGTCCC ATCAACCCACCCGCACAT[A/G]TCACAGTGCCTCTGTCCTC AAAGAACACTGTATCCAACACCTCCACATCCTCTCAGCATG |
| BICF2G63016662 (SNP 116) | 116 | X | 72647220 | 0.615878 | 0.384122 | ATTCCTATGGTGGGCGCTGCACATTTCCTCCCAGGGGAAGGG CAAGGGTCCTGCATTTCT[A/G]TGCTTTCCAGGGCCTCCGC ACCAAGAGCAATTGCTAGGTCACGCATGCCCCTGCACTTCC |
| BICF2G63017854 (SNP 117) | 117 | X | 70302610 | 0.606541 | 0.393459 | CATGTCATCACTAACTAATTTATTAACAAGAGTTTTATTCTT TGAAAAACAAAATCACTC[A/G]CATTACTCAGTTGCTTATT CCTTGATTCATATACAAATGACTGATAACATGAGATAAAAA |
| BICF2P170917 (SNP 118) | 118 | 32 | 38039478 | 0.600592 | 0.399408 | GATGATTTAGTTGTTTGAATGATCTGGCATATAAATCTTCCA AATCTGTGTCCATTGGAT[T/C]GCTTACAGTTTAATCTTTT TATTTCTTCCCAGAATCACATTTTTTCATTATTTATCTTTG |
| BICF2G630588207 (SNP 119) | 119 | 32 | 38333881 | 0.425201 | 0.425201 | AGTTAAATTCTGTGAATAACTAGAATCCGTTATACTTTTTCT GAAATGAAGTCTGTAGGC[A/T]TTTCAACAGCAAAAGGAAT TCTGWTTTTYAAAACTATACATAATGCTTCTTAAAAGCCCT |
| BICF2P702899 (SNP 120) | 120 | 32 | 39207136 | 0.428854 | 0.428854 | AATGCCAACTTTAAAAACGCATTCAAGGTTTTCCTCTGTAAA TGCATTCCTCATTTTGGA[T/C]GTGATGTAAAATCTTATTC AGTGTTTTGTTTTTTTTCCCCCCACAGGTCTCAACAATTA |
| BICF2P1388432 (SNP 121) | 121 | 8 | 7178740 | 0.446203 | 0.446203 | GGTGGGACCGGCCATCAGCAGGCGGGCCAGCGCCCCACAGAT GTTGTCACGGACCCGATC[A/G]TGGCGCTCCCGTGCCAGGA GGGCAACAGAAGCCCCAGCAGCTTGGGGAAGTATCTGGTT |
| BICF2P588571 (SNP 122) | 122 | 32 | 37214320 | 0.454635 | 0.454635 | AGGGGACTTGTGCTAATCACTGGGCAAATTTTATGAACTTCT GAATTTTAAAGCAAAAGA[A/G]AAGGTGAAAGAATGGAAAG AAGGTGTGAGTGTTTGAGGAAAACTTCTTCTTTGGGGTTGA |
| BICF2S22912518 (SNP 123) | 123 | 8 | 6934693 | 0.544872 | 0.455128 | TACACAAGCAAGGCAGTATGCCCTGTCTCCTTCCCTTGGGCC ACCTGCACTTAGACATGG[T/C]AGGTTCCAGTGATGTGTCT AGTCTCTAGCAAGCAGGGCTTGCTTCTGCTCTATCCATCCA |
| BICF2P223099 (SNP 124) | 124 | 8 | 7427438 | 0.530602 | 0.469398 | CTGTCCTTGGTCTGGACCTGCTGTGAAGACCAAGTGCTTCCT GAGATCTCTCTGAGTCTA[A/G]TTTCCAGAGCAGTGAGTGA GAAATGAAATGAGCCGAGGATTGCCCTCCCTCCTATGGACT |
| BICF2P568891 (SNP 125) | 125 | 8 | 7938712 | 0.475321 | 0.475321 | TAAGCCATCAGCATGGGCTCCTAGGGGTCTGTTCAACTCCCT TGTGGTGTCTTACTGCTC[A/G]AGCAAAGGAACAGTCTGGT ACAGTGGGAGCAAGAGCTGAGGTTGGAGAGTGGGGACACAG |
| BICF2G63019507 (SNP 126) | 126 | X | 60714796 | 0.521308 | 0.478692 | GAGGAGGTGGAAGTGATTAAGTTTAAAATTTCTGGGGTGGTT TCTGGCGACATGAAGCTG[A/C]GAGCTAGAATGCCTTTCAA TCTCATAATTTCTTTAATTTGGTGATTATACCAGAGCCACA |
| BICF2P814468 (SNP 127) | 127 | 32 | 37551101 | 0.517787 | 0.482213 | CCTGACAAACACTACCTCTGCTCTTCAAAAGCAATAAGCATT TATTCTGTGACACATTTA[A/G]ATACAAAGTCAATTACAAT AGAGTATAAGTACAATACTAGGGAAAGTACAAAGTCATAYG |
| BICF2P948321 (SNP 128) | 128 | 32 | 37526448 | 0.511834 | 0.488166 | GCATGATGAAATCAGAAAAGTATGTAAGTTTCTAGAAGAAG CTAGATATATGGTAACTT[A/T]GGTCAAATAGAACCATGTA GTGAAAAGAATATGAGTTTTCAAGTTCAATAAAAAACAAAA |
| BICF2P807378 (SNP 129) | 129 | 32 | 37648000 | 0.510848 | 0.489152 | ATGCATAAGTTTCCAAAAGAGTTCAGGATTCCAAAATAAAAG CTTCACTAAAAGATTCAT[A/C]GCAAAAGAGTAATGAACAA TTAAAGTCATAGGATATCTAAAATGAAAAACTGTTAGACTG |
| BICF2P175415 (SNP 130) | 130 | 8 | 6494289 | 0.489645 | 0.489645 | AGATGGCTTAGTTGTTTCTCTTTCCTCCTGAAGTCCACAGCT TAGTTACTTGGACTCTCC[A/G]AAATaggatcgttggacat ttgaggaaagctctagcatgaaagccatagactaaaaaaca |

Example 2

Identification of Further SNPs Associated with Susceptibility to Liver Copper Accumulation and a Protective SNP The three genes identified in Example 1 were investigated to identify further SNPs associated with susceptibility to liver copper accumulation. Thirty-three amplicons covering every exon of the three identified genes were chosen. These were amplified in 72 samples of genomic DNA from dogs of the Labrador Retriever breed. The samples were taken from dogs with either high copper (liver levels of copper above 600 mg/kg) or normal copper liver levels (below 400 mg/kg). The amplified product was sequenced in both directions by the Sanger method. The software 'Seqman 4.0' supplied by DNASTAR was used to assemble the sequence in each amplicon. The assembly was then examined to find single base variations (SNPs). These variations were then genotyped by examining the base-intensity at the SNP in the sequence from both directions. If the genotypes of a SNP from the two directions disagreed in more than 10 samples the SNP was classed as an artefact and ignored. The identified susceptibility SNPs are set out in Table V.

Surprisingly, a protective SNP was also discovered. This is provided in Table VI. This SNP is in the coding region of the ATP7A gene (an X chromosome-linked gene) and results in a change in the coding sequence. A study of average liver copper levels by gender and ATP7A genotype was conducted (Table VII). FIG. 5 illustrates the data from Table VII graphically. FIG. 6 illustrates the same data as copper-histological scores. The p-value (0.000396) was determined from a Kruskal-Wallis test on the histological score with gender-genotype as the groups. It is clear from the data that the presence of the T allele is indicative of a dog being protected from high liver copper.

The results may explain the female bias of chronic hepatitis. Male dogs have only one copy of the X chromosome and so are hemizygous at the ATP7A locus. An X-linked recessive gene-effect is more likely to be seen in males than females because of the hemizygous state of the male X chromosome. The protective effect here is recessive so we see more cases in the female population.

The protective SNP results in a change of a Threonine to Isoleucine at amino acid 328 of ATP7A leading to a decrease in the number of potential hydrogen bonds from 3 to 0 and an increase in hydrophobicity, potentially altering the shape of the protein. The Threonine at this position is conserved across many mammals, including horse, human, chimpanzee and dolphin, indicating the importance of this amino acid in the function of the protein.

Example 3

Investigation into Breed and Geographic Diversity of the ATP7A Protective SNP The ATP7A SNP in Table VI was genotyped in samples of DNA from dogs of other breeds in addition to Labrador Retriever to determine whether the SNP is present in other breeds. Table VIII show the results, with the number of dogs of each genotype. The 'T' column refers to homozygote females (TT) and hemizygote males (T). The results demonstrate that the SNP is present in diverse dog breeds and therefore may be used as in indicator of protection from copper accumulation in a wide variety of different breeds, mixed bred dogs and mongrels. The T allele of the SNP has also been found in US and Japanese Labrador populations, demonstrating that geographical location of the dog is not a hindrance to the utility of the SNP.

TABLE V

Sequence of further SNPs indicative of susceptibility to liver copper accumulation.

| SNP name (SNP no.) | SEQ ID NO: | Sequence to the Left of the SNP | First Allele | Second Allele | Sequence to Right of the SNP |
| --- | --- | --- | --- | --- | --- |
| ATP7a_Reg4_F_9 (SNP 131) | 131 | CTCTCATTTTGTGTATTGATTTGAG GACTCTGTCCTTTTTGTTCTCTTAG GTGTTTTGTAACCATTTTTGTGGTT CTTGCCACAAAAGGCCTTATGAAGT CCTGCATATGAGTGATGTGCAGGAC AACTTTGACTTTCTGACAGCCAGTT TTTGTGTTTTGTT | A | C | CCTTAGTTCCCAAGTTCCTATCTTG TTTACCTCATGATCACATTTTAATA TCAATGAAATTTGTAGGAAAACAGC AGAAGGAAAGATATAAGGTTACTAT TCTCTATGGACCTTGGTTG |
| UBL5_Reg1F_16 (SNP 132) | 132 | TTGCAGATTATATGATAAATATAGT TGTAGCTTCAAAAATGACTATAACG AACAGAAAAAATTAACTTATCAAA AACTTTTCAAATTTCCCCATA | T | C | ACTTAACTAGGTAGGCCACAGAGTA TGATAGTATGCAAGTTATTAAAATC TGTTAGCAAGGCATAACACATATAT TTCTACTTAATGAGGTTTCTATAAT CAAGGCTTGTCAAGTCCATTATGTT C |
| golga5_Reg1_24 (SNP 133) | 133 | TCAGACTGAATCTAAAGCCACATAT ATTTCCTCAGCAGCTGATAACATTA GAAATCAGAAAGCCACTAT | C | T | TTAGCTGGCACCGCAAATGTAAAAG TAGGCTCTAGGACGCCAGTGGAGGC TTCCCATCCTATTGAAAATGCATCT GTTCCTAGGCCA |
| golga5_26 (SNP 134) | 134 | TCTTGTGCTTGTTCTTTATCACCAT TCATTCAGTACATCCAAATTTTGAA ATCCTTAGAGCTCTATAGCCTCTAT GTAGGAGAATGA | G | A | ATTTCATCAAAAGGAAATATTTTGA GAATTTAAGTGATTTTTTTATGATA TTTTAGCTATAGCAGTCACCTTGAG CCAAAAGACATTCTAC |
| golga5_27 (SNP 135) | 135 | AAAAATATACTCTCTTTCTTACAGA AACCTCTAATAATTCAGATTCTGGC CATGAAGTTCAGGAGGATTCTTCAA AGGAAAATGTATCATCAAGTGCTGC CTC | T | C | ACTGACCACAACCCAACACCTACTC ATGATGGCAAATCMCMTRAACTGTY TAWTYTCSGATTGGRRAWTMAAYKG TTRAGGAATGAA |

TABLE V-continued

Sequence of further SNPs indicative of susceptibility to liver copper accumulation.

| SNP name (SNP no.) | SEQ ID NO: | Sequence to the Left of the SNP | First Allele | Second Allele | Sequence to Right of the SNP |
|---|---|---|---|---|---|
| golga5_28 (SNP 136) | 136 | TTTGCCCAAGAAAAATGAAGACCTA TGACCATGGAAAGACTTGATACATA ATGCTGGAGTACTAGTAGTCAGACC CACCCAAGTCTTTTCACGTGTTCAT TCAGTATAGATGCGGCACACGTTGG CTGAGTCCCTCCG | T | G | TGTGTCAGGAACTGTTTTAGGTATT GGGGATGAAGTAGGGAACACTGATT TAGSTTCTGTTTATTCATGTCTCAC TTTGTAGGAATTYCMHTAMATAGAA RAADA |
| golga5_29 (SNP 137) | 137 | TCTCAGTACTCACAGGTACTTACAA ATACAACACTAAGAGGTTTCACAAA ACAGTACTCTTACATAGCACATGCT GTACTCTCTGTTCCATTCTATTTTA TTACTATTTTAAAATATGGATTGTG AT | C | T | TGCCAAKTTGATTCTCTGGCCCATT AATAGTTTGAAAATCTCTTCTGTAG GAGTATAGGAATTACCACAGAGTTT TGAGAAATTGATGAATGCCACGCTT TACCTGTGGGAACGTAGATTCTA |
| golga5_30 (SNP 138) | 138 | CAGATGATGAGTCTGGAGCTGGTGA TCTGGGCTGGAGATAATGAACCTGG GAGTCATCAGCTTTGGAGA- AAGGGTGTCTGGCCTCACTCTTGCT | T | A | GCACAGAAAGAAAGTGCTCATTAGT GTCAACTCTCAGCAACACTTGGTAT TTGTAAACTTTAATTTTTGCTGACT TCATGGAGAAATAATGTTTTT |
| golga5_31 (SNP 139) | 139 | TAATGATACAGAAATGAATTTGGCA GGAATGTATGGAAAAGTCCGAAAAG CTGCTAGTTCAATTGACCAGTTTAG GTAAGCAAGTGCAGTACTGGTGAGG AATGG | G | T | GCATCGGCTCCTTCTGTGCTATTTT CCGGTGGCTCCAGTCACAGCCCCAT CAAGCAGAGCTGATACCTAAAGTGA CATTTACCCTACTTCCTCTCTCAAT |
| atp7areg17_32 (SNP 140) | 140 | CATCACTTAAAATCATCTCAGCAAG TGTTGTTGAAGATGATTTTTTATAA AGTATATTCCAATCTTATTCTATAC TTCAGAAGCTTGGAATTCT | T | C | ATTTGCTTTGCTGGATTGAAAAAGT CTGGAAGTAATTAGAATGACTTCTC ATACTCCCACCTTGAATTCTCCTAA TATCAAAGGCTGGGAG |
| atp7areg17_33 (SNP 141) | 141 | ATATGGAGAAATGAGCTCTTATACA CTTTCAGTGGACATGTAAACTGTTA TTGTCTTTTTGGAGAGCATTTGGCA GGATCTATCAAAGT | G | A | CACACATCATTTGATTGAGCAATTC CACTTCCAGCCATATTCTGGACATA ATTTACAAGTATAAAAAGATGCATG TTT-GA |

TABLE VI

Sequence of SNP indicative of protection from liver copper accumulation.

| SNP name (SNP no.) | SEQ ID NO: | Comment | Sequence to the Left of the SNP | Wild type Allele | Alternative Allele | Sequence to Right of the SNP |
|---|---|---|---|---|---|---|
| ATP7a_Reg3_F6 (SNP 142) | 142 | coding change, protective T | AAATATTGAAAGTGCTTTATCTACA CTCCAATATGTAAGCAGCATAGTAG TTTCTTTAGAGAATAGATCTGCCAT AGTAAAGTACAATGCAAGCTTAGTC A | C | T | TCCAGAAACCCTGAGAAAAGCAATA GAGGCCATATCACCAGGACAATACA GAGTTAGTATTGCTAGTGAAGTTGA GAGTACCTCAAACTCTCCCTCCAGC TCACCTCTTCA |

TABLE VII

| Gender | Genotype | Average Copper Level | Count |
|---|---|---|---|
| Females | TT | 323.3 | 3 |
|  | CT | 818.3 | 22 |
|  | CC | 1041.3 | 45 |
| Males | T | 437.5 | 13 |
|  | C | 905.8 | 34 |

TABLE VIII

| Breed | C | CT | T (Mutant associated with low copper levels) |
|---|---|---|---|
| Labrador Retriever | 31 | 13 | 28 |
| Miniature Poodle | 3 | 2 | 8 |
| Golden Retriever | 0 | 0 | 1 |

Example 4

Discovery of a Further Protective, but Non-Coding SNP

Sequencing the ATP7A gene revealed an intronic SNP that is almost in complete linkage disequilibrium with coding SNP ATP7a_Reg3_F_6. Like the coding SNP, the intronic SNP (ATP7a_Reg 16_F42) is significantly associated with protection from liver copper accumulation (Table IX). The significance of both was measured using a chi-squared with two degrees of freedom on the independence of genotype and disease status. Disease status was positive for >600 mg/kg dry liver weight copper quantification and >=2.5 histology score; negative for <400 mg/kg dry liver weight copper quantification and <2.5 histology score. The expected table was based upon a Bayesian estimate of genotype frequencies and disease frequency within the sample assuming independence of the two variables.

The calculated measures of linkage disequilibrium between the non-coding SNP and the coding SNP are: D'=0.93 and R-squared=0.86. The SNPs are therefore almost in complete disequilibrium.

The sequence surrounding ATP7a_Reg 16_F42 is shown in Table X.

TABLE IX

| Amplicon name | SNP position | Exonic or intronic | Coding change | Amino acid number | Base in Genbank | Base change to | Amino Acid in Genbank | Amino Acid change to | Association with phenotype |
|---|---|---|---|---|---|---|---|---|---|
| ATP7A Reg 3 | ATP7A 30,374 | Exonic | Yes | 328 | C | T | T | I | 0.001669996 |
| ATP7A Reg 16 | ATP7A 89,705 | Intronic | No | NA | C | T | NA | NA | 0.001796187 |

TABLE X

Sequence of SNP indicative of protection from liver copper accumulation.

| SNP name (SNP no.) | SEQ ID NO: | Comment | Sequence to the Left of the SNP | Wild type Allele | Alternative Allele | Sequence to Right of the SNP |
|---|---|---|---|---|---|---|
| ATP7a_Reg16_F_42 (SNP 143) | 143 | Intronic, protective | TTAAAATAACTACTTGCAGTGATTTCTTTCCCCCAGTATAAAATGTCAGTTTTGTCTCAATCCACCC | C | T | CTTCACCTTAAAAAGAAAAAGAAAGTATTAGTTTTCAGTGTCATTTGCCTTAAAATG |

Example 5

In Vitro Experiments Conducted to Determine the Functional Effect of the Coding Mutation ("ATP7A SNP")

Materials and Methods
Cell Lines

The canine dermal fibroblast cells CDFIB44, CDFIB62 and CDFIB111 were isolated from euthanized female Labradors. Blood samples, taken prior to euthanizing were subject to the genetic test of the invention to ascertain increased risk to the disease. CDFIB111 was homozygous for the ATP7A SNP and CDFIB62 was heterozygote. CDFIB42 was used as a control. These cells are referred to as ATP7A$^{C/C}$, ATP7A$^{C/T}$ or ATP7A$^{T/T}$ corresponding to canine dermal fibroblasts expressing wildtype, heterozygote or variant forms of ATP7A. The human dermal fibroblast cells HB156 were obtained from a clinical Menkes patient (ATAC). H8881 cells were used as a control. ATP7A has not been presently sequenced in these cells. No information regarding ATP7A sequence is available regarding these cells.

Fibroblast cultures were routinely maintained in Dulbecco's modified Eagle's media (Invitrogen) supplemented with L glutamine (2 mM), 10% FBS, MEM non essential amino acids (100 µM) and penicillin/streptomycin at 37° C. in a humidified atmosphere of 5% CO2 in air. Low serum media contained identical components with 2% FBS. For the experiments, canine cells were used between passage 4 and 9. Tissue from the small intestine and liver was isolated and stored in RNA later at 20° C. until needed.

Immunofluorescence

For immunofluorescence, microscopy cells grown on glass coverslips were incubated in low serum media with 200 mM bathocuproine disulfonic acid (BCS; Sigma) for 24 hr. The cells were fixed in freshly prepared 4% paraformaldehyde in PBS for 20 min, washed and permeabilized in 0.2% Triton-X100 in PBS. Nonspecific signals were blocked with 3% BSA in PBS containing 0.2% Triton-X100 for 1 hr, followed by incubations in the same blocking media containing chicken anti ATP7A (1:50; ab13995 (Abeam), against the amino acids 1407-1500)+mouse anti 58 k (1:50; Abeam) for 2 hr. Texas red-conjugated goat anti-chicken (1:100) and FITC-conjugated donkey anti-mouse (1:100) antibodies (Abeam) were used to detect the primary antibodies (1 hr). Texas red conjugated rabbit anti-goat antibodies (1:1000; Abcam) were subsequently used to amplify the signal from the goat anti-chicken secondary antibodies (1 hr). The coverslips were finally mounted in Prolong Anti-fade gold (Sigma) and viewed via epifluorescence.

Radio Isotope Experiments

The 64Copper isotope was made using metallic copper wire (3.3 mg) that was irradiated over night in a reactor providing an induced activity of approximately 170 MBq·mg$^{-1}$. Upon arrival, approximately four hours after irradiation and 30 minutes prior to the start of the study, the copper wire was dissolved in 50 µl concentrated HNO3 (10.3 M) and neutralized with 1.3 ml 0.5 M NaOH. DMEM media was added to a final concentration of 4.7 mM copper. Fibroblast cells were plated in duplicate in 6 well plates in 5% FBS supplemented DMEM media plus additives.

For copper treatment, cells were incubated in 10, 50, and 100 µM copper for 24 or 48 h. After treatment, media was removed and cells were washed four times with Flanks supplemented with an equal amount of cold CuCl$_2$. After washing, 325 p. 1 of 0.2% SDS was added to lyse the cells and cell lysates were pipetted into counting tubes. Emission was measured in individual tubes containing media, washing steps, or lysate in a Packard B5003 gamma counter (Packard BioScience Benelux, Groningen, the Netherlands) between 450 and 800 keV for 2 minutes. For efflux studies, after copper treatment for 24 h, cells were washed four times with Hanks prior to incubation in fresh warm media containing no additional copper for 2 h. Cells were then analysed for copper as described above. Copper accumulation was normalized to the protein concentration of the cell lysate (quantified using a Bio Rad Protein Assay Kit, Bio Rad) and an MTS colorimetric assay (3-[4,5-dimethylthiazol-2-yl]-5-[3-carboxymethoxyphenyl]-2-[4-sulfophenyl]-2H-tetrazolium) (Promega) was run in parallel. This quantitative assay detects living but not dead cells. The absorbance at 490 nm (test wavelength) and at 650 nm (reference wavelength) was measured using an enzyme-linked immunosorbent assay microplate reader (Bio-Rad); wells containing culture medium but no cells served as blanks. In this experiment, 104 cells in 100 µL of culture medium were seeded into each well of a 96-well plate. After achieving 70% confluence, the cells were treated with 10, 50 or 100 µM copper. After incubation for 24 and 48 h, the wells were washed, and 100 µL of culture medium and 20 µL of MTS were added to each well. After a 2 hr incubation at 37° C., the absorbance at 490 nm was measured.

RNA Isolation

Total RNA was isolated from tissue fibroblasts in triplicate using phenol chloroform extraction prior to clean-up using Qiagen RNeasy Tissue Kit (Qiagen) according to the manufacturer's instructions. Briefly, approximately 75 mg of tissue was isolated and added to 1 ml of Tri Reagent and a 5 mm Qiagen steel ball bearing. The tissue was homogenized via a TissueLyser (Qiagen) for 3 times 2 min at 20 30 Hz. 100 µl of 1 bromo 3 chloropropane was added, vortexed briefly and allowed to stand for 5 min at room temperature prior to centrifugation for 15 min at 4° C. in a bench top centrifuge. The clear aqueous phase was removed and added to 0.5 ml of isopropanol, allowed to settle and respun for 10 min at 4° C. The pellet was washed in 70% ethanol, air dried at room temperature and resuspended in 300 µl of water. The RNA was further cleaned with gDNA eliminator columns and purified using Qiagen RNeasy plus kit. Total RNA was isolated from cells using Qiagen RNeasy plus kit.

In total 2 µg of RNA was reverse transcribed using High Capacity RNA to cDNA (ABI) Kit as per manufactures instructions in a 20 µl reaction volume. The cDNA derived from tissue was diluted 1 in 20 prior to examination via qPCR. cDNA derived from cells was diluted 1 in 100 for ATP7A analysis or 1 in 10 for MT1A analysis.

The RNA samples were treated with DNase I (Qiagen RNase free DNase kit). In total 3 µg of RNA was incubated with poly(dT) primers at 42° C. for 45 min, in a 60 µl reaction volume, using the Reverse Transcription System from Promega (Promega Benelux, Leiden, The Netherlands).

Real Time Quantitative PCR (qPCR)

Q-PCR was performed as described by Spee et al (J Vet Intern Med 2006: 20:1085-1092). Real-time PCR was based on the high affinity double-stranded DNA-binding dye SYBR green I and was performed in triplicate in a spectrofluorometric thermal cycler. For each PCR reaction, 8.7 µl (of the diluted stock) of cDNA was used in a reaction volume of 20 µl containing 1× Power SYBR® Green PCR Master Mix, 40 pmol of both primers, on 384 well plates. Primer pairs (except those for ATP7A), depicted in Table XI, were taken from Spee et al. All PCR protocols included a 5-minute polymerase activation step and continued with for 40 cycles (denaturation) at 95° C. for 20 sec, annealing for 30 sec, and elongation at 72° C. for 30 sec with a final extension for 5 min at 72° C. Annealing temperatures ranged from 50° C. till 67° C. (Table XI). Dissociation curves, Bioanalyser (Agilent 2100) and sequencing (MWG) were used to examine each sample for purity and specificity. Efficiency curves constructed by plotting the relative starting amount versus threshold cycles were generated using serial 10-fold dilutions of cDNA. The amplification efficiency, E (%)=(10(1/s)1)·100 (s=slope), of each standard curve was determined and appeared to be >95%, and <105%, over a wide dynamic range. Each experimental sample was normalised to the endogenous references hypoxanthine phosphoribosyl transferase (HPRT), RPL8, RPS5 and RPS19 with appropriate propagation of error.

Western Blotting

Cells were washed 3 times with PBS and lysed in 200 µl freshly made boiling lysis buffer (Tris-buffered saline (TBS) containing 1% SDS) using a rubber policeman to scrape off cells. Samples were homogenised by passing through a 25 gauge needle several times and then heated to 70° C. for 5 min before storing at −20° C. pending analysis. Cell lysates were thawed, boiled for 5 min in loading buffer (50 mM Tris.HCl, pH6.8, 2% SDS, 0.1% bromophenol blue, 10% glycerol, 40 mM DTT) and loaded onto preassembled SDS-PAGE. The membranes were blocked in 5% milk/PBS-T for 1-2 h before incubation for 1 h at RT with the primary antibody. The membranes were washed 3 times for 10 min with blocking buffer prior to 1 h incubation at room temperature with rabbit anti-chicken Ig HRP antibody at a dilution of 1:10,000 in blocking buffer. Membranes were washed 3 times with blocking buffer for 10 min followed by 1 wash with PBS-T. Membranes were briefly washed in PBS to remove detergent and were developed using the ECL western blotting detection reagents system according to the manufacturer's instructions. Membranes were subsequently exposed to SuperRX Fuji X-ray film (Tokyo, Japan) and developed in a Kodak automated processor (Eastman Kodak Company, Japan).

In order to show equal protein loading, membranes were stripped and re-probed. The membrane was Western blotted with mouse anti-tubulin (10,000 dilution, 5% BSA/TBS-T/T, for 1 h at RT, followed by goat anti-mouse HRP (1:10,000) 1% BSA/PBS-T/T, 1 h at RT) and visualised with ECL Western blotting detection reagents as previously described.

Stripping Membranes

Membranes were stripped of bound antibody prior to re-probing. Membranes were incubated at 55° C. for 30 min in stripping buffer (100 mM 2-mercaptoethanol, 2% SDS, 62.5 mM Tris-HCl, pH 6.7) and then washed extensively in PBS before further Western blotting.

Statistics qPCR data was log 10 transformed prior to analyses, to ensure homogeneity of variance (an assumption of parametric analyses). The log 10(expression) values were then analysed by ANOVA, weighted for the standard error of the expression values. Pairwise comparisons were made to the ATP7A$^{C/C}$ genotype and fold changes with 95% confidence intervals were calculated.

TABLE XI

Nucleotide Sequences of Dog-Specific Primers for Quantitative Real-Time PCR

| Gene | Primer | Sequence (5'-3') | Tm (° C.) | Accession number | SEQ ID NO: |
|---|---|---|---|---|---|
| Hypoxanthine phosphoribosyl-transferase (HPRT) | Forward | AGCTTGCTGGTGAAAAG GAC | 56 | L77488 / L77489 | 144 |
| | Reversed | TTATAGTCAAGGGCATA TCC | | | 145 |

TABLE XI-continued

Nucleotide Sequences of Dog-Specific Primers for Quantitative Real-Time PCR

| Gene | Primer | Sequence (5'-3') | Tm (° C.) | Accession number | SEQ ID NO: |
|---|---|---|---|---|---|
| Metallothionein (MT1A) | Forward | AGCTGCTGTGCCTGATG TG | 61 | D84397 | 146 |
|  | Reversed | TATACAAACGGGAATGT AGAAAAC |  |  | 147 |
| Ribosomal protein S5 (RPS5) | Forward | TCACTGGTGAGAACCCC CT | 62.5 | XM_533568 | 148 |
|  | Reversed | CCTGATTCACACGGCGT AG |  |  | 149 |
| Ribosomal protein S19 (RPS19) | Forward | CCTTCCTCAAAAA/GTC TGGG | 61 | XM_533657 | 150 |
| S19 (RPS19) | Reversed | GTTCTCATCGTAGGGAG CAAG |  |  | 151 |
| Ribosomal protein L8 (RPL8) | Forward | CCATGAATCCTGTGGAG C | 55 | XM_532360 | 152 |
|  | Reversed | GTAGAGGGTTTGCCGAT G |  |  | 153 |
| ATPase, Cu++ transporting, alpha polypeptide (ATP7Ai) | Forward | CTACACTCCAATATGTA AGCAGC | 60 | AY603040 | 154 |
|  | Reversed | AGGTACTCTCAACTTCA CTAGC |  |  | 155 |
| ATPase, Cu++ transporting, alpha polypeptide (ATP7Aii) | Forward | AAACATCAAAGGCTCCT ATCC | 57 | AY603040 | 156 |
|  | Reversed | GGAAAGCAAAGCGTATT ATCG |  |  | 157 |
| ATPase, Cu++ transporting, alpha polypeptide (ATP7Aiii) | Forward | AGTATGAGTGTGGATTC GGT | 60 | AY603040 | 158 |
|  | Reversed | TTTGGAGTCTGTAGTTT AGGGT |  |  | 159 |

Results

Canine Dermal Mutant Fibroblasts Incorporate More Copper 64 and Efflux at a Slower Rate than Wildtype or Heterozygote Cells.

Henceforth wildtype, heterozygote and mutant cells are referred to as ATP7A$^{C/C}$, ATP7A$^{C/T}$ or ATP7A$^{T/T}$ respectively. Incubation of fibroblasts with supraphysiological concentrations of the isotope copper-64 (Cu64) (100 μM) shows an approximately two-fold increase in incorporation of copper after 24 h and 48 h in ATP7A$^{T/T}$ cells and ATP7A$^{C/T}$ cells compared to ATP7AC$^{/C}$ cells (FIG. 7A). At a lower concentration (50 μM) ATP7A$^{T/T}$ cells incorporated a higher amount of copper compared to the other genotype cells. Incubation at physiological concentrations shows no difference in incorporation between the cell types. To determine whether the increase in Cu64 levels in the ATP7A$^{T/T}$ cells was due to abrogated efflux, we next measured the level of efflux from the cells via a washout method (FIG. 7B) After the addition of high amounts of Cu64 (100 μM) and 2 h of washout, the ATP7A$^{C/C}$ cells had retained approximately 45% of the isotope, whereas the ATP7A$^{T/T}$ cells had retained almost 90%. The ATP7A$^{C/T}$ cells which had incorporated a similar amount of copper as the ATP7A$^{T/T}$ cells showed similar rate of efflux as the ATP7A$^{C/C}$ cells. Concomitant to the higher amounts of copper incorporation, cell viability was found to be lower in the ATP7A$^{T/T}$ cells under high copper loading (data not shown)

As a control the experiment was performed in parallel using human wildtype cells and cells derived from a Menkes patient. As expected Menkes cells showed higher incorporation at all Cu64 concentrations used (FIG. 7C), and effluxed Cu64 at a reduced rate compared to wildtype cells (FIG. 7D). Interestingly, incorporation of Cu64 at 24 and 48 h was higher in both wildtype and Menkes cells compared to the canine cells. It remains to be seen what the steady state levels of copper under basal conditions are in human and canine cells.

ATP7A Gene Expression is Unaltered in ATP7A$^{T/T}$ Cells

To establish whether the reduction in efflux was due to the expression levels of ATP7A, we analyzed ATP7A transcript levels using qPCR. ATP7A isoforms have not been described for dog, so 3 primer sets were designed as follows: ATP7Ai amplified a region overlapping the mutation, and ATP7Aiii and ATP7Aii were designed to amplify regions in the 3' and 5' ends of the transcript, in order to account for splice variants. Under basal conditions or incubation with copper no change was found in ATP7A expression levels between the genotypes (FIG. 8A). However when ATP7A protein levels were measured, ATP7A expression was found to be copper-dependent in all 3 of the canine cell lines, with the highest expression in the ATP7A$^{T/T}$ cells (FIG. 8B), which was not reversible with the addition of the copper chelator BCS in the timepoint measured. Interestingly, under basal conditions there was higher ATP7A expression in ATP7A$^{T/T}$ cells compared to ATP7A$^{C/C}$ cells. A number of bands were present on the membrane, presumably corresponding to different isoforms. These bands however did not change and are not shown for simplicity. Further work using siRNA and overexpression constructs will be used to identify ATP7A specific bands.

ATP7A$^{T/T}$ Cells have Increased MT1A Gene Expression.

To determine whether the higher levels of copper incorporation in ATP7A$^{T/T}$ cells leads to higher expression of copper responsive genes, we performed qPCR analysis on metallothionein 1A (MT1A) expression in $ATP7A^{C/C}$, $ATP7A^{C/T}$ and $ATP7A^{T/T}$ cells (FIG. 9). Analysis of MT1A expression in untreated cells shows both $ATP7A^{C/T}$ and $ATP7A^{T/T}$ cells have significantly higher expression of MT1A compared to $ATP7A^{C/C}$ cells (FIG. 9A). $ATP7A^{C/T}$ and $ATP7A^{T/T}$ have significantly unregulated MT1A expression in response to 1-100 µM copper, whereas $ATP7A^{C/C}$ was significant above 10 µM copper addition (FIG. 9B). Additionally comparison of upregulation of MT1A expression in response to copper within the genotypes was not significant when compared between the genotypes except for $ATP7A^{T/T}$ in response to 1 µM copper $ATP7A^{C/C}_{UT\ vs\ Cu1}$ vs $ATP7A^{T/T}_{UT\ vs\ Cu1}$; (p=0.014). Thus $ATP7A^{T/T}$ cells are more sensitive to copper (FIG. 9C).

Copper Dependent Metallothionein Gene Expression is Higher in $ATP7A^{T/T}$ Cells Compared to $ATP7A^{C/C}$ The increased retention of copper and corresponding increased copper dependent MT1A expression in $ATP7A^{T/T}$ fibroblasts, led us to investigate whether the corresponding Menkes phenotype would be observed in intestine and liver biopsies. Thus, qPCR analysis was performed on MT1A expression on frozen samples of liver and small intestine tissue biopsied from the 3 individuals the fibroblasts were explanted from (FIG. 10). The expression of MT1A was significantly lower in $ATP7A^{T/T}$ liver tissue, and significantly higher in small intestine tissue, compared to $ATP7A^{C/C}$.

Canine Dermal $ATP7A^{T/T}$ Fibroblasts have Reduced ATP7A Trafficking

To determine whether the increase in copper in the $ATP7A^{T/T}$ cells was due to reduction in ATP7A trafficking we used immunocytochemistry to localize ATP7A in response to copper in the different cells types. We used BCS to chelate extracellular copper to 'stage' ATP7A in the TGN (top panel). As expected, ATP7A in both $ATP7A^{C/C}$ and $ATP7A^{T/T}$ cells was found predominately in the TGN (marked by anti-58K, middle panel). Following washout, and subsequent incubation with 100 µM copper for 1 to 3 hrs, ATP7A in $ATP7A^{C/C}$ cells translocated from the TGN to the cell periphery in order to export copper from the cell. The $ATP7A^{T/T}$ cells showed a marked abrogation of ATP7A translocation, as ATP7A was found predominantly in TGN after exposure to copper. The cell density shown in the panels are not indicative of growth rates. Both cell types were found to grow with a similar morphology and density.

Conclusion

The studies have indicated that the rate of accumulation of copper is greater in cells expressing the mutated form of the protein; accumulation is greater during copper exposure and release is slower after copper exposure. In addition, intracellular ATP7A movement in response to copper exposure is altered in cells carrying the mutation. There is also increased expression of a copper transport protein in cells carrying the mutation. Expression levels of ATP7A are not altered between cells carrying the two forms.

The results from this study suggest that there are significant differences in the transport and handling of copper between cells carrying the normal and the mutated forms of ATP7A. These differences, could start to explain the mechanism underlying the apparent differential susceptibility of Labradors to copper accumulation as a factor in CACH.

Example 6

Summary

The aim of the study was to investigate whether dietary management is effective to influence hepatic copper concentrations in Labradors after treatment with penicillamine, and whether additional treatment with zinc is useful.

The study was conducted on a group of 24 dogs consisting of 12 female and 12 male pure-bred Labradors. The dogs were family members of former patients with copper-associated chronic hepatitis. At the start of the diet trial dogs were clinically healthy but hepatic copper concentrations of 20 dogs were above the reference range of 400 mg/kg dry weight (mean: 894, range: 70-2810 mg/kg dry weight). These concentrations were measured after completion of treatment with penicillamine.

All dogs were fed the same diet. Additional treatment consisted of zinc gluconate (7.5 mg/kg PO BID, group 1) or a placebo (group 2). The pharmacist was the only person aware of group allocations until completion of the study. Hepatic copper concentrations and histopathology were assessed along with clinical examinations and blood-work before and after treatment for a mean of 8 months (range 5-13), and 16 months (range 12-25). Plasma zinc concentrations were measured at additional time points during treatment.

Twenty-one Labrador dogs completed the study. At the start of the study the mean age of dogs in group 1 was 4.1 years (range 2.7-8.3). Six dogs were females (5 spayed, 1 intact), and six were male (2 neutered, 4 intact). The mean age of dogs in group 2 was 4.8 years (range 3.6-11.2). Six dogs were female (4 spayed, 2 intact), and 6 dogs were male (2 neutered, 4 intact). Vomiting, anorexia, and diarrhea were observed as adverse effects in 3 dogs of the zinc gluconate supplemented group.

There was a significant difference of hepatic copper concentrations in both groups with dietary management over time (8 months: group 1 p<0.001, group 2 p=0.001, and 16 months: group 1 p=0.03, group 2 p=0.04). However, there was no difference in hepatic copper concentrations between groups, prior to treatment (p=0.65), at recheck-1 (p=0.52), and at recheck-2 (p=0.79), suggesting that there is no benefit of further zinc supplementation on hepatic copper accumulation.

The results of this study show that dietary management can be effective to decrease hepatic copper concentrations in Labradors. Adjunctive treatment with zinc did not amplify the de-coppering effect.

The study will now be described in more detail.

Materials and Methods

Labrador Retrievers

The study population consisted of 24 pure-bred Labrador Retrievers that were family members of dogs previously described with CACH. All dogs were registered at the Dutch Labrador Retriever breed club.

All dogs had completed their treatment with penicillamine prior to the start of this study. A medical history was obtained from all dogs and a physical examination was performed. Na-citrated blood samples were taken for analysis of a coagulation profile, including prothrombin time (PT), activated partial thromboplastin time (aPTT) and fibrinogen. Heparin- and EDTA-blood was sampled for analysis of the hepatobiliary enzymes alkaline phosphatase (ALP), alanine aminotransferase (ALT), of bile acids (BA), and for measurement of the platelet count, and plasma zinc concentrations. Liver biopsies were taken according to the Menghini technique given by Rothuizen (Rothuizen J, I. T. (1998) Tijdschr Diergeneeskd 123: 246-252). At least three liver biopsies were taken from each dog. Two biopsies were fixed in 10 percent neutral buffered formalin, and one biopsy was stored in a copper-free container for quantitative copper determination.

All biopsies were histologically assessed. Hepatic tissue was stained with rubeanic acid stain for evaluation of copper distribution and semiquantitation as previously described (Van den Ingh T. S. G. A. M., R. J., Cupery R. (1988) Vet Q 10: 84-89). According to the applied grading system copper scores above 2 are abnormal (0: no copper, 1: solitary liver cells and/or reticulohistiocytic (RHS) cells containing some copper positive granules, 2: small groups of liver cells and/or RHS cells containing small to moderate amounts of copper positive granules, 3: larger groups or areas of liver cells and/or RHS cells containing moderate amounts of copper positive granules, 4: large areas of liver cells and/or RHS cells with many copper positive granules, 5: diffuse presence of liver cells and/or RHS cells with many copper positive granules).

A quantitative assay for copper in liver tissue was performed by neutron activation analysis, according to a protocol described by Teske et al, using the facilities described by Bode (Bode, P. (1990) Journal of Trace and Microprobe Techniques 8: 139; Teske et al. (1992) Vet Rec 131: 30-32). Quantitative copper concentrations were measured in lyophilised liver biopsies and reported in mg/kg dry weight liver.

Apart from the copper content, further histological changes were graded on a scale between 0 and 5 in order to allow statistical testing (0=no histologic signs of inflammation, 1=reactive hepatitis, 2=mild chronic hepatitis, 3=moderate chronic hepatitis, 4=severe chronic hepatitis, 5=cirrhosis).

The study was approved by the Utrecht University Institutional Animal Care and Use Committee. Informed owner consent was obtained for all dogs.

Progression of Hepatic Copper Accumulation without Treatment

In eleven dogs measurement of hepatic copper concentrations was repeated after a mean of 8.7 months (range 6-15 months), prior to any treatment. During this time all animals were fed their usual maintenance diet, which contained dietary copper concentrations between 12-25 mg/kg dry matter and zinc concentrations between 80-270 mg/kg dry matter according to the manufacturers.

Diet

All dog owners were provided with the same specially manufactured diet. Approximate analysis of the diet as fed: moisture 57.9%, crude protein 6.1%, crude fat 5.9%, minerals 1.7%. Metabolizable energy (measured according to Association of American Feed Control Officials protocol): 1650 kcal/kg as fed). The diet contained copper at a concentration of 4.75 mg/kg dry matter, and zinc at a concentration of 102 mg/kg dry matter. The dogs were fed the diet without further dietary supplements and treats. The Labradors of this study received between 420 and 840 g diet/day.

Pharmacokinetic Study

Two unrelated nine-year old, healthy Labrador Retrievers (1 female and 1 male) were used in a pharmacokinetic study. Food was withheld for a 12-hour period prior to oral administration of zinc, and during the initial 6-hour testing period. Water was freely available. Oral zinc gluconate was administered at a dose of 10 mg/kg in dog 1, and at a dose of 5 mg/kg in dog 2. Heparinized blood samples (4 ml) were collected from the jugular vein before dosing (time 0) and 15, 30, 45, 60, 90, 120 minutes, and 4, 8, 12 and 24 hours after application of the drug. Plasma was stored at −20° C. until analysis for zinc using atomic absorption spectrometry.

Drug Preparation, Randomization, and Blinding

The choice for zinc-gluconate was made based on our clinical observation that the drug has fewer side effects than the other salts, like acetate or sulphate. The tablets were provided by the Veterinary Pharmacy of the Faculty of Veterinary Medicine, University of Utrecht. Zinc tablets contained 25 mg elemental zinc as zinc-gluconate salt (Toppharm Zink 25 gluconaat, Parmalux BV, Uitgeest, NL). Placebo tablets contained 160 mg lactose (Albochin, Pharmachemie BV, Haarlem, NL). Tablets from both groups had an identical appearance.

The Pharmacist randomized group allocations prospectively for sets of six dogs by flipping a coin. Three dogs received the placebo, and three dogs were treated with zinc. On prescription of the clinician, tablets (placebo or zinc) were dispensed according to a randomisation table.

Dosage of the prescription was according to the following scheme:

| Bodyweight: | | |
|---|---|---|
| <28 kg (<61.6 lbs): | 8 tablets BID | (200 mg BID) |
| 28-35 kg (61.6-77 lbs): | 9 tablets BID | (225 mg BID) |
| above 35 (>77 lbs): | 10 tablets BID | (250 mg BID) |

Owners were instructed to give the tablets mixed with small amounts of their diet 30 minutes before feeding. Neither the owner nor the clinician was informed about which treatment each dog received. The randomization table remained in possession of the Pharmacy during the trial and was only revealed upon completion of the trial.

Statistical Analysis

Pharmacokinetic parameters (WinNonlin 4.0.1. (Pharsight Corporation, 800 West El Camino Real, Mountain View, Calif., USA) and statistical analysis (SPSS 11.0 for windows, 2001, SPSS Inc., Chicago, Ill., USA) were calculated by use of commercially available software packages. Due to small group sizes a non-parametric statistical test was used for comparison between groups. A Mann-Whitney test was used to detect a difference between hepatic copper concentrations before and after treatment with diet and zinc-gluconate (group-1) at two control examinations (recheck-1 and recheck-2), and after treatment with diet and placebo (group-2) at both control examinations. In addition the test was used to detect a difference between group-1 and group-2 before the study, at recheck-1, and at recheck-2 (significance level $p<0.05$).

Results

Progression of Hepatic Copper Accumulation without Treatment

Figure 1:
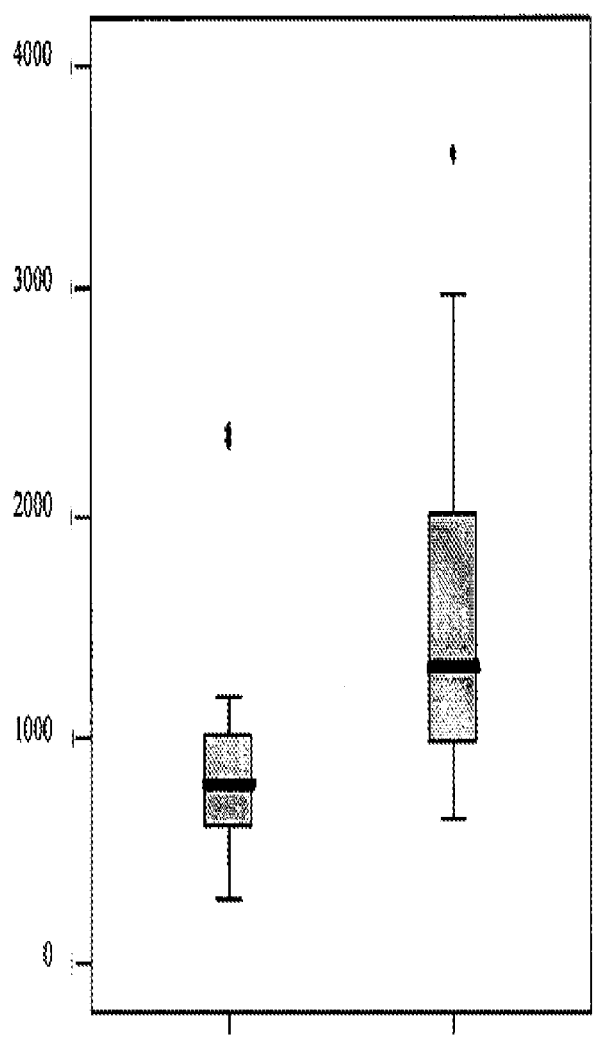
FIG. 1 illustrates the progression of hepatic copper accumulation without treatment. The Figure shows hepatic copper concentrations (mg/kg dry weight) of 11 Labrador Retrievers at two examinations 8.7 months (range 6-15 months) apart, prior to any treatment. During this time all animals were fed their usual maintenance diet, which according to the manufacturers contained dietary copper concentrations between 12-25 mg/kg on a dry matter basis and zinc concentrations between 80-270 mg/kg on a dry matter basis. The diamond symbols represent outliers.

In eleven Labrador dogs measurement of hepatic copper concentrations was repeated before any treatment was given, and while the dogs were fed their usual maintenance diet. In all but one dog hepatic copper concentrations increased during the time interval of 8.7 months between both measurements from a mean of 1000 mg/kg dry weight (range 290-2370) to a mean of 1626 mg/kg dry weight (range 630-3610). Related to the bodyweight of the patients (mean: 33.9 kg, range 25-39.5 kg) this was an increase of 18 mg copper per kg bodyweight during 8.7 months. The results are shown in FIG. 1.

Pharmacokinetic Study

Pharmacokinetic parameters calculated from plasma zinc concentrations measured in two dogs after oral application of 10 mg/kg (dog 1) and 5 mg/kg (dog 2) elemental zinc were:
Dog 1 (10 mg/kg): V_F: volume of distribution=2937.872 ml/kg bodyweight, K01: absorption rate constant=0.567212 1/hour, K10: elimination rate constant=0.053728 1/hour, AUC: area under the curve=63.35272 hr*μg/ml, Cl_F: clearance in relation to the bioavailability=157.8464 ml/hr/kg, Tmax: time of maximum concentration=4.589813 hours, Cmax: maximal clearance=2.659924 μg/ml)

Dog 2 (5 mg/kg): V_F: volume of distribution=2538.689 ml/kg bodyweight, K01: absorption rate constant=1.160647 1/hour, K10: elimination rate constant=0.037886 1/hour, AUC: area under the curve=51.98513 hr*µg/ml, Cl_F: clearance in relation to the bioavailability=96.18135 ml/hr/kg, Tmax: time of maximum concentration=3.047974 hours, Cmax: maximal clearance=1.754728 µg/ml).

The calculated half-life of zinc was t½=15.1 hours.

The calculated accumulation rate R was 1.52, from R=1/(1-exp(−k10*24). The dose interval was chosen to be 12 hours. A dose estimate was 127.0139 ml/hr/kg, calculated from the mean of CL_F from both dogs.

An estimate of the appropriate dosage was based on an intended maximum zinc plasma concentration of 5 µg/ml. Dosage=Cl_F×intended blood concentration×dose interval=7.62 mg/kg q 12 hours Diet Trial and Randomized, Placebo-Controlled Zinc Application At the start of the diet trial hepatic copper concentrations of 20 dogs were above the reference range of 400 mg/kg dry weight (mean: 894, range: 70-2810 mg/kg dry weight). Results from semiquantitative assessment of copper ranged from 0 to 4.5. Histopathological examination of liver biopsies from 17 dogs revealed an elevated hepatic copper content (above 2), which was localized to centrolobular hepatocytes. Staining for copper was normal in 5 dogs, and high normal staining results were obtained from biopsies of 2 dogs with elevated hepatic copper from quantitative analysis. In seven dogs chronic hepatitis was present. CH was characterized by varying degree of hepatocellular apoptosis and necrosis, mononuclear inflammation, regeneration and fibrosis. The activity of the hepatic inflammation was determined by the quantity of inflammation and extent of hepatocellular apoptosis and necrosis. The stage of the disease was determined by the extent and pattern of fibrosis and the presence of cirrhosis Hepatitis was mild in 4 patients, moderate in 2 dogs, and cirrhosis was diagnosed in 1 dog. In thirteen dogs there were no histological signs of inflammation present in the liver, and in biopsies of 4 dogs histopathology revealed reactive changes.

At the start of the study the mean age of dogs in group 1 was 4.1 years (range 2.7-8.3). Six dogs were-spayed females, and six were male (2 neutered, 4 intact). The average bodyweight was 33 kg (range 26.2-37.5). The mean hepatic copper concentration of the dogs in group 1 was 961 mg/kg dry weight (range 340-2810). The mean semiquantitative assessment of copper from histological staining was 2-3+ (range 0-4.5).

The mean age of dogs in group 2 was 4.8 years (range 3.6-11.2). Six dogs were female (4 spayed, 2 intact), and 6 dogs were male (2 neutered, 4 intact). The average bodyweight was 32.3 kg (range 25-41.9). The mean hepatic copper concentration of dogs in group 2 was 861 mg/kg dry weight (range 70-1680). There was no difference in hepatic copper concentrations between both groups prior to treatment (p=0.73). The mean semiquantitative assessment of copper from histological staining was 2-3+ (range 0.5-3).

Three dogs of group-1 did not complete the study. The reason for discontinuation was unrelated to the treatment in all three dogs (one owner felt his dog was getting too old, one owner had personal reasons, and one dog developed a mast cell tumor). Twenty-one dogs completed the study, with at least one control examination (recheck-1). In sixteen dogs liver biopsies were obtained at an additional later time point (recheck-2).

Vomiting, and anorexia were observed adverse effects in 3 dogs of group 1. One of these dogs also had transient small bowel diarrhea. The adverse effects occurred immediately after application of the tablets, and resolved when the tablets were mixed with the diet.

Blood Examinations

The concentration of bile acids decreased from a mean of 14 µmol/l (range: 3-101), to a mean of 7.8 (range: 1-39) at recheck-1 and 7.1 (range: 0-21) at recheck-2. The mean concentration of alkaline phosphatase (ALP), and alanine aminotransferase (ALT) remained within the normal range at all examinations. The mean ALP concentration before treatment was 41 U/l (range: 8-111), at recheck-1: mean ALP=37 U/l (range 12-143), at recheck-2: mean ALP=37 U/l (range: 19-152). The mean ALT concentration before treatment was 28 U/l (range: 10-234), at recheck-1: mean ALT=47 U/l (range: 11-78), at recheck-2: mean ALT=51 U/l (26-68).

At the beginning of the study the mean plasma concentrations of zinc were 95 µg/dl and 96 µg/dl in group-1 and group-2 respectively. There was no difference in plasma zinc concentrations of either group at recheck-1 and recheck-2 (p values between 0.11 and 0.79). No difference in plasma zinc concentration was found between group 1 and group 2 at any of the three examinations (p values between 0.34 and 0.5). The only time-point at which a difference in plasma zinc concentrations could be found was a blood examination after the initial month of treatment with zinc in group 1. Blood sampling was performed 2-6 hours after zinc application. At this control examination the mean plasma zinc concentration had increased to 165 µg/dl (range 117-249, p=0.02).

Hepatic Copper Measurements

Figure 2:
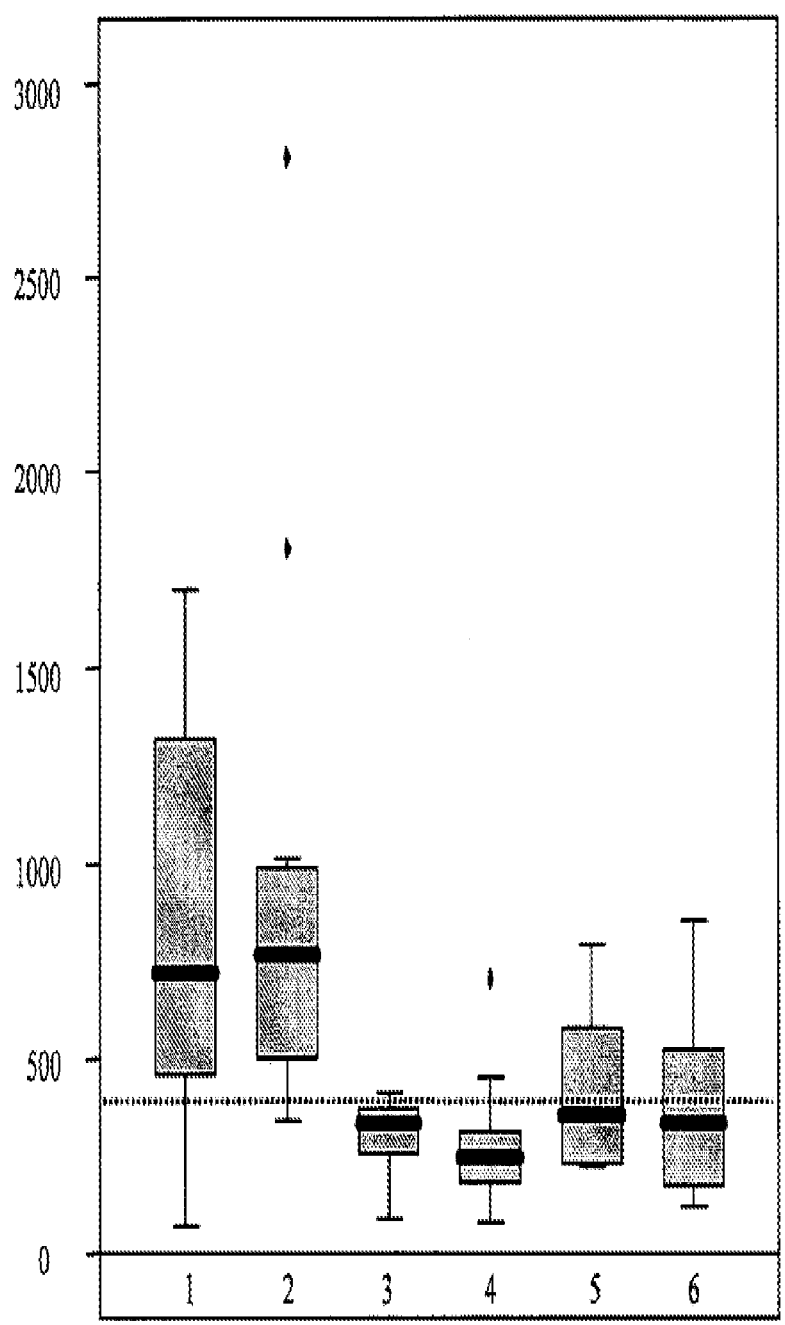
FIG. 2 illustrates hepatic copper concentrations (mg/kg dry weight) of 24 Labrador Retrievers at the beginning of the study and at 2 control examinations during dietary management. The dogs were divided into two groups as follows: group 1=diet+zinc gluconate tablets, group 2=diet+placebo. The key to the x-axis numbering is as follows: 1+2=before treatment, 3+4=recheck 1 (first control examination after 8 months (range 5-13 months)), 5+6=recheck 2 (second control examination after 16 months (range 12-25 months)). The numbers of dogs tested are as follows: 1: N=12 dogs in group 1, 2: N=12 dogs in group 2, 3: N=9 dogs in group 1, 4: N=12 dogs in group 2, 5: N=6 dogs in group 1, 6: N=10 dogs in group 2. The diamond symbols represent outliers. The dotted line represents the normal level of hepatic copper for adult dogs.

Quantitative measurement of hepatic copper improved during treatment in both groups. At recheck-1, and at recheck-2, hepatic copper concentrations had decreased significantly in both groups of dogs, compared to the starting point (group-1 at recheck-1: mean 286 mg/kg, range 84-700, p<0.001; group-1 at recheck-2: mean 421 mg/kg, range 220-790, p=0.03, group-2 at recheck-1: mean 277 mg/kg, range 80-450, p=0.001, group-2 at recheck-2: mean 401 mg/kg, range 118-850, p=0.04). There was no difference in hepatic copper concentrations between both groups at recheck-1 (p=0.52), and there was no difference between groups at recheck-2 (p=0.79). In addition there was no further decrease of hepatic copper concentrations between recheck-1, and recheck-2 (group-1 p=0.44, group-2 p=0.25). The results are shown in FIG. 2.

Histology

Histological staining for copper improved with treatment. Histological scores for semi-quantitative assessment of copper decreased in group 1 and group 2 at recheck-1 and recheck-2 compared to the starting point (group 1 at recheck-1: p=0.031, group 1 at recheck-2: p=0.01, group 2 at recheck-1: p=0.01, group 2 at recheck-2: p=0.001). There was no difference between both groups at any time-point (p=0.16-0.75).

Histological scoring for severity of inflammation of the liver remained unchanged throughout all examinations of the dogs from both groups (p=0.25-0.45).

Conclusion

In order to provide patients with CACH with a more balanced long term control of hepatic copper concentrations the aim of this study was to investigate whether dietary management is effective to influence hepatic copper concentrations in Labradors after treatment with penicillamine, and whether additional treatment with zinc is useful. The results of this study show that dietary management can be effective to decrease hepatic copper concentrations. Adjunctive treatment with zinc did not amplify the de-coppering effect.

Example 7

Figure 3:
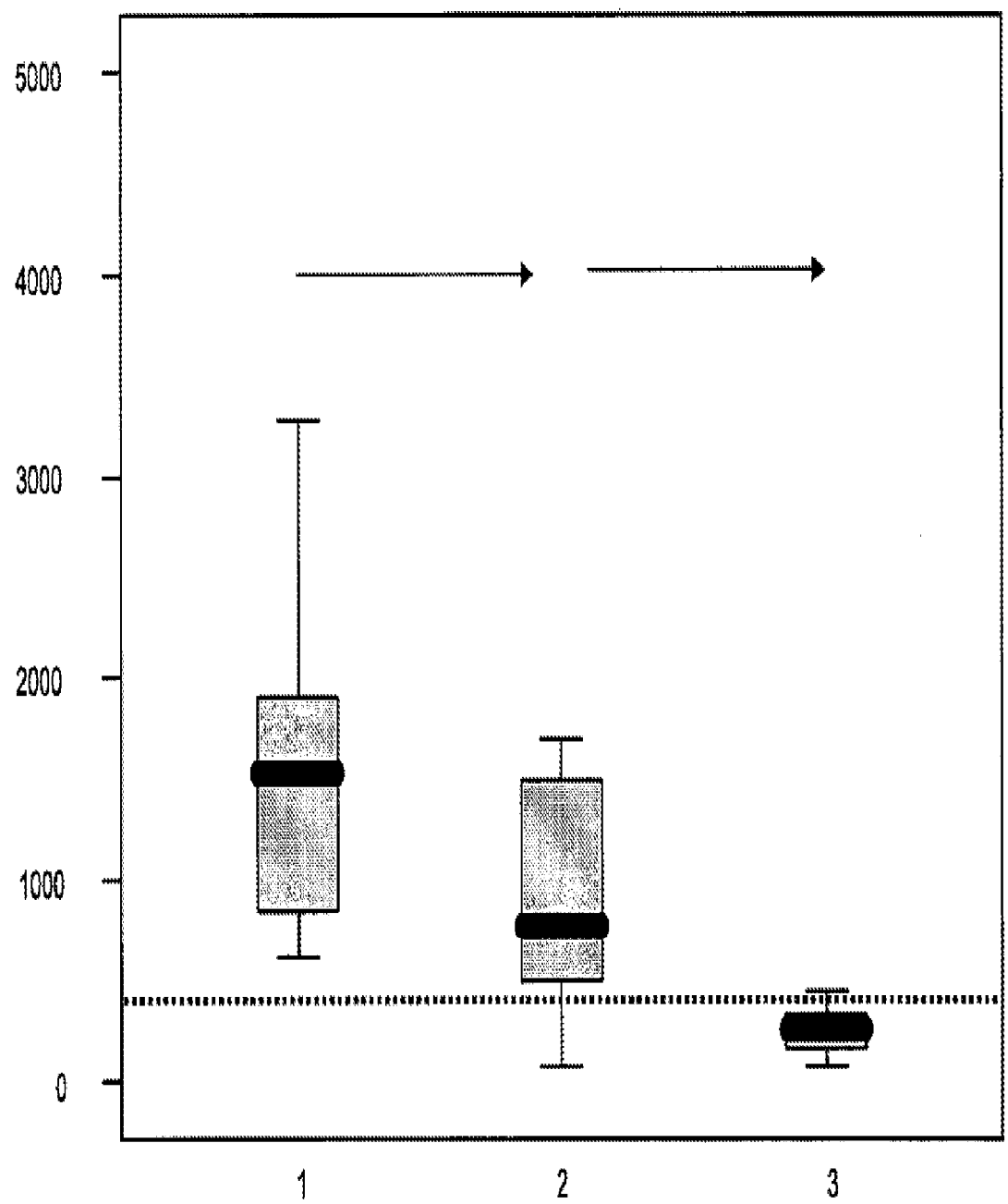
FIG. 3 illustrates the effectiveness of the diet of the invention on hepatic copper concentrations (mg/kg dry weight) in 18 Labrador Retrievers compared with the effect of penicillamine alone. The key to the x-axis is as follows: 1=pre-penicillamine, 2=post-penicillamine/pre-food, 3=post-food.

During an investigation of the effect of zinc on hepatic copper concentration, hepatic copper concentration was measured in 18 pure-bred Labrador Retrievers. Half of the dogs were provided with a supplement of zinc and the other half were provided with a placebo. All of the dogs were fed the diet of Example 6. Hepatic copper 25 concentration was measured using the method of Example 6 at 3 time points: (1) before treatment with penicillamine; (2) after treatment with penicillamine but before treatment with the diet of Example 6; and (3) after the diet treatment. As in Example 6, there was no significant difference between copper levels in dogs treated with zinc and with the placebo (data not shown). However, the use of the diet did have a significant effect on 30 the copper levels. The combined results for dogs treated with zinc and with the placebo are shown in FIG. 3 and demonstrate that the low copper diet has a more significant effect on reducing liver copper levels than penicillamine alone.

Example 8

An example of a foodstuff of the invention is set out below:

| Ingredient (%) | 100 |
|---|---|
| Water | 47.4 |
| Cereals | 28.5 |
| Vegetable by-products | 1.7 |
| Egg and egg by-products | 1.5 |
| Meat and animal by-products | 17 |
| Oil and fat | 2 |
| Minerals and vitamins | 1.9 |

A typical analysis of the amounts of minerals and trace elements in this foodstuff, together with the method used, is provided as follows:

| Analysis | Result (% weight as fed or mg/kg dry matter) | Notes |
|---|---|---|
| Moisture | 63% | Loss by drying at 105° C. for 5 hours |
| Protein | 6.5% | Protein by Kjeldahl using nitrogen factor 6.25 |
| Fat | 4.2% | Acid hydrolysis and petroleum ether extraction |
| Ash | 2.2% | 16 hr ramp temperature programme, final ash at 550° C. for 5 hr |
| Crude fibre | 1.4% | EC method OJ L344 26/11/92 P35, Directive 92/89 |
| Copper | 5.4 mg/kg | By flame atomic absorption spectrophotometry |
| Zinc | 229 mg/kg | By flame atomic absorption spectrophotometry |
| Iron | 62 mg/kg | By flame atomic absorption spectrophotometry |
| Calcium | 9 460 mg/kg | By flame atomic absorption spectrophotometry |
| Phosphorus | 5 405 mg/kg | By colorimetric reaction |

Example 9

A further example of a foodstuff of the invention is as follows:

| Ingredient (%) | 100 |
|---|---|
| Cereals | 39.7 |
| Vegetable by-products | 8.0 |
| Vegetable protein extract | 5.0 |
| Meat and animal by-products | 35.6 |
| Oil and fat | 7.5 |
| Minerals and vitamins | 4.2 |

A typical analysis of the amounts of minerals and trace elements in this foodstuff, together with the method used, is provided as follows:

| Analysis | Result (% weight as fed or mg/kg dry matter) | Notes |
|---|---|---|
| Moisture | 8.0% | Loss by drying at 105° C. for 5 hours |
| Protein | 30.0% | Protein by Dumas using nitrogen factor 6.25 |
| Fat | 13.0% | Acid hydrolysis and petroleum ether extraction |
| Ash | 6.3% | 16 hr ramp temperature programme, final ash at 550° C. for 5 hr |
| Crude fibre | 4.1% | EC method OJ L344 26/11/92 P35, Directive 92/89 |
| Copper | 10.9 mg/kg | By flame atomic absorption spectrophotometry |
| Zinc | 245 mg/kg | By flame atomic absorption spectrophotometry |
| Iron | 217 mg/kg | By flame atomic absorption spectrophotometry |
| Calcium | 1 087 mg/kg | By flame atomic absorption spectrophotometry |
| Phosphorus | 760 mg/kg | By colorimetric reaction |

The invention claimed is:

1. A method of preventing a disease attributable to liver copper accumulation in dogs having genetic inheritance of the Labrador Retriever breed, comprising feeding a foodstuff comprising copper at a concentration of between 4.5 and 10 mg/kg dry matter to a dog having genetic inheritance of the Labrador Retriever breed directly determined to have at least one cytosine at position 102 of SEQ ID NO: 142.

2. The method according to claim 1, wherein the foodstuff is provided to the dog one or more times per day.

3. The method according to claim 1, wherein said feeding is continued throughout the dog's life.

4. The method according to claim 1, further comprising providing the foodstuff to the dog's owner.

5. The method according to claim 1, wherein the dog is a dog having at least one parent that is a pure-bred Labrador Retriever.

6. The method according to claim 1, wherein the dog has no clinical symptoms associated with liver copper accumulation.

7. The method according to claim 1, wherein the dog has a liver copper concentration of less than 400 mg/kg of dry weight liver.

8. The method according to claim 1, wherein the dog does not have detectable liver disease.

9. The method according to claim 1, wherein the dog is at risk for having copper-associated chronic hepatitis.

10. The method according to claim 1, wherein the foodstuff further comprises zinc at a concentration of at least 120 mg/kg dry matter.

11. The method according to claim 1, further comprising feeding the dog a foodstuff or supplement comprising zinc at a concentration of at least 120 mg/kg.

* * * * *

SEQUENCE LISTING

```
<160> NUMBER OF SEQ ID NOS: 159

<210> SEQ ID NO 1
<211> LENGTH: 121
<212> TYPE: DNA
<213> ORGANISM: Canis familiaris
```

```
<400> SEQUENCE: 1
ctcagaacta gataggctaa taagtgatag gccttgtgtt ttcctagagt gtgctttaaa    60
rgtttcttaa gctaaaaaat tacattcgtg agaaaattga aataaaagga aaacagtcat   120
g                                                                   121

<210> SEQ ID NO 2
<211> LENGTH: 121
<212> TYPE: DNA
<213> ORGANISM: Canis familiaris

<400> SEQUENCE: 2
tctcagatac ttgatagcca gcatttcccc ccatttctct tccaagagcac gaaagcatag   60 raatgatatt acatctcgta tggtgaatgt gacacagccg tcagttgcgt tagctctgct   120
t                                                                   121

<210> SEQ ID NO 3
<211> LENGTH: 121
<212> TYPE: DNA
<213> ORGANISM: Canis familiaris

<400> SEQUENCE: 3
tattaccctg ctctccagcc actcctttac cttccattag cccacacctg ctctacacac    60
yattgctcat ggaagccttg ccacgtccag tcgccactct gaaatgccag catccctccc   120
a                                                                   121

<210> SEQ ID NO 4
<211> LENGTH: 121
<212> TYPE: DNA
<213> ORGANISM: Canis familiaris

<400> SEQUENCE: 4
gacctgacag attatgtaga ctttgttttc aaagggagca cctgctggat atacaacatg    60
rcactaaatt gtgctccaca tccttggcag aggtgggggg cggggcacaa aggaagaaac   120
c                                                                   121

<210> SEQ ID NO 5
<211> LENGTH: 121
<212> TYPE: DNA
<213> ORGANISM: Canis familiaris

<400> SEQUENCE: 5
gggcccagca agtggcagaa ctgggaagac ccctcttct tccgcctgga gcagtggtgt    60
rgcagcacac cacaggagtc tgaaagggtg gggagtccaa acgggaacat atacctgaga   120
t                                                                   121

<210> SEQ ID NO 6
<211> LENGTH: 121
<212> TYPE: DNA
<213> ORGANISM: Canis familiaris

<400> SEQUENCE: 6
ggcaacaggg acaggctgct gggccacaca ctcacccaca ctaggagaca agatcctcca    60
yatcctgggt ctctatcagt caatcaccta gaccagtggg ccagaggaca gggtccagct   120
g                                                                   121
```

```
<210> SEQ ID NO 7
<211> LENGTH: 121
<212> TYPE: DNA
<213> ORGANISM: Canis familiaris

<400> SEQUENCE: 7
gttgagagag atcatacaga ttcatgtggc aggtgcacac ttttcctacc tcttacaacg    60
yattctctct ggccattcct tctcctgggt cccaaagtcg agagcttag cgggagccta    120 g                                                                    121

<210> SEQ ID NO 8
<211> LENGTH: 121
<212> TYPE: DNA
<213> ORGANISM: Canis familiaris

<400> SEQUENCE: 8
ataagttcac attttggtgt ttcaagtgga catgaatgga ggggagggcc ctgttcaatc    60
yactaaagtg ttttttcatc ttgttttgt ggaaatcaaa tcaagaagca gagttttatg    120
t                                                                    121

<210> SEQ ID NO 9
<211> LENGTH: 121
<212> TYPE: DNA
<213> ORGANISM: Canis familiaris

<400> SEQUENCE: 9
actctcccga tgtgggcacc atatggtgga ccactttctg tgtgagatgc ctgctcttat    60
ygccatgtcc tgtgaagaca ccatgctggt ggaagcattt gcctttgccc tgggtgttgc    120
c                                                                    121

<210> SEQ ID NO 10
<211> LENGTH: 121
<212> TYPE: DNA
<213> ORGANISM: Canis familiaris

<400> SEQUENCE: 10
aatctaagta gactgagtgg tcaccttcag cgctcagacc tgagcataca aagcatggaa    60
rgttactgtg attcagctga tgtaatggaa tgaaataaat ataagagttt ggtaacctaa    120
t                                                                    121

<210> SEQ ID NO 11
<211> LENGTH: 121
<212> TYPE: DNA
<213> ORGANISM: Canis familiaris

<400> SEQUENCE: 11
tggagagtgc tggcaggcag gggcaggcaa acaacaatag caaagatctc ttccacgctt    60
ytacttcctc aaaagtccaa gccctcttaa gatcgcattt tcttagtgac cttcactcta    120
a                                                                    121

<210> SEQ ID NO 12
<211> LENGTH: 121
<212> TYPE: DNA
<213> ORGANISM: Canis familiaris

<400> SEQUENCE: 12
ttctttgcta ggccaagggc agagaatgca tgccccccct tacctcccag ggcccaagag    60
```

```
scatcctgag ctgagtctat ggctcctggt ggggggcggc tgtgggttgg ggggcacag      120 a                                                                    121

<210> SEQ ID NO 13
<211> LENGTH: 121
<212> TYPE: DNA
<213> ORGANISM: Canis familiaris

<400> SEQUENCE: 13
ggtgtcacca atgccagcga gcaccagctg gagggaacag gacacaggtc ctccgtcctg      60
ygacactcgg atctggggct tgcctccaa  aacggagacc atgcctgtcc atggttctac     120
g                                                                    121

<210> SEQ ID NO 14
<211> LENGTH: 121
<212> TYPE: DNA
<213> ORGANISM: Canis familiaris

<400> SEQUENCE: 14
ctctagaacc cttcaggtag actacattca ctttctacta caacttcatc accacaacca      60
wctcccagta acccccttttt tttcttctcc tttttttatt ttttccttct ttttgctcgt    120
c                                                                    121

<210> SEQ ID NO 15
<211> LENGTH: 121
<212> TYPE: DNA
<213> ORGANISM: Canis familiaris

<400> SEQUENCE: 15
tcccatgggt tgaaggatat ctggcagacg gctccaactc cagtaaagcc tcaggcctca      60
rccaggagtt ccccggggct tcattcccat cccagacttt gcccagggct gatttgaaag    120
t                                                                    121

<210> SEQ ID NO 16
<211> LENGTH: 121
<212> TYPE: DNA
<213> ORGANISM: Canis familiaris

<400> SEQUENCE: 16
tcttccttgc agattggatg gctgtagcct cacctcacac tgttgctggg atctgtccac      60
rcttctgacc tccagcaaga gcctccggga gctaagcctg ggcagcaatg acctgggaga    120
t                                                                    121

<210> SEQ ID NO 17
<211> LENGTH: 121
<212> TYPE: DNA
<213> ORGANISM: Canis familiaris

<400> SEQUENCE: 17
tattgctagt aaagccaaac tttctattcc acaattataa actcatggag atggtaatta      60
yagtgcatta tttgtcaaat tttattattt tttcaaatcc caaagaaaat gtgatattct    120
a                                                                    121

<210> SEQ ID NO 18
<211> LENGTH: 121
<212> TYPE: DNA
<213> ORGANISM: Canis familiaris
```

<400> SEQUENCE: 18
aagaacaagg atacaatcta agtgataatc atccagcatg tacttgtcct gttttcagat  60
katcagctta agtcaagagg aattttagt gcttacaaat atttcaagtg attttccag  120 a  121

<210> SEQ ID NO 19
<211> LENGTH: 121
<212> TYPE: DNA
<213> ORGANISM: Canis familiaris

<400> SEQUENCE: 19 tgaagggtg ctactcaggg ctcttcattt aaccttccag gatgttttcc tatgtactca  60
ytcttccttt tggttgctcc ttcttcttgc atttctttat ctctttacag aatcatccag  120
g  121

<210> SEQ ID NO 20
<211> LENGTH: 121
<212> TYPE: DNA
<213> ORGANISM: Canis familiaris

<400> SEQUENCE: 20
acaaccctaa aatttcagtg attcagtaca acaaaggttt attataacca ttcagggatc  60
saagttggta gaaacttcac tacaatacct gcttccagtc aacaagacag aaaaagaaaa  120
a  121

<210> SEQ ID NO 21
<211> LENGTH: 121
<212> TYPE: DNA
<213> ORGANISM: Canis familiaris

<400> SEQUENCE: 21
gcagggttga tatataacta gtatgcatta ggtagacacc tattttgatt actcactatt  60
ktaatatcag cctggtagta agaaccaaat ctattatgta aagtgcatag agaattgaaa  120
g  121

<210> SEQ ID NO 22
<211> LENGTH: 121
<212> TYPE: DNA
<213> ORGANISM: Canis familiaris

<400> SEQUENCE: 22
ctagctagcc acccaactcc ccacatgccc agagtcatcg tttatctttt cacatcagca  60
ytacattttg gcttgcattc aaacattagc ccatttttt cctttgtt ttatttatag  120 a  121

<210> SEQ ID NO 23
<211> LENGTH: 121
<212> TYPE: DNA
<213> ORGANISM: Canis familiaris

<400> SEQUENCE: 23
ttttctcttt ttccataaat gctctgggct tattttcatt atctagtatt tctcttctga  60
rgctaactcc caaagagttt tgtgcatcct tatttccatc acaaggtcaa tgtacgagtt  120
a  121

<210> SEQ ID NO 24
<211> LENGTH: 121
<212> TYPE: DNA
<213> ORGANISM: Canis familiaris

<400> SEQUENCE: 24
gggcccaagg gctgaggatc tctgtacctt ctgcttcttg gcagcccagg ctgggtagca    60
kttcttggaa gaggatttcc catgagttgt aacagaagg gcgggcttcc aggcgctgct   120
t                                                                   121

<210> SEQ ID NO 25
<211> LENGTH: 121
<212> TYPE: DNA
<213> ORGANISM: Canis familiaris

<400> SEQUENCE: 25
catctttgct tggggcctgg ggttttttatt gaggattgtg atctggtgta tgtgtctcct    60
yaggcatcca gaaaccattc agaacaagaa caagcgtcca ggtatcctct gtaagtcact   120
t                                                                   121

<210> SEQ ID NO 26
<211> LENGTH: 121
<212> TYPE: DNA
<213> ORGANISM: Canis familiaris

<400> SEQUENCE: 26
acaaaccctc agacccagat acacagtatc atgtggacac agacatgtaa caccaaaatg    60
mccaacatca tgtgactaca ggccctaagc aactaggtgt aacatcactt gggtatgggc   120
c                                                                   121

<210> SEQ ID NO 27
<211> LENGTH: 121
<212> TYPE: DNA
<213> ORGANISM: Canis familiaris

<400> SEQUENCE: 27
aatgcagtaa tacatgtagc taaacctaac catcagagtc tgttctatcc ttctacaaaa    60
rtagggttgg agctgagcac ataggtagca tacatctagc aaaagttttt gccttcagat   120
t                                                                   121

<210> SEQ ID NO 28
<211> LENGTH: 121
<212> TYPE: DNA
<213> ORGANISM: Canis familiaris

<400> SEQUENCE: 28
ttgtggggtc aggtgagtta tggacccctc cctactcttc tgctatcttg cccctacag    60 kggttgctat tttgatgtaa tcacaaaacg acctggcaat aaaacctttt tctaattagg   120
g                                                                   121

<210> SEQ ID NO 29
<211> LENGTH: 121
<212> TYPE: DNA
<213> ORGANISM: Canis familiaris

<400> SEQUENCE: 29
gatgcaagct gggacagaat aaggtactgg gctgtgtcaa gccccagtaa gagaggagca    60

```
ytgtagggta gttaggatgg acttaatgga gatgagtcct agggagccac actcagagtt    120
a                                                                    121

<210> SEQ ID NO 30
<211> LENGTH: 121
<212> TYPE: DNA
<213> ORGANISM: Canis familiaris

<400> SEQUENCE: 30 taaacaccc caatcactac catcctcaca cctaaggata cacaatgtgt ctactttatg     60
rtatgtcttt actattcgtt gcttatgaaa ttttattcat tawctaaaac agggaaaaaa   120
g                                                                    121

<210> SEQ ID NO 31
<211> LENGTH: 121
<212> TYPE: DNA
<213> ORGANISM: Canis familiaris

<400> SEQUENCE: 31
tatagytggs caattaaatc tcctattctt ttgtctcaaa ggatatttga aattacatag    60
ytcttttctc atataaaacc taccatacaa tcattagatg atccttctta gttaatttt   120 t                                                                    121

<210> SEQ ID NO 32
<211> LENGTH: 121
<212> TYPE: DNA
<213> ORGANISM: Canis familiaris

<400> SEQUENCE: 32
gatgctgtgg gccagtccag aacccacctg agagaaacaa acaggcctct ttgccagcag    60
rgcagcgtca gtgtcacccc tgtgacatgt cagaacctcc ctgaaagttc atctaacctc   120
t                                                                    121

<210> SEQ ID NO 33
<211> LENGTH: 121
<212> TYPE: DNA
<213> ORGANISM: Canis familiaris

<400> SEQUENCE: 33
ggctcagaag aaaaatcagc ccagttcaca tccaatgttt ccacacatct aatcgtcttg    60
rgttcagagg tagatgtggt atcacttaya tggacacata taacagctgg cccccacctc   120
t                                                                    121

<210> SEQ ID NO 34
<211> LENGTH: 121
<212> TYPE: DNA
<213> ORGANISM: Canis familiaris

<400> SEQUENCE: 34
gtttcagtta attatagtcc ttactggatc cgattgctgt ggcgctaaaa tgaaagaagg    60
yagggtacct gggtggctca ggggttgaga atctgctttt gactcaggtc atgatcccag   120
g                                                                    121

<210> SEQ ID NO 35
<211> LENGTH: 121
<212> TYPE: DNA
```

<213> ORGANISM: Canis familiaris

<400> SEQUENCE: 35

```
cagagtagca ttattttctg ctgtatgagg acacttttgt tatatccaca gtggacagaa    60
ractgggttt tagaacatgc tcaattgaaa caagactgag ggctcacaaa ttcctgctcc   120
a                                                                  121
```

<210> SEQ ID NO 36
<211> LENGTH: 121
<212> TYPE: DNA
<213> ORGANISM: Canis familiaris

<400> SEQUENCE: 36

```
ttacttattc atctgagacc aaggccactg tggtgaacct acaaagcctt acaaagcagg    60
rccagaaggg cacataaatc acttgactaa catttggtca aaatagctct gggctctttt   120
t                                                                  121
```

<210> SEQ ID NO 37
<211> LENGTH: 121
<212> TYPE: DNA
<213> ORGANISM: Canis familiaris

<400> SEQUENCE: 37

```
ataaaaataa aagagctatt aataagaact catmaaatct acataaatat agtaacaggt    60
yaatattccc agcatatttt tacaaatcat ctataaagag catgagagca tagggggatt   120
a                                                                  121
```

<210> SEQ ID NO 38
<211> LENGTH: 121
<212> TYPE: DNA
<213> ORGANISM: Canis familiaris

<400> SEQUENCE: 38

```
gcaacaacct ggtttgtgtg tgggaagcta atgcctcccc aaatgcagca aactctcctc    60
ytgattttag aaaagcagtt tagttacagg caaatgcata catgcatgat aaatactact   120
c                                                                  121
```

<210> SEQ ID NO 39
<211> LENGTH: 121
<212> TYPE: DNA
<213> ORGANISM: Canis familiaris

<400> SEQUENCE: 39

```
gattttataa aacatgatga ccttggcatt tatatagtag atattactac tctgaaattc    60
saggaagtat gatcataaac tcacacttaa tctggtagaa gtatggacaa tgtatcaaag   120
g                                                                  121
```

<210> SEQ ID NO 40
<211> LENGTH: 121
<212> TYPE: DNA
<213> ORGANISM: Canis familiaris

<400> SEQUENCE: 40

```
cttggttgag ttaaaacatt tgcccatgca atttaatgca tgtccctgtg gggttggaac    60
ygacgtacac ccgagccaac agcctttcat ggcagacgcc atcaggcagg tgaccccac    120
c                                                                  121
```

<210> SEQ ID NO 41
<211> LENGTH: 121
<212> TYPE: DNA
<213> ORGANISM: Canis familiaris

<400> SEQUENCE: 41
ccttccacac gctcaggttg gcacggaggg ggtgtccttg cctgaggggt cctggcacag    60
ycatcagggc acacagctga taacccaagg gagcagtagg caagacctca tgggcgccgg   120
g                                                                   121

<210> SEQ ID NO 42
<211> LENGTH: 121
<212> TYPE: DNA
<213> ORGANISM: Canis familiaris

<400> SEQUENCE: 42
attctctttg ctgtctcctg tatacagaga taaaagcaag agttttcccc ttcaggtttc    60
ygaaacccag cttcctttag attttaaggg gtattctgtg tacccatttc ccaccttctg   120
c                                                                   121

<210> SEQ ID NO 43
<211> LENGTH: 121
<212> TYPE: DNA
<213> ORGANISM: Canis familiaris

<400> SEQUENCE: 43
gcgggttggg accccccctt ctgctgctcc cacttcagag ttgtggcgtc actaagatga    60
sacctcatgt cgggaacctg agagtccctc gggagttgtg cagggactgt agccgaccta   120
t                                                                   121

<210> SEQ ID NO 44
<211> LENGTH: 121
<212> TYPE: DNA
<213> ORGANISM: Canis familiaris

<400> SEQUENCE: 44
acatatgcac agtgaatcgt ggattgttgt gtttgatttc ttacatgata caataaaagg    60
raagtagttg aagcaaaact ttagtttaaa ggaaacaatt tctctatcat aatgttcagt   120
g                                                                   121

<210> SEQ ID NO 45
<211> LENGTH: 121
<212> TYPE: DNA
<213> ORGANISM: Canis familiaris

<400> SEQUENCE: 45
cccacagacc ccaggtgctg accacagcag ccacttgggc ccccaatgca ggagacacct    60
ygggaatgaa ggggacaagg ccagctcagg cacatcgtca gtgcacctga tgggaaggcc   120
g                                                                   121

<210> SEQ ID NO 46
<211> LENGTH: 121
<212> TYPE: DNA
<213> ORGANISM: Canis familiaris

<400> SEQUENCE: 46

```
atctgatcct agccaatgga aagcaatttg agataggaat catatcttgt tttggtttat    60
rtgctttctt tggagttttg cacatcatag ataactgtaa atttgtagaa taaatgtttg   120
a                                                                   121
```

<210> SEQ ID NO 47
<211> LENGTH: 121
<212> TYPE: DNA
<213> ORGANISM: Canis familiaris

<400> SEQUENCE: 47

```
gtcaatgcca ttaacctggc gaagctgctc gagcatccac tgcgatctcc gcacgaacga    60
ygtggagcct tcaaactgtt tgaccttcgt gatggatgct tgtgtgggtt tcttgtttgt   120
c                                                                   121
```

<210> SEQ ID NO 48
<211> LENGTH: 121
<212> TYPE: DNA
<213> ORGANISM: Canis familiaris

<400> SEQUENCE: 48

```
actggttaat aagacttcac agattttatc catcatgttg attatctgta tatgtatttt    60
ytaccactta ggataaagtt ctgttatctg taattgattc caaccagcat gtttgctcca   120
a                                                                   121
```

<210> SEQ ID NO 49
<211> LENGTH: 121
<212> TYPE: DNA
<213> ORGANISM: Canis familiaris

<400> SEQUENCE: 49

```
cttcttcttt cccattggat tctttcatca atcgtaggta gttcttaatg aagatctgtg    60
rtaaagccat tcatctattc attcaacaaa tggcatcaca gaaagaaaaa ataacccttta  120 t                                                                   121
```

<210> SEQ ID NO 50
<211> LENGTH: 121
<212> TYPE: DNA
<213> ORGANISM: Canis familiaris

<400> SEQUENCE: 50

```
gggacacatt tctggacaga cctctgatca cactcacagg acagcaagag gaagctctgg    60
rtacaagtac agggaaaaaa gaaagaaatg gtcacaggga agctgccgca ggaaaaaggt   120
a                                                                   121
```

<210> SEQ ID NO 51
<211> LENGTH: 121
<212> TYPE: DNA
<213> ORGANISM: Canis familiaris

<400> SEQUENCE: 51

```
gggcagatcc tcagtgagta ttggctcatg ttctccgagg gaagtagagt cccagaagaa    60
rgatgctaag gtgccaagat tcctgagcct gtgtgtggta cagtcacagc agtactcctg   120
a                                                                   121
```

<210> SEQ ID NO 52
<211> LENGTH: 121

<212> TYPE: DNA
<213> ORGANISM: Canis familiaris

<400> SEQUENCE: 52

```
tcatctccat tgtaataga aaccacatat atagagagat tggattatta accactaaaa    60
ytagccact caaggggagg gggggaatgc atttggttta tttcccatgt caaaacagaa   120
t                                                                 121
```

<210> SEQ ID NO 53
<211> LENGTH: 121
<212> TYPE: DNA
<213> ORGANISM: Canis familiaris

<400> SEQUENCE: 53

```
aacactgcta ataaatattt ataatggttt gaggaaaata tcaggtgtga gatgtcttca    60
yatcatataa tatatcataa tatcctctaa aaaagctcta agcataggtc tatgggaactc   120
a                                                                  121
```

<210> SEQ ID NO 54
<211> LENGTH: 121
<212> TYPE: DNA
<213> ORGANISM: Canis familiaris

<400> SEQUENCE: 54

```
aagcaatcca ggagtctttc tccgggtagc aggctcgctt tacaggttaa ggctggatga    60
raaggaagaa cctgagcttc aaattatcat ctgagtagag ctgataccca tggttacatt   120
a                                                                  121
```

<210> SEQ ID NO 55
<211> LENGTH: 121
<212> TYPE: DNA
<213> ORGANISM: Canis familiaris

<400> SEQUENCE: 55

```
gattttattc tttactttga tttttttaa gttttactat gatattcaat atgattgtgg    60
ytcatgagat tcctcttttt agctgtatca ttaactacag agcgttctca aatattttc   120
t                                                                 121
```

<210> SEQ ID NO 56
<211> LENGTH: 121
<212> TYPE: DNA
<213> ORGANISM: Canis familiaris

<400> SEQUENCE: 56

```
gtggccggag ggggtgggcc ctactgtggc ccagcttcac gtcccactgg ccaaacatca    60
rgatgcagac acccaggtcc cttgtgctgc ctgctgaggc taggagcagc gactggaaat   120
g                                                                 121
```

<210> SEQ ID NO 57
<211> LENGTH: 121
<212> TYPE: DNA
<213> ORGANISM: Canis familiaris

<400> SEQUENCE: 57

```
gatgggagac ctcatacaca tgcaaagatc actattaaag actctcgagc aaagatcgaa    60
yggactgtgg caagctgccg cgcatgccaa tcaacaaatg cctccgacca tggatctaac   120
``` c                                                                      121

<210> SEQ ID NO 58
<211> LENGTH: 121
<212> TYPE: DNA
<213> ORGANISM: Canis familiaris

<400> SEQUENCE: 58
caacaaggtt tttaaggttc ttttcactac cttcttcttt ttgtacttgc ttaggacacc      60
ygtatgtctt cacaatatca cctgaaagtc ctttaggaga tatactcaaa aaataaataa    120
a                                                                    121

<210> SEQ ID NO 59
<211> LENGTH: 121
<212> TYPE: DNA
<213> ORGANISM: Canis familiaris

<400> SEQUENCE: 59
caacctgagc tgaaggcaga cactcaactg ttgagctacc caggtgtacc aaacacatct     60
rctcttaacc aagcttattc tttgctatat ttggcaaatt gtggcatgtc tacagtactc    120
a                                                                    121

<210> SEQ ID NO 60
<211> LENGTH: 121
<212> TYPE: DNA
<213> ORGANISM: Canis familiaris

<400> SEQUENCE: 60
attccccatg tttgaggaaa tcacaggagc cactaggaaa tcaaccattt cccaaccaac     60
ytgatgattt cctgatccaa aggttctccc aggacaaata tgaggtagcc tttcacactc    120
t                                                                    121

<210> SEQ ID NO 61
<211> LENGTH: 121
<212> TYPE: DNA
<213> ORGANISM: Canis familiaris

<400> SEQUENCE: 61
cagtcttgta ggagagtaga ttgactcaca gaactggcaa gattgggaat ctgagcattg     60
ycacttgagt cttaaaacgt ttacgatttt atttctagta tttcaataag aaacacattc    120
t                                                                    121

<210> SEQ ID NO 62
<211> LENGTH: 121
<212> TYPE: DNA
<213> ORGANISM: Canis familiaris

<400> SEQUENCE: 62
gaatacattg ccagaataat ttcaagttct caaatctcaa ctaataagat tttcgttaaa     60
kaaggcattc aatcatcact tactgacaac ccacaaaatt aggcactgat gaaaaattag    120
c                                                                    121

<210> SEQ ID NO 63
<211> LENGTH: 121
<212> TYPE: DNA
<213> ORGANISM: Canis familiaris

<400> SEQUENCE: 63

```
aagttaagat attcaagaaa gagaagagag tgactgagct aaaaagaaaa tcagatctct    60
yccaggcttt aaaataatct ccacaatact gggcaatcca tgtagtctcc ccagttccat   120
t                                                                   121
```

<210> SEQ ID NO 64
<211> LENGTH: 121
<212> TYPE: DNA
<213> ORGANISM: Canis familiaris

<400> SEQUENCE: 64

```
ctcaaaagga aaagcctgtg aaaggcaaa gaggtatgtg aaagaggtaa gttcaaaatg     60
stgacatgac cagtgtacat agattacagg gtacttggag gagcagtgag aaaggagtcc   120
a                                                                   121
```

<210> SEQ ID NO 65
<211> LENGTH: 121
<212> TYPE: DNA
<213> ORGANISM: Canis familiaris

<400> SEQUENCE: 65

```
ttctatgaaa tagctaccat tctggttggt atcttctgtt gatttagatg atgaaggaag    60
yataagaagt aaggcttatg agtttataaa gctttagtta aagctttgat tgtgacaaag   120
c                                                                   121
```

<210> SEQ ID NO 66
<211> LENGTH: 121
<212> TYPE: DNA
<213> ORGANISM: Canis familiaris

<400> SEQUENCE: 66

```
agaggagaaa acacagctaa aaactttttt acagactgga caaaggtgct tacactttc     60
rtattgggca gaatgagggg atgaaaacac cagtggtctt tttgaagcca cacaaattca   120
g                                                                   121
```

<210> SEQ ID NO 67
<211> LENGTH: 121
<212> TYPE: DNA
<213> ORGANISM: Canis familiaris

<400> SEQUENCE: 67

```
aggatgaata tttattaaca gtaaatatac attttattg ttctatatac tctaaagaca     60
rttgtagaca gtaagatata tcaattttag aaacagaaat aatgttaatt gtataatatg   120
g                                                                   121
```

<210> SEQ ID NO 68
<211> LENGTH: 121
<212> TYPE: DNA
<213> ORGANISM: Canis familiaris

<400> SEQUENCE: 68

```
cagggattcc taaagggtga catggtatgg tctaacactt cctcactgtc cttttcccag    60
mtgatataag aggaggacca gagagacaca taaactgtct gagtctttag cattgtgata   120
a                                                                   121
```

<210> SEQ ID NO 69

```
<211> LENGTH: 121
<212> TYPE: DNA
<213> ORGANISM: Canis familiaris

<400> SEQUENCE: 69
acactaatgg gtagagaata cacgtccatc agtcatcaat gtaatctact aacagcctca      60
sagtctggca gttttcagtg aaaagaggag tcatctccat ttattcgatc aatcagttga     120
c                                                                    121

<210> SEQ ID NO 70
<211> LENGTH: 121
<212> TYPE: DNA
<213> ORGANISM: Canis familiaris

<400> SEQUENCE: 70
tattaccctg ctctccagcc actcctttac cttccattag cccacacctg ctctacacac      60
yattgctcat ggaagccttg ccacgtccag tcgccactct gaaatgccag catccctccc     120
a                                                                    121

<210> SEQ ID NO 71
<211> LENGTH: 121
<212> TYPE: DNA
<213> ORGANISM: Canis familiaris

<400> SEQUENCE: 71
tctcagatac ttgatagcca gcatttcccc ccattttctt ccaagagcac gaaagcatag      60
raatgatatt acatctcgta tggtgaatgt gacacagccg tcagttgcgt tagctctgct     120
t                                                                    121

<210> SEQ ID NO 72
<211> LENGTH: 121
<212> TYPE: DNA
<213> ORGANISM: Canis familiaris

<400> SEQUENCE: 72
acaggaagga gaactgagca tcaagagagt tcagaacatg atcattgggt cagtttgtgg      60
stgcattaac ttttccccaa aacagaaagc aacagagact tctgtaggtc agtcaacagt     120
g                                                                    121

<210> SEQ ID NO 73
<211> LENGTH: 121
<212> TYPE: DNA
<213> ORGANISM: Canis familiaris

<400> SEQUENCE: 73
ttaccattac tataacccaa gttatagtat actataacca agtccttaat tgacttgatg      60
yttgtgcagc tgattttaaa tctatttaga ataatagttt acttgtgaca attcatatta     120
a                                                                    121

<210> SEQ ID NO 74
<211> LENGTH: 121
<212> TYPE: DNA
<213> ORGANISM: Canis familiaris

<400> SEQUENCE: 74
ttggtcgact gactgattgg ttttactgtg gaggaaagaa aagggaattt tcccaaagag      60
racagagaga aaacatggaa ttgagcaaag ggagaataga gagacagggc agccactgaa     120
```

```
g                                                                      121

<210> SEQ ID NO 75
<211> LENGTH: 121
<212> TYPE: DNA
<213> ORGANISM: Canis familiaris

<400> SEQUENCE: 75
tgccttatcc tccagctcct ccctcaccat cttggaaact agctcaaatg tcactggtac      60
ktgtctttct tttgatcttt ctgaaagaca aacatgatcc catcacctct gcctttagaa     120
c                                                                     121

<210> SEQ ID NO 76
<211> LENGTH: 121
<212> TYPE: DNA
<213> ORGANISM: Canis familiaris

<400> SEQUENCE: 76
actcctaagt aaaagttaaa ttaacagatt tgccatcaag taccttgccc attttcccta      60
yagatcgact ttttactgga tgatcccctt gataataatc ttgatctatg ttttaattcc     120
a                                                                     121

<210> SEQ ID NO 77
<211> LENGTH: 121
<212> TYPE: DNA
<213> ORGANISM: Canis familiaris

<400> SEQUENCE: 77
ctggtgggct tgtcaggggc aggatgttgt gtggtgagca cagaattaaa actaggagct      60
ygaagcgcct gggggggctca gttggttgac ggactgcctt catctcaggt catgatccct    120
g                                                                     121

<210> SEQ ID NO 78
<211> LENGTH: 121
<212> TYPE: DNA
<213> ORGANISM: Canis familiaris

<400> SEQUENCE: 78
catacagcga agagataaaa acacaggatg ctgggctcac gaccatgacc ggaaaaggac      60
rgcgaggaaa agcaagtatg agcagcccaa agtcctttt ccagcactgg ccataggagg      120
a                                                                     121

<210> SEQ ID NO 79
<211> LENGTH: 121
<212> TYPE: DNA
<213> ORGANISM: Canis familiaris

<400> SEQUENCE: 79
cagagatgag gaatcagact cctcgtcctc tgcttctcta caatggctca tgttctcctt      60 yccctcagc tgttgcatta acagaggtca acccattctt ctaaatttaa atctcccaga     120
a                                                                     121

<210> SEQ ID NO 80
<211> LENGTH: 121
<212> TYPE: DNA
<213> ORGANISM: Canis familiaris
```

<400> SEQUENCE: 80
aatcaaacaa gtgctagaac atagaacaag tggctcatct tttccccaaa tgtctggata    60
rgaaaaaaaa aatctaaaca aatgctagat gttaagtatc tgaaatgatc agcccatgaa   120
a                                                                  121

<210> SEQ ID NO 81
<211> LENGTH: 121
<212> TYPE: DNA
<213> ORGANISM: Canis familiaris

<400> SEQUENCE: 81
tccataccag tccttgttgt ctaccccgaa cttcacctct ctaggcacag acagctctaa    60
mtttcactca taggtatctt atgctgacct ggcctgcctc ctgttttgtt ttgttttgtt   120
t                                                                  121

<210> SEQ ID NO 82
<211> LENGTH: 121
<212> TYPE: DNA
<213> ORGANISM: Canis familiaris

<400> SEQUENCE: 82
caaaaaattc cctgagccca gcatcaaggt acctggtttg gagtgggtgg gtcctcagaa    60
mgaatgggtg tggtgtacat ttagcaagtt atgtagcatg tgtctgtgta gtctcacctc   120
t                                                                  121

<210> SEQ ID NO 83
<211> LENGTH: 121
<212> TYPE: DNA
<213> ORGANISM: Canis familiaris

<400> SEQUENCE: 83
gggcccagca agtggcagaa ctgggaagac cccctcttct tccgcctgga gcagtggtgt    60
rgcagcacac cacaggagtc tgaaagggtg gggagtccaa acgggaacat atacctgaga   120
t                                                                  121

<210> SEQ ID NO 84
<211> LENGTH: 121
<212> TYPE: DNA
<213> ORGANISM: Canis familiaris

<400> SEQUENCE: 84
atataatata acttatttaa aatatttgaa gatatttcta tagttatgct ctaccatttg    60
ytattataag atttccaaca gcttacttct tgtatgaaat taatttacca gcccctcacc   120
t                                                                  121

<210> SEQ ID NO 85
<211> LENGTH: 121
<212> TYPE: DNA
<213> ORGANISM: Canis familiaris

<400> SEQUENCE: 85
ccctattcta taaacattcc ctctctggcc atcctgtcaa gtgggccctg acagtgtgcc    60
scagaagctc cctagccttt gcccattcca gctatggcta gcctgccacc agccatacac   120
a                                                                  121

<210> SEQ ID NO 86
<211> LENGTH: 121
<212> TYPE: DNA
<213> ORGANISM: Canis familiaris

<400> SEQUENCE: 86

```
cactgtgagg tctgaatgga dacattcatg atagactcca ggattttccc agctattaag      60
ycatgggcca taaactggaa cacttggaaa cagtccatag gttcatatta aagaatatgt     120
t                                                                    121
```

<210> SEQ ID NO 87
<211> LENGTH: 121
<212> TYPE: DNA
<213> ORGANISM: Canis familiaris

<400> SEQUENCE: 87

```
gcaaaaggaa catgagttct gatcttctgt aaaggaggct aatttactaa tggtcataac      60
ygtggcctga gggtcaagtt tctaattaaa cgtgcatctt ggggyggact agaatacttt     120
c                                                                    121
```

<210> SEQ ID NO 88
<211> LENGTH: 121
<212> TYPE: DNA
<213> ORGANISM: Canis familiaris

<400> SEQUENCE: 88

```
caaggsccag gtaccctgaa ggagtccgct tcacccaggc atgatgtgtt tgacagtctt      60
ygtaattgat acagccattg gcatcctctt gcggccaaya tcagctccac ttcaacctcg     120
g                                                                    121
```

<210> SEQ ID NO 89
<211> LENGTH: 121
<212> TYPE: DNA
<213> ORGANISM: Canis familiaris

<400> SEQUENCE: 89

```
tgcaatgggt tttgaaatta gaggacatca cagcagagta gaatggtttg gaacagggga      60
rtatgattag gattaatgag atgaaagaaa attctggcta gagggctaga agagccatgg     120
a                                                                    121
```

<210> SEQ ID NO 90
<211> LENGTH: 121
<212> TYPE: DNA
<213> ORGANISM: Canis familiaris

<400> SEQUENCE: 90

```
ctcagaacta gataggctaa taagtgatag gccttgtgtt ttcctagagt gtgctttaaa      60
rgtttcttaa gctaaaaaat tacattcgtg agaaaattga aataaaagga aaacagtcat     120
g                                                                    121
```

<210> SEQ ID NO 91
<211> LENGTH: 121
<212> TYPE: DNA
<213> ORGANISM: Canis familiaris

<400> SEQUENCE: 91

```
gatactttgg gctctgggtg ggagccagca gtggtgggc agggcaggag tccagcaagg      60
```
ygtctgggca tacatgtctg agagtaggaa aaccacacca ttgcaccttg cctttgactt    120
c                                                                    121

<210> SEQ ID NO 92
<211> LENGTH: 121
<212> TYPE: DNA
<213> ORGANISM: Canis familiaris

<400> SEQUENCE: 92
tcaaggatca gaaaataaa agcaaagaaa gaggcaaaga aagaagaaat gaaatacccta    60 rtggcagaag taggcagaga aataaaggct aaaagaaaat ggcagaggat tgtttgaaag    120
g                                                                    121

<210> SEQ ID NO 93
<211> LENGTH: 121
<212> TYPE: DNA
<213> ORGANISM: Canis familiaris

<400> SEQUENCE: 93
tatgttatac tattttagta tcttaataaa tatgattagc caaaatagtt ttatcatcct    60
saaaagtgca gcatatatta ttttctatta aattcagaat aggtataaac tagaaagcat    120
t                                                                    121

<210> SEQ ID NO 94
<211> LENGTH: 121
<212> TYPE: DNA
<213> ORGANISM: Canis familiaris

<400> SEQUENCE: 94
acagcagttc tgaggatgga ctcgcagagg ctcctgacaa gcagaatgac caggccgagc    60
rgaaaggtca gtgctgccag tctagccaga agtgggggag agaggatgta ggagcagtac    120
t                                                                    121

<210> SEQ ID NO 95
<211> LENGTH: 121
<212> TYPE: DNA
<213> ORGANISM: Canis familiaris

<400> SEQUENCE: 95
actgtactca aaaaagttct gtttgcctaa atgggatcag cctctaatgg atgccagtga    60
ygggaggctg ttcatcatcc cttcgggata attcagagcc taggcagagg cccagcgttc    120
a                                                                    121

<210> SEQ ID NO 96
<211> LENGTH: 121
<212> TYPE: DNA
<213> ORGANISM: Canis familiaris

<400> SEQUENCE: 96
tacaggcccc aggaaggagc caccagatgc ccaggactgg gcccaggaat gatggaggct    60
rtacagctgg ctgcctgcac tggctgccgc ccctgtcatc cagtgtcaca gagcagcacc    120
t                                                                    121

<210> SEQ ID NO 97
<211> LENGTH: 121
<212> TYPE: DNA
<213> ORGANISM: Canis familiaris

```
<400> SEQUENCE: 97
agacattgcc aagaagtatc cacaatgaac agtttgaagg ggatccagaa aagcacaggg      60
yctacttccg ctggatgagc agcagtgaga accacagtca ggtaggtctt aaagcaaagt     120
t                                                                    121

<210> SEQ ID NO 98
<211> LENGTH: 121
<212> TYPE: DNA
<213> ORGANISM: Canis familiaris

<400> SEQUENCE: 98
gctttgaaaa ccaacaggaa atacatccag gaaagctata caactgtggt gaaaggaaag      60
raaaatctgc tcttaaaagg ttgtgtgcag actcacttgc cccagaaacc agtgcgaaaa    120
c                                                                    121

<210> SEQ ID NO 99
<211> LENGTH: 121
<212> TYPE: DNA
<213> ORGANISM: Canis familiaris

<400> SEQUENCE: 99
gagatgtgta aaatttaata gaaatgaaac ttgccaaaac agacctctgt actcgtcagc      60
rttctaagtc catctttctg tagcatgtaa gtagaataat gttctattaa tttcctctat    120
g                                                                    121

<210> SEQ ID NO 100
<211> LENGTH: 121
<212> TYPE: DNA
<213> ORGANISM: Canis familiaris

<400> SEQUENCE: 100
gttctttcta ttctatcaca cataccaccc ccctgcccac agtacccctt tctgccatgt      60
ytcagactcc tacacaagag gttctctctc ctggcttcca gttagacagg caggtaaagc    120
t                                                                    121

<210> SEQ ID NO 101
<211> LENGTH: 121
<212> TYPE: DNA
<213> ORGANISM: Canis familiaris

<400> SEQUENCE: 101
taaaaaaata caacagtagc attagaagac atgctaagcg gctgtattag agaaggttag      60
ygctggcctg aagtttagaa accttccctt ctctttttt ttttccttcc cttctctta     120 a                                                                    121

<210> SEQ ID NO 102
<211> LENGTH: 121
<212> TYPE: DNA
<213> ORGANISM: Canis familiaris

<400> SEQUENCE: 102
tcaagagtac tagagcatct ataatcaatg gtaaattggg gaactagtga aacaagttta      60
yaggacaaat aacataaata aggattttt tttaaatttg gaaaattgtg gaataatgat    120
a                                                                    121
```

<210> SEQ ID NO 103
<211> LENGTH: 121
<212> TYPE: DNA
<213> ORGANISM: Canis familiaris

<400> SEQUENCE: 103

```
agaattcaat tttggggagc caggaaacca gattagtttt ccaaagggaa gtgccatttg    60
yatctatccc ggtggggctg ccaagaattc cctggggtgg agacggcgc ttctgtggat    120
t                                                                    121
```

<210> SEQ ID NO 104
<211> LENGTH: 121
<212> TYPE: DNA
<213> ORGANISM: Canis familiaris

<400> SEQUENCE: 104

```
caccagagag ccccgcaaga tcatactgca caagggctcc actggcctgg gcttcaacat    60
ygtaggagga gaggatggag aaggcatttt tgtttccttc atcctggcag gaggcccagc    120
t                                                                    121
```

<210> SEQ ID NO 105
<211> LENGTH: 121
<212> TYPE: DNA
<213> ORGANISM: Canis familiaris

<400> SEQUENCE: 105

```
tggtgatgat ttatccccca tgttcaagat ttatcctccc tgtctcaaga aatcatgtca    60
ytacaggcat ccttaaagtc acaagactgg gaagtaaata ctgatgaggt ccaagacctg    120
g                                                                    121
```

<210> SEQ ID NO 106
<211> LENGTH: 121
<212> TYPE: DNA
<213> ORGANISM: Canis familiaris

<400> SEQUENCE: 106

```
agcatagtgt acccacatat aaggtcacat ctgaggccag ggagtcgggg tcttgaagat    60
katgactgat catgtgcttg aggatgatga tgatcatgtg cttttcctgg ctgtgcagtt    120
g                                                                    121
```

<210> SEQ ID NO 107
<211> LENGTH: 121
<212> TYPE: DNA
<213> ORGANISM: Canis familiaris

<400> SEQUENCE: 107

```
gtgtgtgtgt gtgtgtgtgt gtgtttaatt ctttgtgaga agcccctcat tttgacctaa    60
rtttggtaga ggccccaggg gatctgagag gagaacaaaa ggataaacca tttgctgttc    120
a                                                                    121
```

<210> SEQ ID NO 108
<211> LENGTH: 121
<212> TYPE: DNA
<213> ORGANISM: Canis familiaris

<400> SEQUENCE: 108

```
ccaactttca ctagcatcac agccccctatc aatctctgtt cttttttctg tcagtaccat   60
```

```
rtttgctcct actacatcya atctgtgagc tcacaggatg aggaccaaca gctgccctga    120
g                                                                   121

<210> SEQ ID NO 109
<211> LENGTH: 121
<212> TYPE: DNA
<213> ORGANISM: Canis familiaris

<400> SEQUENCE: 109
tgtcttacct ctctctattc ccttgtccat agtagtatta aatatatctt cctgaacaca    60
ratctgatcc agtctctttt tgtaattaaa gcctttgct agctttggtg atcacctcca    120
g                                                                   121

<210> SEQ ID NO 110
<211> LENGTH: 121
<212> TYPE: DNA
<213> ORGANISM: Canis familiaris

<400> SEQUENCE: 110
gacctgacag attatgtaga ctttgttttc aaagggagca cctgctggat atacaacatg    60
rcactaaatt gtgctccaca tccttggcag aggtggggggg cggggcacaa aggaagaaac   120
c                                                                   121

<210> SEQ ID NO 111
<211> LENGTH: 121
<212> TYPE: DNA
<213> ORGANISM: Canis familiaris

<400> SEQUENCE: 111
cagaggaaaa ggagaaggtc ccacttaggg gactggagag gagtggggga acatcaccag    60
mgccttcctg agccaggccc cctgtgggga gaagctctcc ccaggactgg gtgcctttga    120
a                                                                   121

<210> SEQ ID NO 112
<211> LENGTH: 121
<212> TYPE: DNA
<213> ORGANISM: Canis familiaris

<400> SEQUENCE: 112
tcctccctct ccccatcccc attctcatgc aagtgtgctc tctctctaaa acaccccccc    60
mcacacacac acacagacac aaccaaattt gggtctcaat gtcttgacca aggaaaaggc    120
a                                                                   121

<210> SEQ ID NO 113
<211> LENGTH: 121
<212> TYPE: DNA
<213> ORGANISM: Canis familiaris

<400> SEQUENCE: 113
gagaagaagg aggagaaaga ggaaaagtat atttgatgga atgaaaaaca agagttcaat    60
ytcactctgg tctggggtga ccactattag tccttcaaca tcttccttga aggaattttta  120 a                                                                   121

<210> SEQ ID NO 114
<211> LENGTH: 121
<212> TYPE: DNA
```

-continued

<213> ORGANISM: Canis familiaris

<400> SEQUENCE: 114

```
ctggaattct gtcagatcaa cattcagagc tccatcaaat ctgagggaag cagtgataga    60
rgatacaatt tgacctttca gtctattcag gttcatgtag gttaggcatt caatatcaaa   120
g                                                                  121
```

<210> SEQ ID NO 115
<211> LENGTH: 121
<212> TYPE: DNA
<213> ORGANISM: Canis familiaris

<400> SEQUENCE: 115

```
ccacatgtgg ttacaccact gtgttatcct tccacctgtc ccatcaaccc acccgcacat    60
rtcacagtgc ctctgtcctc aaagaacact gtatccaaca cctccacatc ctctcagcat   120
g                                                                  121
```

<210> SEQ ID NO 116
<211> LENGTH: 121
<212> TYPE: DNA
<213> ORGANISM: Canis familiaris

<400> SEQUENCE: 116

```
attcctatgg tgggcgctgc acatttcctc ccaggggaag ggcaagggtc ctgcatttct    60
rtgctttcca gggcctccgc accaagagca attgctaggt cacgcatgcc cctgcacttc   120
c                                                                  121
```

<210> SEQ ID NO 117
<211> LENGTH: 121
<212> TYPE: DNA
<213> ORGANISM: Canis familiaris

<400> SEQUENCE: 117

```
catgtcatca ctaactaatt tattaacaag agttttattc tttgaaaaac aaaatcactc    60
rcattactca gttgcttatt ccttgattca tatacaaatg actgataaca tgagataaaa   120
a                                                                  121
```

<210> SEQ ID NO 118
<211> LENGTH: 121
<212> TYPE: DNA
<213> ORGANISM: Canis familiaris

<400> SEQUENCE: 118

```
gatgatttag ttgtttgaat gatctggcat ataaatcttc caaatctgtg tccattggat    60
ygcttacagt ttaatctttt tatttcttcc cagaatcaca tttttcatt atttatcttt   120
g                                                                  121
```

<210> SEQ ID NO 119
<211> LENGTH: 121
<212> TYPE: DNA
<213> ORGANISM: Canis familiaris

<400> SEQUENCE: 119

```
agttaaattc tgtgaataac tagaatccgt tatactttt ctgaaatgaa gtctgtaggc    60
wtttcaacag caaaggaat tctgwtttty aaaactatac ataatgcttc ttaaaagccc   120
t                                                                  121
```

<210> SEQ ID NO 120
<211> LENGTH: 121
<212> TYPE: DNA
<213> ORGANISM: Canis familiaris

<400> SEQUENCE: 120
aatgccaact ttaaaaacgc attcaaggtt ttcctctgta aatgcattcc tcattttgga    60
ygtgatgtaa aatcttattc agtgttttgt ttttttttcc ccccacaggt ctcaacaatt   120
a                                                                  121

<210> SEQ ID NO 121
<211> LENGTH: 121
<212> TYPE: DNA
<213> ORGANISM: Canis familiaris

<400> SEQUENCE: 121
ggtgggaccg gccatcagca ggcgggccag cgccccacag atgttgtcac ggacccgatc    60
rtggcgctcc cgtgccagga ggggcaacag aagccccagc agcttgggga agtatctggt   120
t                                                                  121

<210> SEQ ID NO 122
<211> LENGTH: 121
<212> TYPE: DNA
<213> ORGANISM: Canis familiaris

<400> SEQUENCE: 122
aggggacttg tgctaatcac tgggcaaatt ttatgaactt ctgaatttta aagcaaaaga    60
raaggtgaaa gaatggaaag aaggtgtgag tgtttgagga aaacttcttc tttggggttg   120
a                                                                  121

<210> SEQ ID NO 123
<211> LENGTH: 121
<212> TYPE: DNA
<213> ORGANISM: Canis familiaris

<400> SEQUENCE: 123
tacacaagca aggcagtatg ccctgtctcc ttcccttggg ccacctgcac ttagacatgg    60
yaggttccag tgatgtgtct agtctctagc aagcagggct tgcttctgct ctatccatcc   120
a                                                                  121

<210> SEQ ID NO 124
<211> LENGTH: 121
<212> TYPE: DNA
<213> ORGANISM: Canis familiaris

<400> SEQUENCE: 124
ctgtccttgg tctggacctg ctgtgaagac caagtgcttc ctgagatctc tctgagtcta    60
rtttccagag cagtgagtga gaaatgaaat gagccgagga ttgccctccc tcctatggac   120
t                                                                  121

<210> SEQ ID NO 125
<211> LENGTH: 121
<212> TYPE: DNA
<213> ORGANISM: Canis familiaris

<400> SEQUENCE: 125

```
taagccatca gcatgggctc ctaggggtct gttcaactcc cttgtggtgt cttactgctc      60
ragcaaagga acagtctggt acagtgggag caagagctga ggttggagag tggggacaca     120
g                                                                     121

<210> SEQ ID NO 126
<211> LENGTH: 121
<212> TYPE: DNA
<213> ORGANISM: Canis familiaris

<400> SEQUENCE: 126
gaggaggtgg aagtgattaa gtttaaaatt tctggggtgg tttctggcga catgaagctg      60
mgagctagaa tgcctttcaa tctcataatt tctttaattt ggtgattata ccagagccac     120
a                                                                     121

<210> SEQ ID NO 127
<211> LENGTH: 121
<212> TYPE: DNA
<213> ORGANISM: Canis familiaris

<400> SEQUENCE: 127
cctgacaaac actacctctg ctcttcaaaa gcaataagca tttattctgt gacacattta      60
ratacaaagt caattacaat agagtataag tacaatacta gggaaagtac aaagtcatay    120
g                                                                     121

<210> SEQ ID NO 128
<211> LENGTH: 121
<212> TYPE: DNA
<213> ORGANISM: Canis familiaris

<400> SEQUENCE: 128
gcatgatgaa atcagaaaaa gtatgtaagt ttctagaaga agctagatat atggtaactt      60
wggtcaaata gaaccatgta gtgaaaagaa tatgagtttt caagttcaat aaaaaacaaa    120
a                                                                     121

<210> SEQ ID NO 129
<211> LENGTH: 121
<212> TYPE: DNA
<213> ORGANISM: Canis familiaris

<400> SEQUENCE: 129
atgcataagt ttccaaaaga gttcaggatt ccaaaataaa agcttcacta aaagattcat      60
mgcaaaagag taatgaacaa ttaaagtcat aggatatcta aaatgaaaaa ctgttagact    120
g                                                                     121

<210> SEQ ID NO 130
<211> LENGTH: 121
<212> TYPE: DNA
<213> ORGANISM: Canis familiaris

<400> SEQUENCE: 130
agatggctta gttgtttctc tttcctcctg aagtccacag cttagttact tggactctcc      60
raaataggat cgttggacat ttgaggaaag ctctagcatg aaagccatag actaaaaaac    120
a                                                                     121

<210> SEQ ID NO 131
<211> LENGTH: 283
```

```
<212> TYPE: DNA
<213> ORGANISM: Canis familiaris

<400> SEQUENCE: 131
ctctcatttt gtgtattgat ttgaggactc tgtcctttt gttctcttag gtgttttgta      60
accatttttg tggttcttgc cacaaaaggc cttatgaagt cctgcatatg agtgatgtgc    120
aggacaactt tgactttctg acagccagtt tttgtgtttt gttmccttag ttcccaagtt    180
cctatcttgt ttacctcatg atcacatttt aatatcaatg aaatttgtag gaaaacagca    240
gaaggaaaga tataaggtta ctattctcta tggaccttgg ttg                      283

<210> SEQ ID NO 132
<211> LENGTH: 223
<212> TYPE: DNA
<213> ORGANISM: Canis familiaris

<400> SEQUENCE: 132
ttgcagatta tatgataaat atagttgtag cttcaaaaat gactataacg aacagaaaaa     60
aattaactta tcaaaaactt ttcaaatttc cccatayact taactaggta ggccacagag    120
tatgatagta tgcaagttat taaaatctgt tagcaaggca taacacatat atttctactt    180
aatgaggttt ctataatcaa ggcttgtcaa gtccattatg ttc                      223

<210> SEQ ID NO 133
<211> LENGTH: 157
<212> TYPE: DNA
<213> ORGANISM: Canis familiaris

<400> SEQUENCE: 133
tcagactgaa tctaaagcca catatatttc ctcagcagct gataacatta gaaatcagaa     60
agccactaty ttagctggca ccgcaaatgt aaaagtaggc tctaggacgc cagtggaggc    120
ttcccatcct attgaaaatg catctgttcc taggcca                             157

<210> SEQ ID NO 134
<211> LENGTH: 179
<212> TYPE: DNA
<213> ORGANISM: Canis familiaris

<400> SEQUENCE: 134
tcttgtgctt gttctttatc accattcatt cagtacatcc aaattttgaa atccttagag     60
ctctatagcc tctatgtagg agaatgarat ttcatcaaaa ggaaatattt tgagaattta    120
agtgattttt ttatgatatt ttagctatag cagtcaccct gagccaaaag acattctac    179

<210> SEQ ID NO 135
<211> LENGTH: 191
<212> TYPE: DNA
<213> ORGANISM: Canis familiaris

<400> SEQUENCE: 135
aaaaatatac tctctttctt acagaaacct ctaataattc agattctggc catgaagttc     60
aggaggattc ttcaaaggaa aatgtatcat caagtgctgc ctcyactgac cacaacccaa    120
cacctactca tgatggcaaa tcmcmtraac tgtytawtyt csgattggrr awtmaaykgt    180
traggaatga a                                                         191

<210> SEQ ID NO 136
<211> LENGTH: 244
<212> TYPE: DNA
```

<213> ORGANISM: Canis familiaris

<400> SEQUENCE: 136

| tttgcccaag aaaaatgaag acctatgacc atggaaagac ttgatacata atgctggagt | 60 |
| actagtagtc agacccaccc aagtcttttc acgtgttcat tcagtataga tgcggcacac | 120 |
| gttggctgag tccctccgkt gtgtcaggaa ctgttttagg tattggggat gaagtaggga | 180 |
| acactgattt agsttctgtt tattcatgtc tcactttgta ggaattycmh tamatagaar | 240 |
| aada | 244 |

<210> SEQ ID NO 137
<211> LENGTH: 251
<212> TYPE: DNA
<213> ORGANISM: Canis familiaris

<400> SEQUENCE: 137

| tctcagtact cacaggtact tacaaataca acactaagag gtttcacaaa acagtactct | 60 |
| tacatagcac atgctgtact ctctgttcca ttctatttta ttactatttt aaaatatgga | 120 |
| ttgtgatytg ccaakttgat tctctggccc attaatagtt tgaaaatctc ttctgtagga | 180 |
| gtataggaat taccacagag ttttgagaaa ttgatgaatg ccacgcttta cctgtgggaa | 240 |
| cgtagattct a | 251 |

<210> SEQ ID NO 138
<211> LENGTH: 191
<212> TYPE: DNA
<213> ORGANISM: Canis familiaris

<400> SEQUENCE: 138

| cagatgatga gtctggagct ggtgatctgg gctggagata atgaacctgg gagtcatcag | 60 |
| cttttggagaa agggtgtctg gcctcactct tgctwgcaca gaaagaaagt gctcattagt | 120 |
| gtcaactctc agcaacactt ggtatttgta aactttaatt tttgctgact tcatggagaa | 180 |
| ataatgtttt t | 191 |

<210> SEQ ID NO 139
<211> LENGTH: 206
<212> TYPE: DNA
<213> ORGANISM: Canis familiaris

<400> SEQUENCE: 139

| taatgataca gaaatgaatt tggcaggaat gtatggaaaa gtccgaaaag ctgctagttc | 60 |
| aattgaccag tttaggtaag caagtgcagt actggtgagg aatggkgcat cggctccttc | 120 |
| tgtgctattt tccggtggct ccagtcacag ccccatcaag cagagctgat acctaaagtg | 180 |
| acatttaccc tacttcctct ctcaat | 206 |

<210> SEQ ID NO 140
<211> LENGTH: 186
<212> TYPE: DNA
<213> ORGANISM: Canis familiaris

<400> SEQUENCE: 140

| catcacttaa aatcatctca gcaagtgttg ttgaagatga ttttttataa agtatattcc | 60 |
| aatcttattc tatacttcag aagcttggaa ttctyatttg ctttgctgga ttgaaaaagt | 120 |
| ctggaagtaa ttagaatgac ttctcatact cccaccttga attctcctaa tatcaaaggc | 180 |
| tgggag | 186 |

<210> SEQ ID NO 141
<211> LENGTH: 171
<212> TYPE: DNA
<213> ORGANISM: Canis familiaris
<220> FEATURE:
<221> NAME/KEY: misc_feature
<222> LOCATION: (169)..(169)
<223> OTHER INFORMATION: n is a, c, g, or t

<400> SEQUENCE: 141
atatggagaa atgagctctt atacactttc agtggacatg taaactgtta ttgtcttttt      60
ggagagcatt tggcaggatc tatcaaagtr cacacatcat ttgattgagc aattccactt     120
ccagccatat tctggacata atttacaagt ataaaaagat gcatgtttng a              171

<210> SEQ ID NO 142
<211> LENGTH: 213
<212> TYPE: DNA
<213> ORGANISM: Canis familiaris

<400> SEQUENCE: 142
aaatattgaa agtgctttat ctacactcca atatgtaagc agcatagtag tttctttaga      60
gaatagatct gccatagtaa agtacaatgc aagcttagtc aytccagaaa ccctgagaaa     120
agcaatagag gccatatcac caggacaata cagagttagt attgctagtg aagttgagag     180
tacctcaaac tctccctcca gctcacctct tca                                   213

<210> SEQ ID NO 143
<211> LENGTH: 125
<212> TYPE: DNA
<213> ORGANISM: Canis familiaris

<400> SEQUENCE: 143 ttaaataac tacttgcagt gatttctttc ccccagtata aaatgtcagt tttgtctcaa       60
tccacccyct tcaccttaaa aagaaaaaga agtattagt tttcagtgtc atttgcctta     120
aaatg                                                                 125

<210> SEQ ID NO 144
<211> LENGTH: 20
<212> TYPE: DNA
<213> ORGANISM: Artificial Sequence
<220> FEATURE:
<223> OTHER INFORMATION: Hypoxanthine phosphoribosyltransferase (HPRT)
      forward primer

<400> SEQUENCE: 144
agcttgctgg tgaaaggac                                                   20

<210> SEQ ID NO 145
<211> LENGTH: 20
<212> TYPE: DNA
<213> ORGANISM: Artificial Sequence
<220> FEATURE:
<223> OTHER INFORMATION: Hypoxanthine phosphoribosyltransferase (HPRT)
      reverse primer

<400> SEQUENCE: 145
ttatagtcaa gggcatatcc                                                  20

<210> SEQ ID NO 146
<211> LENGTH: 19
<212> TYPE: DNA

```
<213> ORGANISM: Artificial Sequence
<220> FEATURE:
<223> OTHER INFORMATION: Metallothionein (MT1A) forward primer

<400> SEQUENCE: 146
agctgctgtg cctgatgtg                                                19

<210> SEQ ID NO 147
<211> LENGTH: 24
<212> TYPE: DNA
<213> ORGANISM: Artificial Sequence
<220> FEATURE:
<223> OTHER INFORMATION: Metallothionein (MT1A) reverse primer

<400> SEQUENCE: 147
tatacaaacg ggaatgtaga aaac                                          24

<210> SEQ ID NO 148
<211> LENGTH: 19
<212> TYPE: DNA
<213> ORGANISM: Artificial Sequence
<220> FEATURE:
<223> OTHER INFORMATION: Ribosomal protein S5 (RPS5) forward primer

<400> SEQUENCE: 148
tcactggtga gaaccccct                                                19

<210> SEQ ID NO 149
<211> LENGTH: 19
<212> TYPE: DNA
<213> ORGANISM: Artificial Sequence
<220> FEATURE:
<223> OTHER INFORMATION: Ribosomal protein S5 (RPS5) reverse primer

<400> SEQUENCE: 149
cctgattcac acggcgtag                                                19

<210> SEQ ID NO 150
<211> LENGTH: 20
<212> TYPE: DNA
<213> ORGANISM: Artificial Sequence
<220> FEATURE:
<223> OTHER INFORMATION: Ribosomal protein S19 (RPS19) forward primer

<400> SEQUENCE: 150
ccttcctcaa aaagtctggg                                               20

<210> SEQ ID NO 151
<211> LENGTH: 21
<212> TYPE: DNA
<213> ORGANISM: Artificial Sequence
<220> FEATURE:
<223> OTHER INFORMATION: Ribosomal protein S19 (RPS19) reverse primer

<400> SEQUENCE: 151
gttctcatcg tagggagcaa g                                             21

<210> SEQ ID NO 152
<211> LENGTH: 18
<212> TYPE: DNA
<213> ORGANISM: Artificial Sequence
<220> FEATURE:
<223> OTHER INFORMATION: Ribosomal protein L8 (RPL8) forward primer

<400> SEQUENCE: 152
ccatgaatcc tgtggagc                                                 18
```

<210> SEQ ID NO 153
<211> LENGTH: 18
<212> TYPE: DNA
<213> ORGANISM: Artificial Sequence
<220> FEATURE:
<223> OTHER INFORMATION: Ribosomal protein L8 (RPL8) reverse primer

<400> SEQUENCE: 153
gtagagggtt tgccgatg                                                   18

<210> SEQ ID NO 154
<211> LENGTH: 23
<212> TYPE: DNA
<213> ORGANISM: Artificial Sequence
<220> FEATURE:
<223> OTHER INFORMATION: ATPase, Cu++ transporting, alpha polypeptide
      (ATP7Ai) forward primer

<400> SEQUENCE: 154
ctacactcca atatgtaagc agc                                             23

<210> SEQ ID NO 155
<211> LENGTH: 22
<212> TYPE: DNA
<213> ORGANISM: Artificial Sequence
<220> FEATURE:
<223> OTHER INFORMATION: ATPase, Cu++ transporting, alpha polypeptide
      (ATP7Ai) reverse primer

<400> SEQUENCE: 155
aggtactctc aacttcacta gc                                              22

<210> SEQ ID NO 156
<211> LENGTH: 21
<212> TYPE: DNA
<213> ORGANISM: Artificial Sequence
<220> FEATURE:
<223> OTHER INFORMATION: ATPase, Cu++ transporting, alpha polypeptide
      (ATP7Aii) forward primer

<400> SEQUENCE: 156
aaacatcaaa ggctcctatc c                                               21

<210> SEQ ID NO 157
<211> LENGTH: 21
<212> TYPE: DNA
<213> ORGANISM: Artificial Sequence
<220> FEATURE:
<223> OTHER INFORMATION: ATPase, Cu++ transporting, alpha polypeptide
      (ATP7Aii) reverse primer

<400> SEQUENCE: 157
ggaaagcaaa gcgtattatc g                                               21

<210> SEQ ID NO 158
<211> LENGTH: 20
<212> TYPE: DNA
<213> ORGANISM: Artificial Sequence
<220> FEATURE:
<223> OTHER INFORMATION: ATPase, Cu++ transporting, alpha polypeptide
      (ATP7Aiii) forward primer

<400> SEQUENCE: 158
agtatgagtg tggattcggt                                                 20

```
<210> SEQ ID NO 159
<211> LENGTH: 22
<212> TYPE: DNA
<213> ORGANISM: Artificial Sequence
<220> FEATURE:
<223> OTHER INFORMATION: ATPase, Cu++ transporting, alpha polypeptide
      (ATP7Aiii) reverse primer

<400> SEQUENCE: 159
tttggagtct gtagtttagg gt                                              22
```